United States Patent
Rajeev et al.

(10) Patent No.: US 12,290,573 B2
(45) Date of Patent: *May 6, 2025

(54) MODIFIED RNAi AGENTS

(71) Applicant: Alnylam Pharmaceuticals, Inc., Cambridge, MA (US)

(72) Inventors: Kallanthottathil G. Rajeev, Cambridge, MA (US); Tracy Zimmermann, Cambridge, MA (US); Muthiah Manoharan, Cambridge, MA (US); Martin Maier, Cambridge, MA (US); Satyanarayana Kuchimanchi, Cambridge, MA (US); Klaus Charisse, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 316 days.

This patent is subject to a terminal disclaimer.

(21) Appl. No.: 17/848,850

(22) Filed: Jun. 24, 2022

(65) Prior Publication Data

US 2022/0331446 A1 Oct. 20, 2022

Related U.S. Application Data

(63) Continuation of application No. 16/850,555, filed on Apr. 16, 2020, now Pat. No. 11,406,716, which is a continuation of application No. 16/165,343, filed on Oct. 19, 2018, now Pat. No. 10,668,170, which is a continuation of application No. 15/706,389, filed on Sep. 15, 2017, now abandoned, which is a continuation of application No. 14/358,009, filed as application No. PCT/US2012/065601 on Nov. 16, 2012, now Pat. No. 9,796,974.

(60) Provisional application No. 61/561,710, filed on Nov. 18, 2011.

(51) Int. Cl.
 A61K 48/00 (2006.01)
 C07H 21/02 (2006.01)
 C12N 15/113 (2010.01)
 C12N 15/85 (2006.01)

(52) U.S. Cl.
 CPC ............ *A61K 48/00* (2013.01); *C07H 21/02* (2013.01); *C12N 15/113* (2013.01); *C12N 15/85* (2013.01); *C12N 2310/315* (2013.01); *C12N 2310/321* (2013.01); *C12N 2310/322* (2013.01); *C12N 2310/343* (2013.01); *C12N 2310/346* (2013.01); *C12N 2320/51* (2013.01)

(58) Field of Classification Search
 None
 See application file for complete search history.

(56) References Cited

U.S. PATENT DOCUMENTS

| | | |
|---|---|---|
| 8,586,727 B2 | 11/2013 | Kelnar et al. |
| 9,012,623 B2 | 4/2015 | Rana |
| 9,127,274 B2 | 9/2015 | Akinc et al. |
| 9,181,551 B2 | 11/2015 | McSwiggen et al. |
| 9,249,415 B2 | 2/2016 | Fitzgerald et al. |
| 9,399,775 B2 | 7/2016 | Rajeev et al. |
| 9,574,192 B2 | 2/2017 | Sehgal et al. |
| 9,701,963 B2 | 7/2017 | Fitzgerald et al. |
| 9,708,607 B2 | 7/2017 | Rajeev et al. |
| 9,783,806 B2 | 10/2017 | Butler et al. |
| 9,796,974 B2 | 10/2017 | Rajeev et al. |
| 9,850,488 B2 | 12/2017 | Fitzgerald et al. |
| 10,030,244 B2 | 7/2018 | Sehgal et al. |
| 10,119,136 B2 | 11/2018 | Manoharan et al. |
| 10,125,369 B2 | 11/2018 | Borodovsky et al. |
| 10,208,307 B2 | 2/2019 | Zimmermann et al. |
| 10,231,988 B2 | 3/2019 | Fitzgerald et al. |
| 10,233,448 B2 | 3/2019 | Maier et al. |
| 10,570,391 B2 | 2/2020 | Rajeev et al. |
| 10,668,170 B2 | 6/2020 | Rajeev et al. |
| 10,767,177 B2 | 9/2020 | Fitzgerald et al. |
| 10,913,950 B2 | 2/2021 | Butler et al. |
| 11,142,766 B2 | 10/2021 | Fitzgerald et al. |
| 11,406,716 B2 * | 8/2022 | Rajeev ............... C12N 15/85 |
| 2004/0198640 A1 | 10/2004 | Leake et al. |
| 2005/0026160 A1 | 2/2005 | Allerson et al. |

(Continued)

FOREIGN PATENT DOCUMENTS

| | | |
|---|---|---|
| EP | 2 305 805 A1 | 4/2011 |
| JP | 4948163 B2 | 3/2012 |

(Continued)

OTHER PUBLICATIONS

Braasch et al., "RNA Interference in Mammalian Cells by Chemically-Modified RNA," Biochemistry 42: 7967-7975 (2003).

(Continued)

*Primary Examiner* — Brian Whiteman
(74) *Attorney, Agent, or Firm* — Jeffrey N. Townes; Cozen O'Connor

(57) ABSTRACT

One aspect of the present invention relates to double-stranded RNAi (dsRNA) duplex agent capable of inhibiting the expression of a target gene. The dsRNA duplex comprises one or more motifs of three identical modifications on three consecutive nucleotides in one or both strand, particularly at or near the cleavage site of the strand. Other aspects of the invention relates to pharmaceutical compositions comprising these dsRNA agents suitable for therapeutic use, and methods of inhibiting the expression of a target gene by administering these dsRNA agents, e.g., for the treatment of various disease conditions.

20 Claims, No Drawings

Specification includes a Sequence Listing.

(56) References Cited

U.S. PATENT DOCUMENTS

| | | |
|---|---|---|
| 2005/0148530 A1 | 7/2005 | McSwiggen et al. |
| 2006/0094678 A1 | 5/2006 | Vornlocher et al. |
| 2006/0217331 A1 | 9/2006 | Vargeese et al. |
| 2007/0135372 A1 | 6/2007 | MacLachlan et al. |
| 2007/0167392 A1 | 7/2007 | Bhat et al. |
| 2010/0222413 A1 | 9/2010 | Stoffel et al. |
| 2010/0267813 A1 | 10/2010 | Esau et al. |

FOREIGN PATENT DOCUMENTS

| | | |
|---|---|---|
| WO | 03/070918 A2 | 8/2003 |
| WO | 2004015107 A2 | 2/2004 |
| WO | 2005/019453 A2 | 3/2005 |
| WO | 2005/035759 A2 | 4/2005 |
| WO | 2005121370 A2 | 12/2005 |
| WO | 2007/092059 A2 | 8/2007 |
| WO | 2008136902 A1 | 11/2008 |
| WO | 2009002944 A1 | 12/2008 |
| WO | 2009073809 A2 | 6/2009 |
| WO | 2009123764 A2 | 10/2009 |
| WO | 2009134487 A2 | 11/2009 |
| WO | 2010033246 A1 | 3/2010 |
| WO | 2010/078536 A1 | 7/2010 |
| WO | 2010/107957 A2 | 9/2010 |
| WO | 2010/107958 A1 | 9/2010 |
| WO | 2010148013 A2 | 12/2010 |
| WO | 2011/072082 A2 | 6/2011 |
| WO | 2011/123468 A1 | 10/2011 |
| WO | 2012037254 A1 | 3/2012 |
| WO | 2012/091496 A2 | 7/2012 |
| WO | 2013/074974 A2 | 5/2013 |
| WO | 2013/163430 A2 | 10/2013 |

OTHER PUBLICATIONS

Ashish et al., "Enhanced Light-Activated RNA Interference Using Phosphorothioate-Based dsRNA Precursors of siRNA," Pharmaceutical Research 28(12): 3050-3057 (2011).

Deleavey et al., "Chemical Modification of siRNA," Nucleic Acid Chemistry 16.3 (2009).

Rapozzi et al., "Efficient Silencing of bcr/abl Oncogene by Single and Double-Stranded siRNAs Targeted against b2a2 Transcripts," Biochemistry 43(51): 16134-16141 (2004).

Reynolds et al., "Rational siRNA design for RNA interference," Nature Biotechnology 22(3): 326-330 (2004).

Muhonen et al. Chemistry & Biodiversity, Apr. 2007, pp. 858-873.

Watts et al. (Drug Discovery Today 13, 2008, 842-855).

Eberle et al. (The Journal of Immunology, 2008, 180: 3229-3237).

Morrissey et al. Nature Biotechnology 23, 2005, 1002-1007.

Prakash et al., "Positional Effect of Chemical Modifications on Short Interference RNA Activity in Mammalian Cells," J. Med. Chem. 48:4247-4253 (2005).

Collingwood et al., "Chemical Modification Patterns Compatible with High Potency Dicer-Substrate Small Interfering RNAs," Oligonucleotides 18:187-200 (2008).

Bramsen et al., "A Large-Scale Chemical Modification Screen Identifies Design Rules to Generate siRNAs with High Activity, High Stability and Low Toxicity," Nucleic Acids Res. 37(9):2867-2881 (2009).

Deleavey et al., "Synergistic Effects Between Analogs of DNA and RNA Improve the Potency of siRNA-Mediated Gene Silencing," Nucleic Acids Res. 38(13):4547-4557 (2010).

Written Opinion of the International Search Authority PCT/US2012/065601, Mar. 2013, pp. 1-13.

Morrissey et al., "Potent and presistent in vivo anti-HBV activity of chemically modified siRNAs," Nature Biotechnology 23: 1002-1007 (2005).

Behlke, "Chemical Modification of siRNAs for In Vivo Use," Oligonucleotides 18: 305-320 (2008).

Czauderna et al., "Structural variations and stabilising modifications of syntehtic SIRNAs in mammalian cells," Nucleic Acids Research 31: 2705-2716 (2003).

\* cited by examiner

SEQUENCE LISTING

```
<160> NUMBER OF SEQ ID NOS: 1208

<210> SEQ ID NO 1
<211> LENGTH: 16
<212> TYPE: PRT
<213> ORGANISM: Unknown
<220> FEATURE:
<223> OTHER INFORMATION: Description of Unknown: Exemplary
      hydrophobic membrane translocation peptide

<400> SEQUENCE: 1

Ala Ala Val Ala Leu Leu Pro Ala Val Leu Leu Ala Leu Leu Ala Pro
1               5                   10                  15

<210> SEQ ID NO 2
<211> LENGTH: 11
<212> TYPE: PRT
<213> ORGANISM: Unknown
<220> FEATURE:
<223> OTHER INFORMATION: Description of Unknown: RFGF
      analogue peptide

<400> SEQUENCE: 2

Ala Ala Leu Leu Pro Val Leu Leu Ala Ala Pro
1               5                   10

<210> SEQ ID NO 3
<211> LENGTH: 13
<212> TYPE: PRT
<213> ORGANISM: Human immunodeficiency virus

<400> SEQUENCE: 3

Gly Arg Lys Lys Arg Arg Gln Arg Arg Arg Pro Pro Gln
1               5                   10

<210> SEQ ID NO 4
```

```
<211> LENGTH: 16
<212> TYPE: PRT
<213> ORGANISM: Drosophila sp.

<400> SEQUENCE: 4

Arg Gln Ile Lys Ile Trp Phe Gln Asn Arg Arg Met Lys Trp Lys Lys
1               5                   10                  15

<210> SEQ ID NO 5
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
auguaaccaa gaguauucca u                                            21

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
auguaaccaa gaguauucca u                                            21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
auguaaccaa gaguauucca u                                            21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
auguaaccaa gaguauucca u                                            21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
auguaaccca gaguauucca u                                            21

<210> SEQ ID NO 10
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 10
auguaaccaa gaguauucca u                                              21

<210> SEQ ID NO 11
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
auguaaccaa gaguauucca u                                              21

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
auguaaccaa gaguauucca u                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 13
auguaaccaa gaguauacga u                                              21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ugggauuuca uguaaccaag a                                              21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ugggauuuca uguaaccaag a                                              21
```

```
<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
auguaaccaa gaguauucca u                                              21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ugggauuuca uguaaccaag a                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 18
auguaaccaa gaguauacga u                                              21

<210> SEQ ID NO 19
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
auguaaccaa gaguauucca u                                              21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 20
auguaaccaa gagtatucca u                                              21

<210> SEQ ID NO 21
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
auguaaccaa gaguauucca u                                              21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22
ugggauuuca uguaaccaag a                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
auguaaccaa gaguauucca u                                              21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24
auguaaccaa gaguauucca u                                              21

<210> SEQ ID NO 25
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
auguaaccaa gaguauucca u                                              21

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
auguaaccaa gaguauucca u                                              21

<210> SEQ ID NO 27
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 27
tgggatuuca ugtaaccaag a                                                 21

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 28
auguaaccaa gaguauucca u                                                 21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ugggauuuca uguaaccaag a                                                 21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ugggauuuca uguaaccaag a                                                 21

<210> SEQ ID NO 31
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
ugggauuuca uguaaccaag a                                                 21

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32
```
ugggauuuca uguaaccaag a						21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 33
atguaaccaa gagtautcca t						21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 34
atgtaaccaa gagtatucca u						21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 35
ugggauuuca uguaaccaag a						21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 36
auguaaccaa gaguauucca u						21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
auguaaccaa gaguauucca u						21

```
<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
ugggauuuca uguaaccaag a                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
auguaaccaa gaguauucca u                                              21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
ugggauuuca uguaaccaag a                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 41
ugggauuuca uguaaccaag a                                              21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 42
ugggauuuca uguaaccaag a                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 43
ugggauuuca uguaaccaag a                                              21
```

```
<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 44
auguaaccaa gaguauucca u                                              21

<210> SEQ ID NO 45
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
auguaaccaa gaguauucca u                                              21

<210> SEQ ID NO 46
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
auguaaccaa gaguauucca u                                              21

<210> SEQ ID NO 47
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 47
ugggauuuca uguaaccaag a                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 48
auguaaccaa gaguauucca u                                              21

<210> SEQ ID NO 49
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 49
auguaaccaa gaguauucca u                                              21

<210> SEQ ID NO 50
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
auguaaccaa gaggauucca u                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
auguaaccaa gaguauucca u                                              21

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
ugggauuuca uguaaccaag a                                              21

<210> SEQ ID NO 53
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
auguaaccaa gaguauucca u                                              21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
auguaaccaa gaguauucca u                                              21

<210> SEQ ID NO 55
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
ugggauuuca uguaaccaag a                                              21

<210> SEQ ID NO 56
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
auguaaccaa gaguauucca u                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 57
auguaaccaa gagtatucca u                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 58
auguaaccaa gagtatucca u                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 59
auguaaccaa gagtauucca u                                              21

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<223> OTHER INFORMATION: see specification as filed for detailed
      description of substitutions and preferred embodiments

<400> SEQUENCE: 60
auguaaccaa gagtatucca u                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
auguaaccaa gaguauucca u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
auguaaccaa gaguauucca u                                              21

<210> SEQ ID NO 63
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 63
auguaaccaa gaguauucca u                                              21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 64
auguaaccaa gagtatucca u                                              21

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments
```

<400> SEQUENCE: 65
atguaaccaa gagtatucca t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 66
auguaaccaa gaguauucca u                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 67
auguaaccaa gagtatucca u                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 68
atguaaccca gagtauucca u                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 69
auguaaccaa gagtauucca u                                          21

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 70
auguaaccaa gagtatucca u                                          21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 71
auguaaccaa gaguatucca u                                          21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 72
auguaaccaa gagtatucca u                                          21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 73
auguaaccaa gagtatucca u                                          21

```
<210> SEQ ID NO 74
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 74
auguaaccca gaguauucca u                                              21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 75
auguaaccaa gaguauucca u                                              21

<210> SEQ ID NO 76
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 76
ugggauuuca uguaaccaag a                                              21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 77
auguaaccaa gaguauucca u                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 78
auguaaccaa gagtatucca u                                              21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 79
auguaaccaa gaguauucca u                                              21

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
auguaaccaa gaguauucca u                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 81
auguaaccaa gaguattcca u                                              21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
auguaaccaa gaguauucca u                                              21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
auguaaccaa gaguauucca u                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 84
```
auguaaccaa gagtatucca u         21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 85
auguaaccaa gaguauucca u         21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 86
auguaaccaa gaguauucca t         21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
auguaaccaa gaguauucca u         21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88
auguaaccaa gaguauucca u         21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
auguaaccaa gaguauucca u         21

<210> SEQ ID NO 90
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 90
auguaaccaa gaguauucca u                                              21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
auguaaccaa gaguauucca u                                              21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
auguaaccaa gaguauucca u                                              21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
auguaaccaa gaguauucca u                                              21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
auguaaccaa gaguauucca u                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
auguaaccaa gaguauucca u                                              21

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 96
auguaaccaa gagtatucca u                                              21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
auguaaccaa gaguauucca u                                              21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
auguaaccaa gaguauucca u                                              21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
auguaaccaa gaguauucca u                                              21

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
auguaaccaa gaguauucca u                                              21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
auguaaccaa gaguauucca u                                              21

<210> SEQ ID NO 102
```

<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
auguaaccaa gaguauucca u                                              21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
auguaaccaa gaguauucca u                                              21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
auguaaccaa gaguauucca u                                              21

<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
auguaaccaa gaguauucca u                                              21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
auguaaccaa gaguauucca u                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
auguaaccaa gaguauucca u                                              21

<210> SEQ ID NO 108
<211> LENGTH: 21

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
auguaaccaa gaguauucca u                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 109
auguaaccaa gaguauucca u                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 110
auguaaccaa gaguauucca u                                              21

<210> SEQ ID NO 111
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 111
auguaaccaa gaguauucca u                                              21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 112
auguaaccaa gaguauucca u                                              21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 113
```
auguaaccaa gagtatucca u					21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
auguaaccaa gaguauucca u					21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
auguaaccaa gaguauucca u					21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
auguaaccaa gaguauucca u					21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117
auguaaccaa gaguauucca u					21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
auguaaccaa gaguauucca u					21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
auguaaccaa gaguauucca u					21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
auguaaccaa gaguauucca u                                              21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
auguaaccaa gaguauucca u                                              21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
auguaaccaa gaguauucca u                                              21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
auguaaccaa gaguauucca u                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
auguaaccaa gaguauucca u                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
auguaaccaa gaguauucca u                                              21

```
<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
auguaaccaa gaguauucca u                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 127
auguaaccaa gaguauucca u                                              21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 128
auguaaccaa gaguauucca u                                              21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
auguaaccaa gaguauucca u                                              21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
auguaaccaa gaguauucca u                                              21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
auguaaccaa gaguauucca u                                              21
```

-continued

```
<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 132
auguaaccaa gaguauucca u                                              21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 133
auguaaccaa gaguauucca u                                              21

<210> SEQ ID NO 134
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 134
auguaaccaa gaguauucca u                                              21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 135
auguaaccaa gaguauucca u                                              21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
auguaaccaa gaguauucca u                                              21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
auguaaccaa gaguauucca u                                              21

<210> SEQ ID NO 138
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
auguaaccaa gaguauucca u                                              21

<210> SEQ ID NO 139
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
auguaaccaa gaguauucca u                                              21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
auguaaccaa gaguauucca u                                              21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
auguaaccaa gaguauucca u                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
auguaaccaa gaguauucca u                                              21

<210> SEQ ID NO 143
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
auguaaccaa gaguauucca u                                              21

<210> SEQ ID NO 144
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
auguaaccaa gaguauucca u                                              21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
auguaaccaa gaguauucca u                                              21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 146
auguaaccaa gaguauucca u                                              21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 147
auguaaccaa gaguauucca u                                              21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 148
auguaaccaa gaguauucca u                                              21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 149
auguaaccaa gaguauucca u                                              21

<210> SEQ ID NO 150
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 150
auguaaccaa gaguauucca u                                                    21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 151
auguaaccaa gaguauucca u                                                    21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
auguaaccaa gaguauucca u                                                    21

<210> SEQ ID NO 153
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
auguaaccaa gaguauucca u                                                    21

<210> SEQ ID NO 154
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
auguaaccaa gaguauucca u                                                    21

<210> SEQ ID NO 155
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
auguaaccaa gaguauucca u                                                    21

<210> SEQ ID NO 156
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 156
auguaaccaa gaguauucca u                                              21

<210> SEQ ID NO 157
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 157
auguaaccaa gaguauucca u                                              21

<210> SEQ ID NO 158
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 158
auguaaccaa gaguauucca u                                              21

<210> SEQ ID NO 159
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 159
ugggauuuca uguaaccaag a                                              21

<210> SEQ ID NO 160
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 160
ugggauuuca uguaaccaag a                                              21

<210> SEQ ID NO 161
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 161
ugggauuuca uguaaccaag a                                              21

<210> SEQ ID NO 162
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 162
ugggauuuca uguaaccaag a                                              21

<210> SEQ ID NO 163
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 163
ugggauuuca uguaaccaag a                                              21

<210> SEQ ID NO 164
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 164
ugggauuuca uguaaccaag a                                              21

<210> SEQ ID NO 165
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
ugggauuuca uguaaccaag a                                              21

<210> SEQ ID NO 166
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ugggauuuca uguaaccaag a                                              21

<210> SEQ ID NO 167
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 167
auguaaccaa gaguauucca u                                              21

<210> SEQ ID NO 168
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 168
auguaaccaa gaguauucca u                                              21

<210> SEQ ID NO 169
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 169
auguaaccaa gaguauucca u                                              21

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 170
auguaaccaa gaguauucca u                                              21

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 171
auguaaccaa gaguauucca u                                              21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 172
auguaaccaa gaguauucca u                                              21

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 173
auguaaccaa gaguauucca u                                              21

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 174
auguaaccaa gaguauucca u                                              21

<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 175
auguaaccaa gaguauucca u                                              21

<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 176
auguaaccaa gaguauucca u                                              21

<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 177
auguaaccaa gaguauucca u                                              21

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 178
auguaaccaa gaguauucca u                                              21

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 179
auguaaccaa gaguauucca u                                              21

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 180
auguaaccaa gaguauucca u                                              21

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 181
auguaaccaa gaguauucca u                                              21

<210> SEQ ID NO 182
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 182
auguaaccaa gaguauucca u                                              21

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 183
auguaaccaa gaguauucca u                                              21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 184
auguaaccaa gaguauucca u                                              21

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 185
auguaaccaa gaguauucca u                                              21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 186
```
auguaaccaa gaguauucca u                                            21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
auguaaccaa gaguauucca u                                            21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
auguaaccaa gaguauucca u                                            21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
auguaaccaa gaguauucca u                                            21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
auguaaccaa gaguauucca u                                            21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
auguaaccaa gaguauucca u                                            21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 192
auguaaccaa gaguauucca u                                          21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
auguaaccaa gaguauucca u                                          21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
auguaaccaa gaguauucca u                                          21

<210> SEQ ID NO 195
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195
auguaaccaa gaguauucca u                                          21

<210> SEQ ID NO 196
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
auguaaccaa gaguauucca u                                          21

<210> SEQ ID NO 197
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
auguaaccaa gaguauucca u                                          21

<210> SEQ ID NO 198
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 198
auguaaccaa gaguauucca u                                          21

<210> SEQ ID NO 199
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
auguaaccaa gaguauucca u                                                  21

<210> SEQ ID NO 200
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
auguaaccaa gaguauucca u                                                  21

<210> SEQ ID NO 201
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
auguaaccaa gaguauucca u                                                  21

<210> SEQ ID NO 202
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
auguaaccaa gaguauucca u                                                  21

<210> SEQ ID NO 203
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 203
auguaaccaa gaguauucca u                                                  21

<210> SEQ ID NO 204
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 204
auguaaccaa gaguauucca u                                                  21

```
<210> SEQ ID NO 205
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 205
auguaaccaa gaguauucca u                                              21

<210> SEQ ID NO 206
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 206
auguaaccaa gaguauucca u                                              21

<210> SEQ ID NO 207
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 207
auguaaccaa gaguauucca u                                              21

<210> SEQ ID NO 208
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 208
auguaaccaa gaguauucca u                                              21

<210> SEQ ID NO 209
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 209
auguaaccaa gaguauucca u                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments
```

```
<400> SEQUENCE: 210
auguaaccaa gagtattcca u                                              21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 211
auguaaccaa gaguauucca u                                              21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 212
auguaaccaa gaguauucca u                                              21

<210> SEQ ID NO 213
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 213
auguaaccaa gaguauucca u                                              21

<210> SEQ ID NO 214
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 214
auguaaccaa gaguauucca u                                              21

<210> SEQ ID NO 215
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
auguaaccaa gaguauucca u                                              21

<210> SEQ ID NO 216
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

<400> SEQUENCE: 216
auguaaccaa gaguauucca u						21

<210> SEQ ID NO 217
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
auguaaccaa gaguauucca u						21

<210> SEQ ID NO 218
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 218
auguaaccaa gaguautcca u						21

<210> SEQ ID NO 219
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
auguaaccaa gaguauucca u						21

<210> SEQ ID NO 220
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 220
auguaaccaa gaguattcca u						21

<210> SEQ ID NO 221
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221

-continued auguaaccaa gaguauucca u                                          21

<210> SEQ ID NO 222
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
auguaaccaa gaguauucca u                                          21

<210> SEQ ID NO 223
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
auguaaccaa gaguauucca u                                          21

<210> SEQ ID NO 224
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
auguaaccaa gaguauucca u                                          21

<210> SEQ ID NO 225
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
auguaaccaa gaguauucca u                                          21

<210> SEQ ID NO 226
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
auguaaccaa gaguauucca u                                          21

<210> SEQ ID NO 227
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
auguaaccaa gaguauucca u                                          21

<210> SEQ ID NO 228
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
auguaaccaa gaguauucca u                                              21

<210> SEQ ID NO 229
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
auguaaccaa gaguauucca u                                              21

<210> SEQ ID NO 230
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
auguaaccaa gaguauucca u                                              21

<210> SEQ ID NO 231
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
auguaaccaa gaguauucca u                                              21

<210> SEQ ID NO 232
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 232
auguaaccaa gaguauucca u                                              21

<210> SEQ ID NO 233
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
auguaaccaa gaguauucca u                                              21

<210> SEQ ID NO 234
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
auguaaccaa gaguauucca u                                              21

<210> SEQ ID NO 235
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
auguaaccaa gaguauucca u                                              21

<210> SEQ ID NO 236
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
auguaaccaa gaguauucca u                                              21

<210> SEQ ID NO 237
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
auguaaccaa gaguauucca u                                              21

<210> SEQ ID NO 238
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 238
auguaaccaa gaguauucca u                                              21

<210> SEQ ID NO 239
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
auguaaccaa gaguauucca u                                              21

```
<210> SEQ ID NO 240
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
auguaaccaa gaguauucca u                                              21

<210> SEQ ID NO 241
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
auguaaccaa gaguauucca u                                              21

<210> SEQ ID NO 242
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
auguaaccaa gaguauucca u                                              21

<210> SEQ ID NO 243
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
auguaaccaa gaguauucca u                                              21

<210> SEQ ID NO 244
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 244
auguaaccaa gaguauucca u                                              21

<210> SEQ ID NO 245
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
auguaaccaa gaguauucca u                                              21

<210> SEQ ID NO 246
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 246
auguaaccaa gaguauucca u                                              21

<210> SEQ ID NO 247
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 247
auguaaccaa gaguauucca u                                              21

<210> SEQ ID NO 248
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
auguaaccaa gaguauucca u                                              21

<210> SEQ ID NO 249
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249
auguaaccaa gaguauucca u                                              21

<210> SEQ ID NO 250
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 250
auguaaccaa gaguauucca u                                              21

<210> SEQ ID NO 251
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
auguaaccaa gaguauucca u                                              21

<210> SEQ ID NO 252
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
auguaaccaa gaguauucca u                                              21

<210> SEQ ID NO 253
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 253
aacaauguuc uugcucuaua a                                              21

<210> SEQ ID NO 254
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
aacaguguuc uugcucuaua a                                              21

<210> SEQ ID NO 255
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
aacaguguuc uugcucuaua a                                              21

<210> SEQ ID NO 256
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
aacaguguuc uugcucuaua a                                              21

<210> SEQ ID NO 257
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<223> OTHER INFORMATION: see specification as filed for detailed
      description of substitutions and preferred embodiments

<400> SEQUENCE: 257
caguguucuu gcucuauaat t                                               21

<210> SEQ ID NO 258
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
aacaguguuc uugcucuaua a                                               21

<210> SEQ ID NO 259
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
aacaguguuc uugcucuaua a                                               21

<210> SEQ ID NO 260
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
aacaguguuc uugcucuaua a                                               21

<210> SEQ ID NO 261
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
aacaguguuc uugcucuaua a                                               21

<210> SEQ ID NO 262
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 262
aacaguguuc uugcucuaua a                                               21

<210> SEQ ID NO 263
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 263
aacaguguuc uugcucuaua a                                              21

<210> SEQ ID NO 264
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 264
aacaguguuc uugcucuaua a                                              21

<210> SEQ ID NO 265
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 265
aacaguguuc uugcucuaua a                                              21

<210> SEQ ID NO 266
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 266
aacaguguuc uugcucuaua a                                              21

<210> SEQ ID NO 267
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 267
aacaguguuc uugcucuaua a                                              21

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 268
caguguucuu gcucuauaat t                                              21
```

```
<210> SEQ ID NO 269
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 269
aacaguguuc uugcucuaua a                                              21

<210> SEQ ID NO 270
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 270
aacaguguuc uugcucuaua a                                              21

<210> SEQ ID NO 271
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 271
aacaguguuc uugcucuaua a                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 272
aacaauguuc uugcucuaua a                                              21

<210> SEQ ID NO 273
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 273
aacaguguuc uugcucuaua a                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

-continued

```
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 274
caguguucuu gcucuauaat t                                                    21

<210> SEQ ID NO 275
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
aacaguguuc uugcucuaua a                                                    21

<210> SEQ ID NO 276
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
aacaguguuc uugcucuaua a                                                    21

<210> SEQ ID NO 277
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 277
caguguucuu gcucuauaat t                                                    21

<210> SEQ ID NO 278
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
aacaguguuc uugcucuaua a                                                    21

<210> SEQ ID NO 279
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
```
aacaguguuc uugcucuaua a                                              21

<210> SEQ ID NO 280
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 280
caguguucuu gcucuauaat t                                              21

<210> SEQ ID NO 281
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
aacaguguuc uugcucuaua a                                              21

<210> SEQ ID NO 282
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
aacaguguuc uugcucuaua a                                              21

<210> SEQ ID NO 283
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
aacaguguuc uugcucuaua a                                              21

<210> SEQ ID NO 284
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 284
caguguucuu gcucuauaat t                                              21

```
<210> SEQ ID NO 285
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
aacaguguuc uugcucuaua a                                             21

<210> SEQ ID NO 286
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
aacaguguuc uugcucuaua a                                             21

<210> SEQ ID NO 287
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
aacaguguuc uugcucuaua a                                             21

<210> SEQ ID NO 288
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
aacaguguuc uugcucuaua a                                             21

<210> SEQ ID NO 289
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
aacaguguuc uugcucuaua a                                             21

<210> SEQ ID NO 290
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 290
aacaguguuc uugcucuaua a                                             21
```

```
<210> SEQ ID NO 291
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
aacaguguuc uugcucuaua a                                              21

<210> SEQ ID NO 292
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
aacaguguuc uugcucuaua a                                              21

<210> SEQ ID NO 293
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
aacaguguuc uugcucuaua a                                              21

<210> SEQ ID NO 294
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
aacaguguuc uugcucuaua a                                              21

<210> SEQ ID NO 295
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
aacaguguuc uugcucuaua a                                              21

<210> SEQ ID NO 296
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
aacaguguuc uugcucuaua a                                              21

<210> SEQ ID NO 297
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
aacaguguuc uugcucuaua a                                             21

<210> SEQ ID NO 298
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
aacaguguuc uugcucuaua a                                             21

<210> SEQ ID NO 299
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
aacaguguuc uugcucuaua a                                             21

<210> SEQ ID NO 300
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
aacaguguuc uugcucuaua a                                             21

<210> SEQ ID NO 301
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 301
aacagtguuc tugctcuata a                                             21

<210> SEQ ID NO 302
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 302
```

```
aacaguguuc uugcucuaua a                                              21

<210> SEQ ID NO 303
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
aacaguguuc uugcucuaua a                                              21

<210> SEQ ID NO 304
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
aacaguguuc uugcucuaua a                                              21

<210> SEQ ID NO 305
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
aacaguguuc uugcucuaua a                                              21

<210> SEQ ID NO 306
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
aacaguguuc uugcucuaua a                                              21

<210> SEQ ID NO 307
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
aacaguguuc uugcucuaua a                                              21

<210> SEQ ID NO 308
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 308
```
aacaguguuc uugcucuaua a                                             21

<210> SEQ ID NO 309
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
aacaguguuc uugcucuaua a                                             21

<210> SEQ ID NO 310
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 310
aacagugtuc ttgctcuata a                                             21

<210> SEQ ID NO 311
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 311
aacaguguuc uugcucuaua a                                             21

<210> SEQ ID NO 312
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 312
aacaguguuc utgcucuaua a                                             21

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 313
aacaguguuc uugcucuaua a                                                21

<210> SEQ ID NO 314
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 314
aacaguguuc utgcucuaua a                                                21

<210> SEQ ID NO 315
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 315
aacaauguuc utgcucuaua a                                                21

<210> SEQ ID NO 316
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 316
aacaauguuc uugcucuata a                                                21

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide
<220> FEATURE:
<223> OTHER INFORMATION: see specification as filed for detailed
      description of substitutions and preferred embodiments

<400> SEQUENCE: 317
aacaguguuc uugcucuaua a                                              21

<210> SEQ ID NO 318
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
aacaguguuc uugcucuaua a                                              21

<210> SEQ ID NO 319
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
aacaguguuc uugcucuaua a                                              21

<210> SEQ ID NO 320
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 320
aacaguguuc uugcucuaua a                                              21

<210> SEQ ID NO 321
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
aacaguguuc uugcucuaua a                                              21

<210> SEQ ID NO 322
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
aacaguguuc uugcucuaua a                                              21

<210> SEQ ID NO 323
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 323
aacaguguuc uugcucuaua a                                                   21

<210> SEQ ID NO 324
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 324
aacaguguuc uugcucuaua a                                                   21

<210> SEQ ID NO 325
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 325
aacaguguuc uugcucuaua a                                                   21

<210> SEQ ID NO 326
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 326
aacaguguuc uugcucuaua a                                                   21

<210> SEQ ID NO 327
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 327
aacaguguuc uugcucuaua a                                                   21

<210> SEQ ID NO 328
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 328
aacaguguuc uugcucuaua a                                                   21

<210> SEQ ID NO 329
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 329
aacaguguuc uugcucuaua a                                             21

<210> SEQ ID NO 330
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 330
aacaguguuc uugcucuaua a                                             21

<210> SEQ ID NO 331
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 331
aacaguguuc uugcucuaua a                                             21

<210> SEQ ID NO 332
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 332
aacaguguuc uugcucuaua a                                             21

<210> SEQ ID NO 333
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 333
aacaguguuc uugcucuaua a                                             21

<210> SEQ ID NO 334
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 334
aacaguguuc uugcucuaua a                                             21

<210> SEQ ID NO 335
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 335
aacaguguuc uugcucuaua a                                              21

<210> SEQ ID NO 336
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 336
aacaguguuc uugcucuaua a                                              21

<210> SEQ ID NO 337
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 337
aacaguguuc uugcucuaua a                                              21

<210> SEQ ID NO 338
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 338
aacaguguuc uugcucuaua a                                              21

<210> SEQ ID NO 339
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 339
aacaguguuc uugcucuaua a                                              21

<210> SEQ ID NO 340
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 340
aacaguguuc uugcucuaua a                                              21

<210> SEQ ID NO 341
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 341
aacaguguuc uugcucuaua a					21

<210> SEQ ID NO 342
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 342
aacaguguuc uugcucuaua a					21

<210> SEQ ID NO 343
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 343
aacaguguuc uugcucuaua a					21

<210> SEQ ID NO 344
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 344
aacaguguuc uugcucuaua a					21

<210> SEQ ID NO 345
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 345
aacaguguuc uugcucuaua a					21

<210> SEQ ID NO 346
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 346
aacaguguuc uugcucuaua a					21

<210> SEQ ID NO 347
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 347
aacaguguuc uugcucuaua a                                              21

<210> SEQ ID NO 348
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 348
aacaguguuc uugcucuaua a                                              21

<210> SEQ ID NO 349
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 349
aacaguguuc uugcucuaua a                                              21

<210> SEQ ID NO 350
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 350
aacaguguuc uugcucuaua a                                              21

<210> SEQ ID NO 351
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 351
aacaguguuc uugcucuaua a                                              21

<210> SEQ ID NO 352
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 352
aacaguguuc uugcucuaua a                                              21

<210> SEQ ID NO 353
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 353
```
aacaguguuc uugcucuaua a                                              21

<210> SEQ ID NO 354
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 354
aacaguguuc uugcucuaua a                                              21

<210> SEQ ID NO 355
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 355
aacaguguuc uugcucuaua a                                              21

<210> SEQ ID NO 356
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 356
aacaguguuc uugcucuaua a                                              21

<210> SEQ ID NO 357
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 357
aacaguguuc uugcucuaua a                                              21

<210> SEQ ID NO 358
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 358
aacaguguuc uugcucuaua a                                              21

<210> SEQ ID NO 359
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 359
aacaguguuc uugcucuaua a                                              21

<210> SEQ ID NO 360
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 360
aacaguguuc uugcucuaua a                                              21

<210> SEQ ID NO 361
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 361
aacaguguuc uugcucuaua a                                              21

<210> SEQ ID NO 362
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 362
aacaguguuc uugcucuaua a                                              21

<210> SEQ ID NO 363
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 363
aacaguguuc uugcucuaua a                                              21

<210> SEQ ID NO 364
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 364
aacaguguuc uugcucuaua a                                              21

<210> SEQ ID NO 365
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 365
aacaguguuc uugcucuaua a                                              21

<210> SEQ ID NO 366
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 366
aacaguguuc uugcucuaua a                                              21

<210> SEQ ID NO 367
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 367
aacaguguuc uugcucuaua a                                              21

<210> SEQ ID NO 368
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 368
aacaguguuc uugcucuaua a                                              21

<210> SEQ ID NO 369
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 369
aacaguguuc uugcucuaua a                                              21

<210> SEQ ID NO 370
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 370
aacaguguuc uugcucuaua a                                              21

<210> SEQ ID NO 371
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 371
aacaguguuc uugcucuaua a                                              21

```
<210> SEQ ID NO 372
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 372
aacaguguuc uugcucuaua a                                           21

<210> SEQ ID NO 373
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 373
aacaguguuc uugcucuaua a                                           21

<210> SEQ ID NO 374
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 374
aacaguguuc uugcucuaua a                                           21

<210> SEQ ID NO 375
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 375
aacaguguuc uugcucuaua a                                           21

<210> SEQ ID NO 376
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 376
aacaguguuc uugcucuaua a                                           21

<210> SEQ ID NO 377
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 377
aacaguguuc uugcucuaua a                                           21
```

```
<210> SEQ ID NO 378
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 378
aacaguguuc uugcucuaua a                                              21

<210> SEQ ID NO 379
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 379
aacaguguuc uugcucuaua a                                              21

<210> SEQ ID NO 380
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 380
aacaguguuc uugcucuaua a                                              21

<210> SEQ ID NO 381
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 381
aacaguguuc uugcucuaua a                                              21

<210> SEQ ID NO 382
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 382
aacaguguuc uugcucuaua a                                              21

<210> SEQ ID NO 383
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 383
aacaguguuc uugcucuaua a                                              21

<210> SEQ ID NO 384
```

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 384
aacaguguuc uugcucuaua a                                              21

<210> SEQ ID NO 385
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 385
aacaguguuc uugcucuaua a                                              21

<210> SEQ ID NO 386
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 386
aacaguguuc uugcucuaua a                                              21

<210> SEQ ID NO 387
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 387
aacaguguuc uugcucuaua a                                              21

<210> SEQ ID NO 388
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 388
aacaguguuc uugcucuaua a                                              21

<210> SEQ ID NO 389
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 389
aacaguguuc uugcucuaua a                                              21

<210> SEQ ID NO 390
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 390
aacaguguuc uugcucuaua a                                              21

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 391
aacaguguuc uugcucuaua a                                              21

<210> SEQ ID NO 392
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 392
aacaguguuc uugcucuaua a                                              21

<210> SEQ ID NO 393
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 393
aacaguguuc uugcucuaua a                                              21

<210> SEQ ID NO 394
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 394
aacaguguuc uugcucuaua a                                              21

<210> SEQ ID NO 395
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 395
```
aacaguguuc uugcucuaua a                                           21

<210> SEQ ID NO 396
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 396
aacaguguuc tugctctata a                                           21

<210> SEQ ID NO 397
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 397
aacaguguuc uugcucuaua a                                           21

<210> SEQ ID NO 398
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 398
aacaguguuc uugcucuaua a                                           21

<210> SEQ ID NO 399
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 399
aacaguguuc uugcucuaua a                                           21

<210> SEQ ID NO 400
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 400
aacaguguuc uugcucuaua a                                           21

<210> SEQ ID NO 401
<211> LENGTH: 21
<212> TYPE: RNA
<213> ORGANISM: Artificial Sequence
<220> FEATURE:

```
<223> OTHER INFORMATION: Description of Artificial Sequence: Synthetic
      oligonucleotide

<400> SEQUENCE: 401
aacaguguuc uugcucuaua a                                              21

<210> SEQ ID NO 402
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 402
aacaauguuc uugcactaua a                                              21

<210> SEQ ID NO 403
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 403
aacaguguuc uugcucuaua a                                              21

<210> SEQ ID NO 404
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 404
aacagugutc uugcuctaua a                                              21

<210> SEQ ID NO 405
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 405
aacaauguuc uugcactaua a                                              21

<210> SEQ ID NO 406
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 406
aacaauguuc uugcacuaua a                                              21

<210> SEQ ID NO 407
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 407
aacaguguuc uugcucuaua a                                              21

<210> SEQ ID NO 408
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 408
aacaauguuc uugcacuata a                                              21

<210> SEQ ID NO 409
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 409
aacaguguuc uugcucuaua a                                              21

<210> SEQ ID NO 410
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 410
aacaguguuc uugcucuaua a                                              21

<210> SEQ ID NO 411
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 411
aacaauguuc uugcacuata a                                              21

<210> SEQ ID NO 412
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 412
aacaguguuc uugcucuaua a                                              21

<210> SEQ ID NO 413
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 413
aacaauguuc uugcactata a                                              21

<210> SEQ ID NO 414
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 414
aacaguguuc uugcucuaua a                                              21

<210> SEQ ID NO 415
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 415
aacaauguuc uugcactata a                                              21
```

<210> SEQ ID NO 416
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 416
aacaguguuc uugcucuaua a                                           21

<210> SEQ ID NO 417
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 417
aacagugtuc utgcucuaua a                                           21

<210> SEQ ID NO 418
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 418
aacaguguuc uugcucuaua a                                           21

<210> SEQ ID NO 419
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 419
aacaguguuc uugcucuaua a                                           21

<210> SEQ ID NO 420
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 420
aacaguguuc uugcucuaua a                                           21

<210> SEQ ID NO 421
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 421
aacaguguuc uugcucuaua a                          21

<210> SEQ ID NO 422
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 422
aacaguguuc uugcucuaua a                          21

<210> SEQ ID NO 423
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 423
aacaguguuc uugcucuaua a                          21

<210> SEQ ID NO 424
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 424
aacaguguuc uugcucuaua a                          21

<210> SEQ ID NO 425
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 425
auggaauacu cuugguuaca uga                        23

<210> SEQ ID NO 426
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 426
auggaauacu cuugguuaca uga                        23

<210> SEQ ID NO 427
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 427
auggaauacu cuugguuaca uga                                          23

<210> SEQ ID NO 428
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 428
auggaauacu cuugguuaca uga                                          23

<210> SEQ ID NO 429
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 429
auggaauacu cuugguuaca uga                                          23

<210> SEQ ID NO 430
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 430
auggaauacu cuugguuaca uga                                          23

<210> SEQ ID NO 431
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 431
auggaauacu cuugguuaca uga                                          23

<210> SEQ ID NO 432
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 432
auggaauacu cuugguuaca uga                                          23

<210> SEQ ID NO 433
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 433
```
auggaauacu cuugguuaca uga                                              23

<210> SEQ ID NO 434
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 434
ucuugguuac augaaauccc auc                                              23

<210> SEQ ID NO 435
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 435
ucuugguuac augaaauccc auc                                              23

<210> SEQ ID NO 436
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 436
auggaauacu cuugguuaca uga                                              23

<210> SEQ ID NO 437
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 437
ucuugguuac augaaauccc auc                                              23

<210> SEQ ID NO 438
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 438
auggaauacu cuuggutaca tga                                              23

<210> SEQ ID NO 439
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 439
auggaauacu cuugguuaca uga                                              23

<210> SEQ ID NO 440
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 440
auggaatacu cuugguuaca uga                                              23

<210> SEQ ID NO 441
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 441
auggaauacu cuugguuaca uga                                              23

<210> SEQ ID NO 442
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 442
ucuugguuac augaaauccc auc                                              23

<210> SEQ ID NO 443
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 443
auggaauacu cuugguuaca uga                                              23

<210> SEQ ID NO 444
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 444
auggaauacu cuugguuaca uga                                              23
```

<210> SEQ ID NO 445
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 445
auggaauacu cuugguuaca uga                                              23

<210> SEQ ID NO 446
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 446
auggaauacu cuugguuaca uga                                              23

<210> SEQ ID NO 447
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 447
uctuggtuac augaaauccc atc                                              23

<210> SEQ ID NO 448
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 448
auggaauacu cuugguuaca uga                                              23

<210> SEQ ID NO 449
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 449
ucuugguuac augaaauccc auc                                              23

<210> SEQ ID NO 450
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 450
ucuugguuac augaaauccc auc                                          23

<210> SEQ ID NO 451
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 451
ucuugguuac augaaauccc auc                                          23

<210> SEQ ID NO 452
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 452
ucuugguuac augaaauccc auc                                          23

<210> SEQ ID NO 453
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 453
atggaatact cuugguuaca uga                                          23

<210> SEQ ID NO 454
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 454
auggaatacu cutggutaca tga                                          23

<210> SEQ ID NO 455
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 455
ucuugguuac augaaauccc auc          23

<210> SEQ ID NO 456
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 456
auggaauacu cuugguuaca uga          23

<210> SEQ ID NO 457
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 457
auggaauacu cuugguuaca uga          23

<210> SEQ ID NO 458
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 458
ucuugguuac augaaauccc auc          23

<210> SEQ ID NO 459
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 459
auggaauacu cuugguuaca uga          23

<210> SEQ ID NO 460
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 460
ucuugguuac augaaauccc auc          23

<210> SEQ ID NO 461
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 461

-continued ucuugguuac augaaauccc auc                                                   23

<210> SEQ ID NO 462
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 462
ucuugguuac augaaauccc auc                                                   23

<210> SEQ ID NO 463
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 463
ucuugguuac augaaauccc auc                                                   23

<210> SEQ ID NO 464
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 464
auggaauacu cuugguuaca uga                                                   23

<210> SEQ ID NO 465
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 465
auggaauacu cuugguuaca uga                                                   23

<210> SEQ ID NO 466
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 466
auggaauacu cuugguuaca uga                                                   23

<210> SEQ ID NO 467
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 467
ucuugguuac augaaauccc auc                                                   23

```
<210> SEQ ID NO 468
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 468
auggaauacu cuugguuaca uga                                              23

<210> SEQ ID NO 469
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 469
auggaauacu cuugguuaca uga                                              23

<210> SEQ ID NO 470
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 470
auggaauacu cuugguuaca uga                                              23

<210> SEQ ID NO 471
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 471
auggaauacu cuugguuaca uga                                              23

<210> SEQ ID NO 472
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 472
ucuugguuac augaaauccc auc                                              23

<210> SEQ ID NO 473
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 473
auggaauacu cuugguuaca uga                                              23
```

```
<210> SEQ ID NO 474
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 474
auggaauacu cuugguuaca uga                                              23

<210> SEQ ID NO 475
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 475
ucuugguuac augaaauccc auc                                              23

<210> SEQ ID NO 476
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 476
auggaauact ctggtuaca uga                                               23

<210> SEQ ID NO 477
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 477
auggaauacu cuugguuaca uga                                              23

<210> SEQ ID NO 478
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 478
auggaauacu cuugguuaca uga                                              23

<210> SEQ ID NO 479
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 479
atggaauacu cuugguuaca uga                                              23

<210> SEQ ID NO 480
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 480
auggaatacu cuugguuaca uga                                              23

<210> SEQ ID NO 481
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 481
auggaauacu cuugguuaca uga                                              23

<210> SEQ ID NO 482
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 482
auggaauacu cuugguuaca uga                                              23

<210> SEQ ID NO 483
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 483
``` auggaauuact ctuggtuaca uga                                              23

<210> SEQ ID NO 484
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 484
auggaatacu cuugguuaca uga                                               23

<210> SEQ ID NO 485
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 485
atggaatact cuugguuaca tga                                               23

<210> SEQ ID NO 486
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 486
atggaauact cuugguuaca uga                                               23

<210> SEQ ID NO 487
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 487
auggaauacu cuugguuaca uga                                               23

<210> SEQ ID NO 488
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 488
atggaauact cutggutaca tga                                             23

<210> SEQ ID NO 489
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 489
atggaatacu cuugguuaca uga                                             23

<210> SEQ ID NO 490
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 490
auggaatacu cuugguuaca uga                                             23

<210> SEQ ID NO 491
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 491
atggaatacu cuugguuaca uga                                             23

<210> SEQ ID NO 492
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 492

```
auggaauacu cuugguuaca uga                                              23

<210> SEQ ID NO 493
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 493
auggaauacu cuugguuaca uga                                              23

<210> SEQ ID NO 494
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 494
auggaauacu cuugguuaca uga                                              23

<210> SEQ ID NO 495
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 495
auggaauacu cuugguuaca uga                                              23

<210> SEQ ID NO 496
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 496
ucuugguuac augaaauccc auc                                              23

<210> SEQ ID NO 497
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 497
auggaauacu cuugguuaca uga                                              23

<210> SEQ ID NO 498
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 498
auggaatacu cuugguuaca uga                                           23

<210> SEQ ID NO 499
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 499
auggaauacu cuugguuaca uga                                           23

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 500
auggaatacu cuugguuaca uga                                           23

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 501
auggaatacu cuugguuaca uga                                           23

<210> SEQ ID NO 502
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 502
auggaauacu cuugguuaca uga                                           23
```

```
<210> SEQ ID NO 503
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 503
auggaatacu cuugguuaca uga                                              23

<210> SEQ ID NO 504
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 504
auggaatacu cuugguuaca uga                                              23

<210> SEQ ID NO 505
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 505
auggaauacu cuugguuaca uga                                              23

<210> SEQ ID NO 506
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 506
atggaauacu cuugguuaca uga                                              23

<210> SEQ ID NO 507
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide
<220> FEATURE:
<223> OTHER INFORMATION: see specification as filed for detailed
      description of substitutions and preferred embodiments

<400> SEQUENCE: 507
auggaauacu cuuggutaca uga                                              23

<210> SEQ ID NO 508
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 508
atggaatacu cuugguuaca uga                                              23

<210> SEQ ID NO 509
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 509
auggaauacu cuugguuaca uga                                              23

<210> SEQ ID NO 510
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 510
auggaauacu cuugguuaca uga                                              23

<210> SEQ ID NO 511
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 511
auggaauacu cuugguuaca uga                                              23

<210> SEQ ID NO 512
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 512
auggaauacu cuugguuaca uga                                              23

<210> SEQ ID NO 513
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 513
auggaauacu cuugguuaca uga                                         23

<210> SEQ ID NO 514
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 514
auggaauacu cuugguuaca uga                                         23

<210> SEQ ID NO 515
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 515
auggaauacu cuugguuaca uga                                         23

<210> SEQ ID NO 516
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 516
auggaauacu cuugguuaca uga                                         23

<210> SEQ ID NO 517
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 517
auggaauacu cuugguuaca uga                                         23

<210> SEQ ID NO 518
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 518
auggaauacu cuugguuaca uga                                         23

<210> SEQ ID NO 519
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 519
auggaauacu cuugguuaca uga                                              23

<210> SEQ ID NO 520
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 520
auggaauacu cuugguuaca uga                                              23

<210> SEQ ID NO 521
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 521
auggaauacu cuugguuaca uga                                              23

<210> SEQ ID NO 522
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 522
auggaauacu cuugguuaca uga                                              23

<210> SEQ ID NO 523
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 523
auggaauacu cuugguuaca uga                                              23

<210> SEQ ID NO 524
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments -continued

<400> SEQUENCE: 524
auggaatacu cuugguuaca uga                                       23

<210> SEQ ID NO 525
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 525
auggaauacu cuugguuaca uga                                       23

<210> SEQ ID NO 526
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 526
auggaauacu cuugguuaca uga                                       23

<210> SEQ ID NO 527
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 527
auggaauacu ctugguuaca uga                                       23

<210> SEQ ID NO 528
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 528
auggaauacu cuugguuaca uga                                       23

<210> SEQ ID NO 529
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 529
auggaauacu cuugguuaca uga                                       23

<210> SEQ ID NO 530
<211> LENGTH: 23

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 530
auggaauacu cuugguuaca uga                                              23

<210> SEQ ID NO 531
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 531
auggaauacu cuugguuaca uga                                              23

<210> SEQ ID NO 532
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 532
auggaauacu cuugguuaca uga                                              23

<210> SEQ ID NO 533
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 533
auggaauacu cuugguuaca uga                                              23

<210> SEQ ID NO 534
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 534
auggaauacu cuugguuaca uga                                              23

<210> SEQ ID NO 535
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 535
auggaauacu cuugguuaca uga                                              23

<210> SEQ ID NO 536
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 536
auggaauacu cuugguuaca uga                                                 23

<210> SEQ ID NO 537
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 537
auggaauacu cuugguuaca uga                                                 23

<210> SEQ ID NO 538
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 538
auggaauacu cuugguuaca uga                                                 23

<210> SEQ ID NO 539
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 539
auggaauacu cuugguuaca uga                                                 23

<210> SEQ ID NO 540
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 540
auggaauacu cuugguuaca uga                                                 23

<210> SEQ ID NO 541
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

```
<223> OTHER INFORMATION: see specification as filed for detailed
      description of substitutions and preferred embodiments

<400> SEQUENCE: 541
atggaatacu cuugguuaca uga                                              23

<210> SEQ ID NO 542
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 542
auggaauacu cuugguuaca uga                                              23

<210> SEQ ID NO 543
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 543
auggaauacu cuugguuaca uga                                              23

<210> SEQ ID NO 544
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 544
auggaauacu cuugguuaca uga                                              23

<210> SEQ ID NO 545
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 545
auggaauacu cuugguuaca uga                                              23

<210> SEQ ID NO 546
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 546
auggaauacu cuugguuaca uga                                              23

<210> SEQ ID NO 547
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 547
auggaauacu cuugguuaca uga                                               23

<210> SEQ ID NO 548
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 548
auggaauacu cuugguuaca uga                                               23

<210> SEQ ID NO 549
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 549
auggaauacu cuugguuaca uga                                               23

<210> SEQ ID NO 550
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 550
auggaauacu cuugguuaca uga                                               23

<210> SEQ ID NO 551
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 551
auggaauacu cuugguuaca uga                                               23

<210> SEQ ID NO 552
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 552
auggaauacu cuugguuaca uga                                               23

<210> SEQ ID NO 553
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 553
auggaauacu cuugguuaca uga    23

<210> SEQ ID NO 554
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 554
auggaauacu cuugguuaca uga    23

<210> SEQ ID NO 555
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 555
auggaauacu cuugguuaca uga    23

<210> SEQ ID NO 556
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 556
auggaauacu cuugguuaca uga    23

<210> SEQ ID NO 557
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 557
auggaauacu cuugguuaca uga    23

<210> SEQ ID NO 558
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 558
auggaauacu cuugguuaca uga    23

<210> SEQ ID NO 559
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 559
auggaauacu cuugguuaca uga                                          23

<210> SEQ ID NO 560
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 560
auggaauacu cuugguuaca uga                                          23

<210> SEQ ID NO 561
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 561
auggaauacu cuugguuaca uga                                          23

<210> SEQ ID NO 562
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 562
auggaauacu cuugguuaca uga                                          23

<210> SEQ ID NO 563
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 563
auggaauacu cuugguuaca uga                                          23

<210> SEQ ID NO 564
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 564
auggaauacu cuugguuaca uga                                          23

<210> SEQ ID NO 565
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 565
```

```
auggaauacu cuugguuaca uga                                              23
```

<210> SEQ ID NO 566
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 566

```
auggaauacu cuugguuaca uga                                              23
```

<210> SEQ ID NO 567
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 567

```
auggaauacu cuugguuaca uga                                              23
```

<210> SEQ ID NO 568
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 568

```
auggaauacu cuugguuaca uga                                              23
```

<210> SEQ ID NO 569
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569

```
auggaauacu cuugguuaca uga                                              23
```

<210> SEQ ID NO 570
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570

```
auggaauacu cuugguuaca uga                                              23
```

<210> SEQ ID NO 571
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
auggaauacu cuugguuaca uga                                    23

<210> SEQ ID NO 572
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 572
auggaauacu cuugguuaca uga                                    23

<210> SEQ ID NO 573
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 573
auggaauacu cuugguuaca uga                                    23

<210> SEQ ID NO 574
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 574
auggaauacu cuugguuaca uga                                    23

<210> SEQ ID NO 575
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 575
auggaauacu cuugguuaca uga                                    23

<210> SEQ ID NO 576
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 576
auggaauacu cuugguuaca uga                                    23

<210> SEQ ID NO 577
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 577
auggaauacu cuugguuaca uga                                    23

<210> SEQ ID NO 578
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 578
auggaauacu cuugguuaca uga                                            23

<210> SEQ ID NO 579
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 579
ucuugguuac augaaauccc auc                                            23

<210> SEQ ID NO 580
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 580
ucuugguuac augaaauccc auc                                            23

<210> SEQ ID NO 581
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 581
ucuugguuac augaaauccc auc                                            23

<210> SEQ ID NO 582
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 582
ucuugguuac augaaauccc auc                                            23

<210> SEQ ID NO 583
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 583
ucuugguuac augaaauccc auc                                            23

-continued

<210> SEQ ID NO 584
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 584
ucuugguuac augaaauccc auc                                            23

<210> SEQ ID NO 585
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 585
ucuugguuac augaaauccc auc                                            23

<210> SEQ ID NO 586
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 586
ucuugguuac augaaauccc auc                                            23

<210> SEQ ID NO 587
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 587
auggaauacu cuugguuaca uga                                            23

<210> SEQ ID NO 588
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 588
auggaauacu cuugguuaca uga                                            23

<210> SEQ ID NO 589
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 589
auggaauacu cuugguuaca uga                                            23

-continued

```
<210> SEQ ID NO 590
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 590
auggaauacu cuugguuaca uga                                              23

<210> SEQ ID NO 591
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 591
auggaauacu cuugguuaca uga                                              23

<210> SEQ ID NO 592
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 592
auggaauacu cuugguuaca uga                                              23

<210> SEQ ID NO 593
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 593
auggaauacu cuugguuaca uga                                              23

<210> SEQ ID NO 594
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 594
auggaauacu cuugguuaca uga                                              23

<210> SEQ ID NO 595
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 595
auggaauacu cuugguuaca uga                                              23

<210> SEQ ID NO 596
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 596
auggaauacu cuugguuaca uga                                              23

<210> SEQ ID NO 597
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 597
auggaauacu cuugguuaca uga                                              23

<210> SEQ ID NO 598
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 598
auggaauacu cuugguuaca uga                                              23

<210> SEQ ID NO 599
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 599
auggaauacu cuugguuaca uga                                              23

<210> SEQ ID NO 600
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 600
auggaauacu cuugguuaca uga                                              23

<210> SEQ ID NO 601
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 601
auggaauacu cuugguuaca uga                                              23

<210> SEQ ID NO 602
<211> LENGTH: 23
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 602
auggaauacu cuugguuaca uga                                              23

<210> SEQ ID NO 603
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 603
auggaauacu cuugguuaca uga                                              23

<210> SEQ ID NO 604
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 604
auggaauacu cuugguuaca uga                                              23

<210> SEQ ID NO 605
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 605
auggaauacu cuugguuaca uga                                              23

<210> SEQ ID NO 606
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 606
auggaauacu cuugguuaca uga                                              23

<210> SEQ ID NO 607
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 607
auggaauacu cuugguuaca uga                                              23

<210> SEQ ID NO 608
<211> LENGTH: 23
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 608
auggaauacu cuugguuaca uga                                              23

<210> SEQ ID NO 609
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
auggaauacu cuugguuaca uga                                              23

<210> SEQ ID NO 610
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
auggaauacu cuugguuaca uga                                              23

<210> SEQ ID NO 611
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 611
auggaauacu cuugguuaca uga                                              23

<210> SEQ ID NO 612
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 612
auggaauacu cuugguuaca uga                                              23

<210> SEQ ID NO 613
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 613
auggaauacu cuugguuaca uga                                              23

<210> SEQ ID NO 614
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 614
auggaauacu cuugguuaca uga                                              23

<210> SEQ ID NO 615
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 615
auggaauacu cuugguuaca uga                                              23

<210> SEQ ID NO 616
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 616
auggaauacu cuuggutaca tga                                              23

<210> SEQ ID NO 617
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 617
auggaauacu cuugguuaca uga                                              23

<210> SEQ ID NO 618
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 618
auggaauacu cuugguuaca uga                                              23

<210> SEQ ID NO 619
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 619
auggaauacu cuugguuaca uga                                              23
```

```
<210> SEQ ID NO 620
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 620
auggaauacu cuugguuaca uga                                              23

<210> SEQ ID NO 621
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 621
auggaauacu cuugguuaca uga                                              23

<210> SEQ ID NO 622
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 622
auggaauacu cuugguuaca uga                                              23

<210> SEQ ID NO 623
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 623
auggaauacu cuugguuaca uga                                              23

<210> SEQ ID NO 624
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 624
auggaauacu cuugguuaca uga                                              23

<210> SEQ ID NO 625
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 625
auggaauacu cuugguuaca uga                                              23
```

```
<210> SEQ ID NO 626
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 626
auggaauacu cuugguuaca uga                                              23

<210> SEQ ID NO 627
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 627
auggaauacu cuugguuaca uga                                              23

<210> SEQ ID NO 628
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 628
auggaauacu cuugguuaca uga                                              23

<210> SEQ ID NO 629
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 629
atggaauacu cuugguuaca uga                                              23

<210> SEQ ID NO 630
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 630
auggaatacu cuugguuaca uga                                              23

<210> SEQ ID NO 631
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 631
atggaauacu cuugguuaca uga                                              23

<210> SEQ ID NO 632
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 632
atggaauact cuugguuaca uga                                              23

<210> SEQ ID NO 633
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 633
auggaauacu cuugguuaca uga                                              23

<210> SEQ ID NO 634
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 634
auggaauacu cuugguuaca uga                                              23

<210> SEQ ID NO 635
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
```

<223> OTHER INFORMATION: see specification as filed for detailed
      description of substitutions and preferred embodiments

<400> SEQUENCE: 635
auggaatacu cuugguuaca uga                                                    23

<210> SEQ ID NO 636
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 636
auggaatacu cuugguuaca uga                                                    23

<210> SEQ ID NO 637
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 637
auggaauacu cuuggutaca tga                                                    23

<210> SEQ ID NO 638
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 638
atggaauacu cuugguuaca uga                                                    23

<210> SEQ ID NO 639
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 639
auggaauacu cuugguuaca uga                                                    23

<210> SEQ ID NO 640

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 640
auggaauacu cuugguuaca uga                                                  23

<210> SEQ ID NO 641
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 641
auggaauacu cuugguuaca uga                                                  23

<210> SEQ ID NO 642
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 642
auggaauacu cuugguuaca uga                                                  23

<210> SEQ ID NO 643
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 643
auggaauacu cuugguuaca uga                                                  23

<210> SEQ ID NO 644
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 644
auggaauacu cuugguuaca uga                                                  23

<210> SEQ ID NO 645
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 645
```
auggaauacu cuugguuaca uga                                      23

<210> SEQ ID NO 646
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 646
auggaauacu cuugguuaca uga                                      23

<210> SEQ ID NO 647
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 647
auggaauacu cuugguuaca uga                                      23

<210> SEQ ID NO 648
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 648
auggaauacu cuugguuaca aga                                      23

<210> SEQ ID NO 649
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 649
auggaauacu cutgguuaca uga                                      23

<210> SEQ ID NO 650
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 650
auggaauacu cuugguuaca uga                                      23

<210> SEQ ID NO 651
<211> LENGTH: 23
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 651
auggaauacu ctugguuaca uga                                          23

<210> SEQ ID NO 652
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 652
auggaauacu cuugguuaca uga                                          23

<210> SEQ ID NO 653
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 653
auggaauacu cuugguuaca uga                                          23

<210> SEQ ID NO 654
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 654
auggaauacu cuugguuaca uga                                          23

<210> SEQ ID NO 655
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 655
auggaauacu cuugguuaca uga                                          23

<210> SEQ ID NO 656
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 656
auggaauacu cuugguuaca uga                                          23
```

<210> SEQ ID NO 657
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 657
auggaauacu cuugguuaca uga                                           23

<210> SEQ ID NO 658
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 658
auggaauacu cuugguuaca uga                                           23

<210> SEQ ID NO 659
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 659
auggaauacu cuugguuaca uga                                           23

<210> SEQ ID NO 660
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 660
auggaauacu cuugguuaca uga                                           23

<210> SEQ ID NO 661
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 661
auggaauacu cuugguuaca uga                                           23

<210> SEQ ID NO 662
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 662
auggaauacu cuugguuaca uga                                           23

```
<210> SEQ ID NO 663
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 663
auggaauacu cuugguuaca uga                                                 23

<210> SEQ ID NO 664
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 664
auggaauacu cuugguuaca uga                                                 23

<210> SEQ ID NO 665
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 665
auggaauacu cuugguuaca uga                                                 23

<210> SEQ ID NO 666
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 666
auggaauacu cuugguuaca uga                                                 23

<210> SEQ ID NO 667
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide
<220> FEATURE:
<223> OTHER INFORMATION: see specification as filed for detailed
      description of substitutions and preferred embodiments

<400> SEQUENCE: 667
auggaatacu cuugguuaca uga                                              23

<210> SEQ ID NO 668
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 668
auggaauacu cuugguuaca uga                                              23

<210> SEQ ID NO 669
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 669
auggaatacu cuugguuaca uga                                              23

<210> SEQ ID NO 670
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 670
auggaauacu cuugguuaca uga                                              23

<210> SEQ ID NO 671
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed -continued description of substitutions and preferred embodiments

<400> SEQUENCE: 671
auggaauacu cuugguuaca uga                                          23

<210> SEQ ID NO 672
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 672
atggaauacu cuugguuaca uga                                          23

<210> SEQ ID NO 673
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 673
tuauagagca agaacacugu uuu                                          23

<210> SEQ ID NO 674
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 674
uuauagagca agaacacugu uuu                                          23

<210> SEQ ID NO 675
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 675
uuauagagca agaacacugu uuu                                          23

<210> SEQ ID NO 676
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 676
uuauagagca agaacacugu uuu                                            23

<210> SEQ ID NO 677
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 677
uuauagagca agaacacugt t                                              21

<210> SEQ ID NO 678
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 678
uuauagagca agaacacugu uuu                                            23

<210> SEQ ID NO 679
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 679
uuauagagca agaacacugu uuu                                            23

<210> SEQ ID NO 680
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 680
uuauagagca agaacacugu uuu                                            23

<210> SEQ ID NO 681
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 681
uuauagagca agaacacugu uuu                                            23

<210> SEQ ID NO 682
<211> LENGTH: 23
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 682
uuauagagca agaacacugu uuu                                              23

<210> SEQ ID NO 683
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 683
uuauagagca agaacacugu uuu                                              23

<210> SEQ ID NO 684
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 684
uuauagagca agaacacugu uuu                                              23

<210> SEQ ID NO 685
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 685
uuauagagca agaacacugu uuu                                              23

<210> SEQ ID NO 686
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 686
uuauagagca agaacacugu uuu                                              23

<210> SEQ ID NO 687
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 687
uuauagagca agaacacugu uuu                                              23

<210> SEQ ID NO 688
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 688
uuauagagca agaacacugt t                                                21

<210> SEQ ID NO 689
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 689
uuauagagca agaacacugu uuu                                              23

<210> SEQ ID NO 690
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 690
uuauagagca agaacacugu uuu                                              23

<210> SEQ ID NO 691
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 691
uuauagagca agaacacugu uuu                                              23

<210> SEQ ID NO 692
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 692
tuauagagca agaacacagu uuu                                              23

<210> SEQ ID NO 693
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 693
uuauagagca agaacacugu uuu                                              23

<210> SEQ ID NO 694
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 694
uuauagagca agaacacugt t                                                21

<210> SEQ ID NO 695
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 695
uuauagagca agaacacugu uuu                                              23

<210> SEQ ID NO 696
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 696
uuauagagca agaacacugu uuu                                              23

<210> SEQ ID NO 697
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 697
uuauagagca agaacacugt t                                                21

<210> SEQ ID NO 698
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 698
uuauagagca agaacacugu uuu                                            23

<210> SEQ ID NO 699
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 699
uuauagagca agaacacugu uuu                                            23

<210> SEQ ID NO 700
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 700
uuauagagca agaacacugt t                                              21

<210> SEQ ID NO 701
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 701
uuauagagca agaacacugu uuu                                            23

<210> SEQ ID NO 702
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 702
uuauagagca agaacacugu uuu                                            23

<210> SEQ ID NO 703
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 703
uuauagagca agaacacugu uuu                                            23

<210> SEQ ID NO 704
<211> LENGTH: 21
<212> TYPE: DNA

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide
<220> FEATURE:
<223> OTHER INFORMATION: see specification as filed for detailed description of substitutions and preferred embodiments

<400> SEQUENCE: 704
uuauagagca agaacacugt t                                         21

<210> SEQ ID NO 705
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 705
uuauagagca agaacacugu uuu                                       23

<210> SEQ ID NO 706
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 706
uuauagagca agaacacugu uuu                                       23

<210> SEQ ID NO 707
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 707
uuauagagca agaacacugu uuu                                       23

<210> SEQ ID NO 708
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 708
uuauagagca agaacacugu uuu                                       23

<210> SEQ ID NO 709
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 709
uuauagagca agaacacugu uuu                                       23

```
<210> SEQ ID NO 710
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 710
uuauagagca agaacacugu uuu                                          23

<210> SEQ ID NO 711
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 711
uuauagagca agaacacugu uuu                                          23

<210> SEQ ID NO 712
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 712
uuauagagca agaacacugu uuu                                          23

<210> SEQ ID NO 713
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 713
uuauagagca agaacacugu uuu                                          23

<210> SEQ ID NO 714
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 714
uuauagagca agaacacugu uuu                                          23

<210> SEQ ID NO 715
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 715
uuauagagca agaacacugu uuu                                          23
```

<210> SEQ ID NO 716
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 716
uuauagagca agaacacugu uuu                                             23

<210> SEQ ID NO 717
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 717
uuauagagca agaacacugu uuu                                             23

<210> SEQ ID NO 718
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 718
uuauagagca agaacacugu uuu                                             23

<210> SEQ ID NO 719
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 719
uuauagagca agaacacugu uuu                                             23

<210> SEQ ID NO 720
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 720
uuauagagca agaacacugu uuu                                             23

<210> SEQ ID NO 721
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

```
<400> SEQUENCE: 721
ttauagagca agaacactgu ttu                                           23

<210> SEQ ID NO 722
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 722
uuauagagca agaacacugu uuu                                           23

<210> SEQ ID NO 723
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 723
uuauagagca agaacacugu uuu                                           23

<210> SEQ ID NO 724
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 724
uuauagagca agaacacugu uuu                                           23

<210> SEQ ID NO 725
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
uuauagagca agaacacugu uuu                                           23

<210> SEQ ID NO 726
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
uuauagagca agaacacugu uuu                                           23

<210> SEQ ID NO 727
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 727
uuauagagca agaacacugu uuu                                          23

<210> SEQ ID NO 728
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 728
uuauagagca agaacacugu uuu                                          23

<210> SEQ ID NO 729
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 729
uuauagagca agaacacugu uuu                                          23

<210> SEQ ID NO 730
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 730
utatagagca agaacacugt tuu                                          23

<210> SEQ ID NO 731
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 731
tuauagagca agaacacugu uuu                                          23

<210> SEQ ID NO 732
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<220> FEATURE:
<223> OTHER INFORMATION: see specification as filed for detailed
      description of substitutions and preferred embodiments

<400> SEQUENCE: 732
tuauagagca agaacacugu uuu                                              23

<210> SEQ ID NO 733
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 733
tuauagagca agaacacugu uuu                                              23

<210> SEQ ID NO 734
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 734
tuauagagca agaacacugu uuu                                              23

<210> SEQ ID NO 735
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 735
tuauagagca agaacacagu uuu                                              23

<210> SEQ ID NO 736
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments
```

<400> SEQUENCE: 736
ttatagagca agaacacagu uuu                                        23

<210> SEQ ID NO 737
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 737
tuauagagca agaacacugu uuu                                        23

<210> SEQ ID NO 738
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 738
uuauagagca agaacacugu uuu                                        23

<210> SEQ ID NO 739
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 739
uuauagagca agaacacugu uuu                                        23

<210> SEQ ID NO 740
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 740
uuauagagca agaacacugu uuu                                        23

<210> SEQ ID NO 741
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 741
uuauagagca agaacacugu uuu                                        23

<210> SEQ ID NO 742
<211> LENGTH: 23

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 742
uuauagagca agaacacugu uuu                                              23

<210> SEQ ID NO 743
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 743
uuauagagca agaacacugu uuu                                              23

<210> SEQ ID NO 744
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 744
uuauagagca agaacacugu uuu                                              23

<210> SEQ ID NO 745
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 745
uuauagagca agaacacugu uuu                                              23

<210> SEQ ID NO 746
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 746
uuauagagca agaacacugu uuu                                              23

<210> SEQ ID NO 747
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 747
uuauagagca agaacacugu uuu                                              23

<210> SEQ ID NO 748
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 748
uuauagagca agaacacugu uuu                                              23

<210> SEQ ID NO 749
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 749
uuauagagca agaacacugu uuu                                              23

<210> SEQ ID NO 750
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 750
uuauagagca agaacacugu uuu                                              23

<210> SEQ ID NO 751
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 751
uuauagagca agaacacugu uuu                                              23

<210> SEQ ID NO 752
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 752
uuauagagca agaacacugu uuu                                              23

<210> SEQ ID NO 753
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 753
uuauagagca agaacacugu uuu                                              23

<210> SEQ ID NO 754
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 754
uuauagagca agaacacugu uuu                                              23

<210> SEQ ID NO 755
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 755
uuauagagca agaacacugu uuu                                              23

<210> SEQ ID NO 756
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 756
uuauagagca agaacacugu uuu                                              23

<210> SEQ ID NO 757
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 757
uuauagagca agaacacugu uuu                                              23

<210> SEQ ID NO 758
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 758
uuauagagca agaacacugu uuu                                              23

<210> SEQ ID NO 759
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 759
uuauagagca agaacacugu uuu                                              23

<210> SEQ ID NO 760
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 760
uuauagagca agaacacugu uuu                                          23

<210> SEQ ID NO 761
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 761
uuauagagca agaacacugu uuu                                          23

<210> SEQ ID NO 762
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 762
uuauagagca agaacacugu uuu                                          23

<210> SEQ ID NO 763
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 763
uuauagagca agaacacugu uuu                                          23

<210> SEQ ID NO 764
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 764
uuauagagca agaacacugu uuu                                          23

<210> SEQ ID NO 765
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 765
uuauagagca agaacacugu uuu                                          23

<210> SEQ ID NO 766
<211> LENGTH: 23
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 766
uuauagagca agaacacugu uuu                                        23

<210> SEQ ID NO 767
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 767
uuauagagca agaacacugu uuu                                        23

<210> SEQ ID NO 768
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 768
uuauagagca agaacacugu uuu                                        23

<210> SEQ ID NO 769
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 769
uuauagagca agaacacugu uuu                                        23

<210> SEQ ID NO 770
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 770
uuauagagca agaacacugu uuu                                        23

<210> SEQ ID NO 771
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771
uuauagagca agaacacugu uuu                                        23

<210> SEQ ID NO 772
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 772
uuauagagca agaacacugu uuu                                      23

<210> SEQ ID NO 773
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 773
uuauagagca agaacacugu uuu                                      23

<210> SEQ ID NO 774
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 774
uuauagagca agaacacugu uuu                                      23

<210> SEQ ID NO 775
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 775
uuauagagca agaacacugu uuu                                      23

<210> SEQ ID NO 776
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 776
uuauagagca agaacacugu uuu                                      23

<210> SEQ ID NO 777
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 777
uuauagagca agaacacugu uuu                                      23

<210> SEQ ID NO 778
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 778
uuauagagca agaacacugu uuu                                           23

<210> SEQ ID NO 779
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 779
uuauagagca agaacacugu uuu                                           23

<210> SEQ ID NO 780
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 780
uuauagagca agaacacugu uuu                                           23

<210> SEQ ID NO 781
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 781
uuauagagca agaacacugu uuu                                           23

<210> SEQ ID NO 782
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 782
uuauagagca agaacacugu uuu                                           23

<210> SEQ ID NO 783
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 783
uuauagagca agaacacugu uuu                                           23

<210> SEQ ID NO 784
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 784
uuauagagca agaacacugu uuu 23

<210> SEQ ID NO 785
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 785
uuauagagca agaacacugu uuu 23

<210> SEQ ID NO 786
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 786
uuauagagca agaacacugu uuu 23

<210> SEQ ID NO 787
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 787
uuauagagca agaacacugu uuu 23

<210> SEQ ID NO 788
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 788
uuauagagca agaacacugu uuu 23

<210> SEQ ID NO 789
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 789
uuauagagca agaacacugu uuu 23

<210> SEQ ID NO 790
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 790
uuauagagca agaacacugu uuu                                                         23

<210> SEQ ID NO 791
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 791
uuauagagca agaacacugu uuu                                                         23

<210> SEQ ID NO 792
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 792
uuauagagca agaacacugu uuu                                                         23

<210> SEQ ID NO 793
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 793
uuauagagca agaacacugu uuu                                                         23

<210> SEQ ID NO 794
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 794
uuauagagca agaacacugu uuu                                                         23

<210> SEQ ID NO 795
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 795
uuauagagca agaacacugu uuu                                                         23

<210> SEQ ID NO 796
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 796
uuauagagca agaacacugu uuu                                                         23

<210> SEQ ID NO 797
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 797
uuauagagca agaacacugu uuu                                            23

<210> SEQ ID NO 798
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 798
uuauagagca agaacacugu uuu                                            23

<210> SEQ ID NO 799
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 799
uuauagagca agaacacugu uuu                                            23

<210> SEQ ID NO 800
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 800
uuauagagca agaacacugu uuu                                            23

<210> SEQ ID NO 801
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 801
uuauagagca agaacacugu uuu                                            23

<210> SEQ ID NO 802
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 802
uuauagagca agaacacugu uuu                                            23

<210> SEQ ID NO 803
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 803
uuauagagca agaacacugu uuu                                           23

<210> SEQ ID NO 804
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 804
uuauagagca agaacacugu uuu                                           23

<210> SEQ ID NO 805
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 805
uuauagagca agaacacugu uuu                                           23

<210> SEQ ID NO 806
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 806
uuauagagca agaacacugu uuu                                           23

<210> SEQ ID NO 807
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 807
uuauagagca agaacacugu uuu                                           23

<210> SEQ ID NO 808
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 808
uuauagagca agaacacugu uuu                                           23

-continued

```
<210> SEQ ID NO 809
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 809
uuauagagca agaacacugu uuu                                              23

<210> SEQ ID NO 810
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 810
uuauagagca agaacacugu uuu                                              23

<210> SEQ ID NO 811
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 811
uuauagagca agaacacugt tuu                                              23

<210> SEQ ID NO 812
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 812
uuauagagca agaacacugu uuu                                              23

<210> SEQ ID NO 813
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 813
uuauagagca agaacacugu uuu                                              23

<210> SEQ ID NO 814
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 814
uuauagagca agaacacugu uuu                                              23

<210> SEQ ID NO 815
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 815
uuauagagca agaacacugu uuu                                              23

<210> SEQ ID NO 816
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 816
uuauagagca agaacacugu tuu                                              23

<210> SEQ ID NO 817
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 817
uuauagagca agaacacugu uuu                                              23

<210> SEQ ID NO 818
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 818
uuauagagca agaacacugu uuu                                              23

<210> SEQ ID NO 819
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 819
uuauagagca agaacacugu uuu                                              23

<210> SEQ ID NO 820
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 820
uuauagagca agaacacugu uuu                                            23

<210> SEQ ID NO 821
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 821
uuauagagca agaacacugu uuu                                            23

<210> SEQ ID NO 822
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 822
uuatagagca agagcacagu uuu                                            23

<210> SEQ ID NO 823
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 823
uuauagagca agaacacugu uuu                                            23

<210> SEQ ID NO 824
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 824
utatagagca agaacactgt utu                                            23

<210> SEQ ID NO 825
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 825
uuauagagca agagcacagu uuu                                           23

<210> SEQ ID NO 826
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 826
uuauagagca agagcacagu uuu                                           23

<210> SEQ ID NO 827
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 827
uuauagagca agaacacugu uuu                                           23

<210> SEQ ID NO 828
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 828
utauagagca agagcacagu uuu                                           23

<210> SEQ ID NO 829
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 829
uuauagagca agaacacugu uuu                                           23

<210> SEQ ID NO 830
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 830
uuauagagca agaacacugu uuu                                              23

<210> SEQ ID NO 831
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 831
utauagagca agagcacagu uuu                                              23

<210> SEQ ID NO 832
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 832
uuauagagca agaacacugu uuu                                              23

<210> SEQ ID NO 833
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 833
utatagagca agaacacagu uuu                                              23

<210> SEQ ID NO 834
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 834
uuauagagca agaacacugu uuu                                              23

<210> SEQ ID NO 835
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 835
utatagagca agagcacagu uuu                                          23

<210> SEQ ID NO 836
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 836
uuauagagca agaacacugu uuu                                          23

<210> SEQ ID NO 837
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 837
utatagagca agaacacugt tuu                                          23

<210> SEQ ID NO 838
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 838
uuauagagca agaacacugu uuu                                          23

<210> SEQ ID NO 839
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 839
uuauagagca agaacacugu uuu                                          23

<210> SEQ ID NO 840
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 840
uuauagagca agaacacugu uuu                                             23

<210> SEQ ID NO 841
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 841
uuauagagca agaacacugu uuu                                             23

<210> SEQ ID NO 842
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 842
uuauagagca agaacacugu uuu                                             23

<210> SEQ ID NO 843
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 843
uuauagagca agaacacugu uuu                                             23

<210> SEQ ID NO 844
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 844
uuauagagca agaacacugu uuu                                             23

<210> SEQ ID NO 845
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 845
ucacaauuaa gcuccuucuu u                                               21

<210> SEQ ID NO 846
<211> LENGTH: 21
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 846
uuauuguucc ucuaguuauu u                                                 21

<210> SEQ ID NO 847
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 847
gcuauguuag acgauguaaa a                                                 21

<210> SEQ ID NO 848
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 848
ggacaugguc uuaaagacuu u                                                 21

<210> SEQ ID NO 849
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 849
caaaaacuca acauauuuga u                                                 21

<210> SEQ ID NO 850
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 850
accagugaaa ucaaagaaga a                                                 21

<210> SEQ ID NO 851
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 851
cacaauuaag cuccuucuuu u                                                 21

<210> SEQ ID NO 852
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 852
cuauguuaga cgauguaaaa a     21

<210> SEQ ID NO 853
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 853
ucaacauauu ugaucagucu u     21

<210> SEQ ID NO 854
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 854
aacugagaag aacuacauau a     21

<210> SEQ ID NO 855
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 855
acaauuaagc uccuucuuuu u     21

<210> SEQ ID NO 856
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 856
cuccagagcc aaaaucaaga u     21

<210> SEQ ID NO 857
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 857
cgauguaaaa auuuuagcca a     21

<210> SEQ ID NO 858
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 858
gucuuaaaga cuuuguccau a                                              21

<210> SEQ ID NO 859
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 859
caacauauuu gaucagucuu u                                              21

<210> SEQ ID NO 860
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 860
acugagaaga acuacauaua a                                              21

<210> SEQ ID NO 861
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 861
ccagagccaa aaucaagauu u                                              21

<210> SEQ ID NO 862
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 862
gauguaaaaa uuuuagccaa u                                              21

<210> SEQ ID NO 863
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 863
ucuuaaagac uuuguccaua a                                              21

<210> SEQ ID NO 864
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 864
```
aacauauuug aucagucuuu u        21

<210> SEQ ID NO 865
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 865
cugagaagaa cuacauauaa a        21

<210> SEQ ID NO 866
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 866
aauuaagcuc cuucuuuuua u        21

<210> SEQ ID NO 867
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 867
aaaucaagau uugcuauguu a        21

<210> SEQ ID NO 868
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 868
uucaguuggg acauggucuu a        21

<210> SEQ ID NO 869
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 869
gggccaaauu aaugacauau u        21

<210> SEQ ID NO 870
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 870

-continued acauauuuga ucagucuuuu u                                      21

<210> SEQ ID NO 871
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 871
agaacuacau auaaacuaca a                                      21

<210> SEQ ID NO 872
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 872
auuaagcucc uucuuuuuau u                                      21

<210> SEQ ID NO 873
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 873
agauuugcua uguuagacga u                                      21

<210> SEQ ID NO 874
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 874
ucaguuggga cauggucuua a                                      21

<210> SEQ ID NO 875
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 875
ggccaaauua augacauauu u                                      21

<210> SEQ ID NO 876
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 876
cauauuugau cagucuuuuu a                                      21

<210> SEQ ID NO 877
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 877
uacauauaaa cuacaaguca a                                              21

<210> SEQ ID NO 878
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 878
uuuuauuguu ccucuaguua u                                              21

<210> SEQ ID NO 879
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 879
uugcuauguu agacgaugua a                                              21

<210> SEQ ID NO 880
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 880
caguugggac auggucuuaa a                                              21

<210> SEQ ID NO 881
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 881
aaauuaauga cauauuucaa a                                              21

<210> SEQ ID NO 882
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 882
gaucagucuu uuuaugaucu a                                              21

```
<210> SEQ ID NO 883
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 883
acauauaaac uacaagucaa a                                              21

<210> SEQ ID NO 884
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 884
uuuauuguuc cucuaguuau u                                              21

<210> SEQ ID NO 885
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 885
ugcuauguua gacgauguaa a                                              21

<210> SEQ ID NO 886
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 886
gggacauggu cuuaaagacu u                                              21

<210> SEQ ID NO 887
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 887
ugacauauuu caaaaacuca a                                              21

<210> SEQ ID NO 888
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 888
aucagucuuu uuaugaucua u                                              21
```

<210> SEQ ID NO 889
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 889
cauauaaacu acaagucaaa a        21

<210> SEQ ID NO 890
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 890
cuugaacuca acucaaaacu u        21

<210> SEQ ID NO 891
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 891
cuacuucaac aaaaagugaa a        21

<210> SEQ ID NO 892
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 892
aagagcaacu aacuaacuua a        21

<210> SEQ ID NO 893
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 893
aaacaagaua auagcaucaa a        21

<210> SEQ ID NO 894
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 894
gcauagucaa auaaaagaaa u        21

<210> SEQ ID NO 895

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 895
auauaaacua caagucaaaa a                                              21

<210> SEQ ID NO 896
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 896
gaacucaacu caaaacuuga a                                              21

<210> SEQ ID NO 897
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 897
uacuucaaca aaagugaaa u                                               21

<210> SEQ ID NO 898
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 898
agagcaacua acuaacuuaa u                                              21

<210> SEQ ID NO 899
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 899
gauaauagca ucaaagaccu u                                              21

<210> SEQ ID NO 900
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 900
cauagucaaa uaaagaaau a                                               21

<210> SEQ ID NO 901
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 901
uauaaacuac aagucaaaaa u                                           21

<210> SEQ ID NO 902
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 902
aacucaacuc aaaacuugaa a                                           21

<210> SEQ ID NO 903
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 903
acuucaacaa aaagugaaau a                                           21

<210> SEQ ID NO 904
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 904
gagcaacuaa cuaacuuaau u                                           21

<210> SEQ ID NO 905
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 905
aaccaacagc auagucaaau a                                           21

<210> SEQ ID NO 906
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 906
agucaaauaa aagaaauaga a                                           21

<210> SEQ ID NO 907
<211> LENGTH: 21
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 907
agucaaaaau gaagagguaa a                                              21

<210> SEQ ID NO 908
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 908
cuugaaagcc uccagaaga a                                               21

<210> SEQ ID NO 909
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 909
cuucaacaaa aagugaaaua u                                              21

<210> SEQ ID NO 910
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 910
caacuaacua acuuaauuca a                                              21

<210> SEQ ID NO 911
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 911
accaacagca uagucaaaua a                                              21

<210> SEQ ID NO 912
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 912
gaacccacag aaauuucucu a                                              21

<210> SEQ ID NO 913
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 913
gaauauguca cuugaacuca a                                              21

<210> SEQ ID NO 914
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 914
ugaaagccuc cuagaagaaa a                                              21

<210> SEQ ID NO 915
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 915
uucaacaaaa agugaaauau u                                              21

<210> SEQ ID NO 916
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 916
aacuaacuaa cuuaauucaa a                                              21

<210> SEQ ID NO 917
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 917
ccaacagcau agucaaauaa a                                              21

<210> SEQ ID NO 918
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 918
aacccacaga aauuucucua u                                              21

<210> SEQ ID NO 919
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 919 ugcacuuga acucaacuca a                                                    21

<210> SEQ ID NO 920
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 920
gaaagccucc uagaagaaaa a                                                   21

<210> SEQ ID NO 921
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 921
aauauuuaga agagcaacua a                                                   21

<210> SEQ ID NO 922
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 922
acuaacuaac uuaauucaaa a                                                   21

<210> SEQ ID NO 923
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 923
caacagcaua gucaaauaaa a                                                   21

<210> SEQ ID NO 924
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 924
ccacagaaau uucucuaucu u                                                   21

<210> SEQ ID NO 925
<211> LENGTH: 21
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 925
gucacuugaa cucaacucaa a                                              21

<210> SEQ ID NO 926
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 926
cuccuagaag aaaaaauucu a                                              21

<210> SEQ ID NO 927
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 927
auuuagaaga gcaacuaacu a                                              21

<210> SEQ ID NO 928
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 928
cuaacuaacu uaauucaaaa u                                              21

<210> SEQ ID NO 929
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 929
cagcauaguc aaauaaaaga a                                              21

<210> SEQ ID NO 930
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 930
gaaauaagaa auguaaaaca u                                              21

<210> SEQ ID NO 931
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 931
ucacuugaac ucaacucaaa a                                              21

<210> SEQ ID NO 932
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 932
ucuacuucaa caaaaaguga a                                              21

<210> SEQ ID NO 933
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 933
uuuagaagag caacuaacua a                                              21

<210> SEQ ID NO 934
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 934
aaaacaagau aauagcauca a                                              21

<210> SEQ ID NO 935
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 935
agcauaguca aauaaaagaa a                                              21

<210> SEQ ID NO 936
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 936
agacccagca acucucaagu u                                              21

<210> SEQ ID NO 937
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 937
aguccaugga cauuaauuca a                                              21

<210> SEQ ID NO 938
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 938
gauggaucac aaaacuucaa u                                              21

<210> SEQ ID NO 939
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 939
cuagagaaga uauacuccau a                                              21

<210> SEQ ID NO 940
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 940
aaagacaaca aacauuauau u                                              21

<210> SEQ ID NO 941
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 941
cauuauauug aauauucuuu u                                              21

<210> SEQ ID NO 942
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 942
gacccagcaa cucucaaguu u                                              21

<210> SEQ ID NO 943
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 943
```
ggaucacaaa acuucaauga a                                              21

<210> SEQ ID NO 944
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 944
gaagauauac uccauaguga a                                              21

<210> SEQ ID NO 945
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 945
gacaacaaac auuauauuga a                                              21

<210> SEQ ID NO 946
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 946
gggaaaucac gaaaccaacu a                                              21

<210> SEQ ID NO 947
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 947
acccagcaac ucucaaguuu u                                              21

<210> SEQ ID NO 948
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 948
ggacauuaau ucaacaucga a                                              21

<210> SEQ ID NO 949
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 949

-continued gaucacaaaa cuucaaugaa a                                              21

<210> SEQ ID NO 950
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 950
acuccauagu gaagcaaucu a                                              21

<210> SEQ ID NO 951
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 951
acaacaaaca uuauauugaa u                                              21

<210> SEQ ID NO 952
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 952
ggaaaucacg aaaccaacua u                                              21

<210> SEQ ID NO 953
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 953
cccagcaacu cucaaguuuu u                                              21

<210> SEQ ID NO 954
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 954
gacauuaauu caacaucgaa u                                              21

<210> SEQ ID NO 955
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 955
aacgugggag aacuacaaau a                                              21

<210> SEQ ID NO 956
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 956
cuccauagug aagcaaucua a                                              21

<210> SEQ ID NO 957
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 957
caacaaacau uauauugaau a                                              21

<210> SEQ ID NO 958
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 958
gaaaucacga aaccaacuau a                                              21

<210> SEQ ID NO 959
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 959
cucucaaguu uuucaugucu a                                              21

<210> SEQ ID NO 960
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 960
acauuaauuc aacaucgaau a                                              21

<210> SEQ ID NO 961
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 961
gggagaacua caaauauggu u                                              21

<210> SEQ ID NO 962
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 962
uccauaguga agcaaucuaa u                                              21

<210> SEQ ID NO 963
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 963
aacaaacauu auauugaaua u                                              21

<210> SEQ ID NO 964
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 964
uggcaauguc cccaaugcaa u                                              21

<210> SEQ ID NO 965
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 965
ucagguaguc cauggacauu a                                              21

<210> SEQ ID NO 966
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 966
uuaauucaac aucgaauaga u                                              21

<210> SEQ ID NO 967
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 967
ggagaacuac aaauaugguu u                                              21

```
<210> SEQ ID NO 968
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 968
ccauagugaa gcaaucuaau u                                              21

<210> SEQ ID NO 969
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 969
acaaacauua uauugaauau u                                              21

<210> SEQ ID NO 970
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 970
aaugcaaucc cggaaaacaa a                                              21

<210> SEQ ID NO 971
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 971
cagguagucc auggacauua a                                              21

<210> SEQ ID NO 972
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 972
uucaacaucg aauagaugga u                                              21

<210> SEQ ID NO 973
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 973
guugggccua gagaagauau a                                              21

<210> SEQ ID NO 974
```

-continued

```
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 974
cauagugaag caaucuaauu a                                                   21

<210> SEQ ID NO 975
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 975
aacauuauau ugaauauucu u                                                   21

<210> SEQ ID NO 976
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 976
gcaaucccgg aaaacaaaga u                                                   21

<210> SEQ ID NO 977
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 977
gguaguccau ggacauuaau u                                                   21

<210> SEQ ID NO 978
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 978
aucgaauaga uggaucacaa a                                                   21

<210> SEQ ID NO 979
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 979
ccuagagaag auauacucca u                                                   21

<210> SEQ ID NO 980
<211> LENGTH: 21
```

-continued

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 980
guuggaagac uggaaagaca a                                              21

<210> SEQ ID NO 981
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 981
acauuauauu gaauauucuu u                                              21

<210> SEQ ID NO 982
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 982
caaucccgga aaacaaagau u                                              21

<210> SEQ ID NO 983
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 983
cuacuuggga ucacaaagca a                                              21

<210> SEQ ID NO 984
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 984
acaaccuaaa ugguaaauau a                                              21

<210> SEQ ID NO 985
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 985
auccauccaa cagauucaga a                                              21

<210> SEQ ID NO 986
<211> LENGTH: 21
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 986
aacugaggca aauuuaaaag a                                              21

<210> SEQ ID NO 987
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 987
agaguaugug uaaaaaucug u                                              21

<210> SEQ ID NO 988
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 988
aaucccggaa aacaaagauu u                                              21

<210> SEQ ID NO 989
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 989
uacuugggau cacaaagcaa a                                              21

<210> SEQ ID NO 990
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 990
caaccuaaau gguaaauaua a                                              21

<210> SEQ ID NO 991
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 991
uugaaugaac ugaggcaaau u                                              21

<210> SEQ ID NO 992
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 992
acugaggcaa auuuaaaagg a                                                  21

<210> SEQ ID NO 993
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 993
gaguaugugu aaaaucugu a                                                   21

<210> SEQ ID NO 994
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 994
acuugggauc acaaagcaaa a                                                  21

<210> SEQ ID NO 995
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 995
augguaaaua uaacaaacca a                                                  21

<210> SEQ ID NO 996
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 996
ugaaugaacu gaggcaaauu u                                                  21

<210> SEQ ID NO 997
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 997
cugaggcaaa uuuaaaaggc a                                                  21

<210> SEQ ID NO 998
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 998
aguaugugua aaaaucugua a                                              21

<210> SEQ ID NO 999
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 999
gaaaacaaag auuugguguu u                                              21

<210> SEQ ID NO 1000
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1000
aguguggaga aaacaaccua a                                              21

<210> SEQ ID NO 1001
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1001
gucucaaaau ggaagguuau a                                              21

<210> SEQ ID NO 1002
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1002
gaaugaacug aggcaaauuu a                                              21

<210> SEQ ID NO 1003
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1003
ugaggcaaau uuaaaaggca a                                              21

<210> SEQ ID NO 1004
<211> LENGTH: 21
<212> TYPE: RNA
<213> ORGANISM: Artificial Sequence
<220> FEATURE:
<223> OTHER INFORMATION: Description of Artificial Sequence: Synthetic
```

-continued oligonucleotide

<400> SEQUENCE: 1004
guauguguaa aaaucuguaa u                                            21

<210> SEQ ID NO 1005
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1005
aaaacaaaga uuugguguuu u                                            21

<210> SEQ ID NO 1006
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1006
guguggagaa aacaaccuaa a                                            21

<210> SEQ ID NO 1007
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1007
auggaagguu auacucuaua a                                            21

<210> SEQ ID NO 1008
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1008
aaugaacuga ggcaaauuua a                                            21

<210> SEQ ID NO 1009
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1009
gaggcaaauu uaaaaggcaa u                                            21

<210> SEQ ID NO 1010
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1010
uauguguaaa aaucuguaau a                                              21

<210> SEQ ID NO 1011
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1011
acaaagauuu gguguuuucu a                                              21

<210> SEQ ID NO 1012
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1012
uguggagaaa acaaccuaaa u                                              21

<210> SEQ ID NO 1013
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1013
uggaagguua uacucuauaa a                                              21

<210> SEQ ID NO 1014
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1014
augaacugag gcaaauuuaa a                                              21

<210> SEQ ID NO 1015
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1015
aggcaaauuu aaaaggcaau a                                              21

<210> SEQ ID NO 1016
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
```

```
<400> SEQUENCE: 1016
aagauuuggu guuucuacu u                                          21

<210> SEQ ID NO 1017
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1017
aaacaaccua aaugguaaau a                                         21

<210> SEQ ID NO 1018
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1018
auacucuaua aaaucaacca a                                         21

<210> SEQ ID NO 1019
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1019
ugaacugagg caaauuuaaa a                                         21

<210> SEQ ID NO 1020
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1020
ggcaaauuua aaaggcaaua a                                         21

<210> SEQ ID NO 1021
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1021
uuuucuacuu gggaucacaa a                                         21

<210> SEQ ID NO 1022
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1022
```
aacaaccuaa augguaaaua u                                            21

<210> SEQ ID NO 1023
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1023
uacucuauaa aaucaaccaa a                                            21

<210> SEQ ID NO 1024
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1024
gaacugaggc aaauuuaaaa a                                            21

<210> SEQ ID NO 1025
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1025
cagaguaugu guaaaaucu u                                             21

<210> SEQ ID NO 1026
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1026
aaagaaggag cuuaauugug aac                                          23

<210> SEQ ID NO 1027
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1027
aaauaacuag aggaacaaua aaa                                          23

<210> SEQ ID NO 1028
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1028

-continued uuuuacaucg ucuaacauag caa                                               23

<210> SEQ ID NO 1029
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1029
aaagucuuua agaccauguc cca                                               23

<210> SEQ ID NO 1030
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1030
aucaaauaug uugaguuuuu gaa                                               23

<210> SEQ ID NO 1031
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1031
uucuucuuug auuucacugg uuu                                               23

<210> SEQ ID NO 1032
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1032
aaaagaagga gcuuaauugu gaa                                               23

<210> SEQ ID NO 1033
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1033
uuuuuacauc gucuaacaua gca                                               23

<210> SEQ ID NO 1034
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1034
aagacugauc aaauauguug agu                                               23

<210> SEQ ID NO 1035
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1035
uauauguagu ucuucucagu ucc                                             23

<210> SEQ ID NO 1036
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1036
aaaaagaagg agcuuaauug uga                                             23

<210> SEQ ID NO 1037
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1037
aucuugauuu uggcucugga gau                                             23

<210> SEQ ID NO 1038
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1038
uuggcuaaaa uuuuuacauc guc                                             23

<210> SEQ ID NO 1039
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1039
uauggacaaa gucuuuaaga cca                                             23

<210> SEQ ID NO 1040
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1040
aaagacugau caaauauguu gag                                             23

<210> SEQ ID NO 1041
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1041
uuauauguag uucuucucag uuc                                          23

<210> SEQ ID NO 1042
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1042
aaaucuugau uuggcucug gag                                           23

<210> SEQ ID NO 1043
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1043
auuggcuaaa auuuuuacau cgu                                          23

<210> SEQ ID NO 1044
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1044
uuauggacaa agucuuuaag acc                                          23

<210> SEQ ID NO 1045
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1045
aaaagacuga ucaaauaugu uga                                          23

<210> SEQ ID NO 1046
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1046
uuuauaugua guucuucuca guu                                          23

```
<210> SEQ ID NO 1047
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1047
auaaaaagaa ggagcuuaau ugu                                            23

<210> SEQ ID NO 1048
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1048
uaacauagca aaucuugauu uug                                            23

<210> SEQ ID NO 1049
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1049
uaagaccaug ucccaacuga agg                                            23

<210> SEQ ID NO 1050
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1050
aauaugucau uaauuuggcc cuu                                            23

<210> SEQ ID NO 1051
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1051
aaaaagacug aucaaauaug uug                                            23

<210> SEQ ID NO 1052
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1052
uuguaguuua uauguaguuc uuc                                            23

<210> SEQ ID NO 1053
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1053
aauaaaaaga aggagcuuaa uug                                              23

<210> SEQ ID NO 1054
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1054
aucgucuaac auagcaaauc uug                                              23

<210> SEQ ID NO 1055
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1055
uuaagaccau gucccaacug aag                                              23

<210> SEQ ID NO 1056
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1056
aaauauguca uuaauuuggc ccu                                              23

<210> SEQ ID NO 1057
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1057
uaaaaagacu gaucaaauau guu                                              23

<210> SEQ ID NO 1058
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1058
uugacuugua guuuauaugu agu                                              23

<210> SEQ ID NO 1059
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1059
auaacuagag gaacaauaaa aag                                              23

<210> SEQ ID NO 1060
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1060
uuacaucguc uaacauagca aau                                              23

<210> SEQ ID NO 1061
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1061
uuuaagacca ugucccaacu gaa                                              23

<210> SEQ ID NO 1062
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1062
uuugaaauau gucauuaauu ugg                                              23

<210> SEQ ID NO 1063
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1063
uagaucauaa aaagacugau caa                                              23

<210> SEQ ID NO 1064
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1064
uuugacuugu aguuuauaug uag                                              23

<210> SEQ ID NO 1065
<211> LENGTH: 23
<212> TYPE: RNA
```

<213> ORGANISM: Artificial Sequence
<220> FEATURE:
<223> OTHER INFORMATION: Description of Artificial Sequence: Synthetic oligonucleotide

<400> SEQUENCE: 1065
aauaacuaga ggaacaauaa aaa					23

<210> SEQ ID NO 1066
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1066
uuuacaucgu cuaacauagc aaa					23

<210> SEQ ID NO 1067
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1067
aagucuuuaa gaccaugucc caa					23

<210> SEQ ID NO 1068
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1068
uugaguuuuu gaaauauguc auu					23

<210> SEQ ID NO 1069
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1069
auagaucaua aaaagacuga uca					23

<210> SEQ ID NO 1070
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 1070
uuuugacuug uaguuuauau gua					23

<210> SEQ ID NO 1071
<211> LENGTH: 23
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 1071
aaguuuugag uugaguucaa gug                                              23

<210> SEQ ID NO 1072
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1072
uuucacuuuu uguugaagua gaa                                              23

<210> SEQ ID NO 1073
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1073
uuaaguuagu uaguugcucu ucu                                              23

<210> SEQ ID NO 1074
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1074
uuugaugcua uuaucuuguu uuu                                              23

<210> SEQ ID NO 1075
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1075
auuucuuuua uuugacuaug cug                                              23

<210> SEQ ID NO 1076
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1076
uuuuugacuu guaguuuaua ugu                                              23

<210> SEQ ID NO 1077
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1077
uucaaguuuu gaguugaguu caa                                             23

<210> SEQ ID NO 1078
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1078
auuucacuuu uuguugaagu aga                                             23

<210> SEQ ID NO 1079
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1079
auuaaguuag uuaguugcuc uuc                                             23

<210> SEQ ID NO 1080
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1080
aaggucuuug augcuauuau cuu                                             23

<210> SEQ ID NO 1081
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1081
uauuucuuuu auuugacuau gcu                                             23

<210> SEQ ID NO 1082
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1082
auuuuugacu uguaguuuau aug                                             23

<210> SEQ ID NO 1083
<211> LENGTH: 23
<212> TYPE: RNA
<213> ORGANISM: Artificial Sequence
<220> FEATURE:
<223> OTHER INFORMATION: Description of Artificial Sequence: Synthetic
```

```
                              oligonucleotide

<400> SEQUENCE: 1083
uuucaaguuu ugaguugagu uca                                              23

<210> SEQ ID NO 1084
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1084
uauuucacuu uuuguugaag uag                                              23

<210> SEQ ID NO 1085
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1085
aauuaaguua guuaguugcu cuu                                              23

<210> SEQ ID NO 1086
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1086
uauuugacua ugcuguuggu uua                                              23

<210> SEQ ID NO 1087
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1087
uucuauuucu uuuauuugac uau                                              23

<210> SEQ ID NO 1088
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1088
uuuaccucuu cauuuugac uug                                               23

<210> SEQ ID NO 1089
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 1089
uucuucuagg aggcuuucaa guu                                              23

<210> SEQ ID NO 1090
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1090
auauuucacu uuuguugaa gua                                               23

<210> SEQ ID NO 1091
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1091
uugaauuaag uuaguuaguu gcu                                              23

<210> SEQ ID NO 1092
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1092
uuauuugacu augcuguugg uuu                                              23

<210> SEQ ID NO 1093
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1093
uagagaaauu ucuguggguu cuu                                              23

<210> SEQ ID NO 1094
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1094
uugaguucaa gugacauauu cuu                                              23

<210> SEQ ID NO 1095
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1095 uuucuucua ggaggcuuuc aag       23

<210> SEQ ID NO 1096
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1096
aauauuucac uuuuuguuga agu       23

<210> SEQ ID NO 1097
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1097
uuugaauuaa guuaguuagu ugc       23

<210> SEQ ID NO 1098
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1098
uuuauuugac uaugcuguug guu       23

<210> SEQ ID NO 1099
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1099
auagagaaau uucugugggu ucu       23

<210> SEQ ID NO 1100
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1100
uugaguugag uucaagugac aua       23

<210> SEQ ID NO 1101
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1101
uuuuucuucu aggaggcuuu caa                                              23

<210> SEQ ID NO 1102
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1102
uuaguugcuc uucuaaauau uuc                                              23

<210> SEQ ID NO 1103
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1103
uuuugaauua aguaguuag uug                                               23

<210> SEQ ID NO 1104
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1104
uuuuauuuga cuaugcuguu ggu                                              23

<210> SEQ ID NO 1105
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1105
aagauagaga aauuucugug ggu                                              23

<210> SEQ ID NO 1106
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1106
uuugaguuga guucaaguga cau                                              23

<210> SEQ ID NO 1107
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1107

```
uagaauuuuu ucuucuagga ggc                                              23
```

<210> SEQ ID NO 1108
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1108

```
uaguuaguug cucuucuaaa uau                                              23
```

<210> SEQ ID NO 1109
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1109

```
auuuugaauu aaguuaguua guu                                              23
```

<210> SEQ ID NO 1110
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1110

```
uucuuuuauu ugacuaugcu guu                                              23
```

<210> SEQ ID NO 1111
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1111

```
auguuuuaca uuucuuauuu cau                                              23
```

<210> SEQ ID NO 1112
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1112

```
uuuugaguug aguucaagug aca                                              23
```

<210> SEQ ID NO 1113
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1113

```
uucacuuuuu guugaaguag aau                                              23
```

<210> SEQ ID NO 1114
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1114
uuaguuaguu gcucuucuaa aua                                                23

<210> SEQ ID NO 1115
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1115
uugaugcuau uaucuuguuu uuc                                                23

<210> SEQ ID NO 1116
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1116
uuucuuuuau uugacuaugc ugu                                                23

<210> SEQ ID NO 1117
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1117
aacuugagag uugcuggguc uga                                                23

<210> SEQ ID NO 1118
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1118
uugaauuaau guccauggac uac                                                23

<210> SEQ ID NO 1119
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1119
auugaaguuu ugugauccau cua                                                23

```
<210> SEQ ID NO 1120
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1120
uauggaguau aucuucucua ggc                                              23

<210> SEQ ID NO 1121
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1121
aauauaaugu uuguugucuu ucc                                              23

<210> SEQ ID NO 1122
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1122
aaaagaauau ucaauauaau guu                                              23

<210> SEQ ID NO 1123
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1123
aaacuugaga guugcugggu cug                                              23

<210> SEQ ID NO 1124
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1124
uucauugaag uuuugugauc cau                                              23

<210> SEQ ID NO 1125
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1125
uucacuaugg aguauaucuu cuc                                              23
```

```
<210> SEQ ID NO 1126
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1126
uucaauauaa uguuuguugu cuu                                              23

<210> SEQ ID NO 1127
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1127
uaguugguuu cgugauuucc caa                                              23

<210> SEQ ID NO 1128
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1128
aaaacuugag aguugcuggg ucu                                              23

<210> SEQ ID NO 1129
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1129
uucgauguug aauuaauguc cau                                              23

<210> SEQ ID NO 1130
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1130
uuucauugaa guuuugugau cca                                              23

<210> SEQ ID NO 1131
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1131
uagauugcuu cacuauggag uau                                              23

<210> SEQ ID NO 1132
```

```
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1132
auucaauaua auguuguug ucu                                              23

<210> SEQ ID NO 1133
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1133
auaguugguu ucgugauuuc cca                                             23

<210> SEQ ID NO 1134
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1134
aaaaacuuga gaguugcugg guc                                             23

<210> SEQ ID NO 1135
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1135
auucgauguu gaauuaaugu cca                                             23

<210> SEQ ID NO 1136
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1136
uauuuguagu ucucccacgu uuc                                             23

<210> SEQ ID NO 1137
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1137
uuagauugcu ucacuaugga gua                                             23

<210> SEQ ID NO 1138
<211> LENGTH: 23
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1138
uauucaauau aauguuuguu guc                                             23

<210> SEQ ID NO 1139
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1139
uauaguuggu uucgugauuu ccc                                             23

<210> SEQ ID NO 1140
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1140
uagacaugaa aaacuugaga guu                                             23

<210> SEQ ID NO 1141
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1141
uauucgaugu ugaauuaaug ucc                                             23

<210> SEQ ID NO 1142
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1142
aaccauauuu guaguucucc cac                                             23

<210> SEQ ID NO 1143
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1143
auuagauugc uucacuaugg agu                                             23

<210> SEQ ID NO 1144
<211> LENGTH: 23
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1144
auauucaaua uaauguuugu ugu                                            23

<210> SEQ ID NO 1145
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1145
auugcauugg ggacauugcc agu                                            23

<210> SEQ ID NO 1146
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1146
uaauguccau ggacuaccug aua                                            23

<210> SEQ ID NO 1147
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1147
aucuauucga uguugaauua aug                                            23

<210> SEQ ID NO 1148
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1148
aaaccauauu uguaguucuc cca                                            23

<210> SEQ ID NO 1149
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1149
aauuagauug cuucacuaug gag                                            23

<210> SEQ ID NO 1150
<211> LENGTH: 23
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1150
aauauucaau auaauguuug uug                                          23

<210> SEQ ID NO 1151
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1151
uuuguuuucc gggauugcau ugg                                          23

<210> SEQ ID NO 1152
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1152
uuaaugucca uggacuaccu gau                                          23

<210> SEQ ID NO 1153
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1153
auccaucuau ucgauguuga auu                                          23

<210> SEQ ID NO 1154
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1154
uauaucuucu cuaggcccaa cca                                          23

<210> SEQ ID NO 1155
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1155
uaauuagauu gcuucacuau gga                                          23

<210> SEQ ID NO 1156
<211> LENGTH: 23
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 1156
aagaauauuc aauauaaugu uug                                              23

<210> SEQ ID NO 1157
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1157
aucuuuguuu uccgggauug cau                                              23

<210> SEQ ID NO 1158
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1158
aauuaauguc cauggacuac cug                                              23

<210> SEQ ID NO 1159
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1159
uuugugaucc aucuauucga ugu                                              23

<210> SEQ ID NO 1160
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1160
auggaguaua ucuucucuag gcc                                              23

<210> SEQ ID NO 1161
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1161
uugucuuucc agucuuccaa cuc                                              23

<210> SEQ ID NO 1162
<211> LENGTH: 23
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 1162
aaagaauauu caauauaaug uuu                                              23

<210> SEQ ID NO 1163
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1163
aaucuuuguu uuccgggauu gca                                              23

<210> SEQ ID NO 1164
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1164
uugcuuugug aucccaagua gaa                                              23

<210> SEQ ID NO 1165
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1165
uauauuuacc auuuagguug uuu                                              23

<210> SEQ ID NO 1166
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1166
uucugaaucu guuggaugga uca                                              23

<210> SEQ ID NO 1167
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1167
ucuuuuaaau uugccucagu uca                                              23

<210> SEQ ID NO 1168
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1168
acagauuuuu acacauacuc ugu                                          23

<210> SEQ ID NO 1169
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1169
aaaucuuugu uuccgggau ugc                                           23

<210> SEQ ID NO 1170
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1170
uuugcuuugu gaucccaagu aga                                          23

<210> SEQ ID NO 1171
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1171
uuauauuuac cauuuagguu guu                                          23

<210> SEQ ID NO 1172
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1172
aauuugccuc aguucauuca aag                                          23

<210> SEQ ID NO 1173
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1173
uccuuuuaaa uuugccucag uuc                                          23

<210> SEQ ID NO 1174
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1174
uacagauuuu uacacauacu cug                                          23

<210> SEQ ID NO 1175
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1175
uuuugcuuug ugaucccaag uag                                          23

<210> SEQ ID NO 1176
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1176
uugguuuguu auauuuacca uuu                                          23

<210> SEQ ID NO 1177
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1177
aaauuugccu caguucauuc aaa                                          23

<210> SEQ ID NO 1178
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1178
ugccuuuuaa auuugccuca guu                                          23

<210> SEQ ID NO 1179
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1179
uuacagauuu uuacacauac ucu                                          23

<210> SEQ ID NO 1180
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1180
```
aaacaccaaa ucuuuguuuu ccg                                          23

<210> SEQ ID NO 1181
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1181
uuagguuguu uucuccacac uca                                          23

<210> SEQ ID NO 1182
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1182
uauaaccuuc cauuuugaga cuu                                          23

<210> SEQ ID NO 1183
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1183
uaaauuugcc ucaguucauu caa                                          23

<210> SEQ ID NO 1184
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1184
uugccuuuua aauuugccuc agu                                          23

<210> SEQ ID NO 1185
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1185
auuacagauu uuuacacaua cuc                                          23

<210> SEQ ID NO 1186
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1186
aaaacaccaa aucuuuguuu ucc                                              23

<210> SEQ ID NO 1187
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1187
uuuagguugu uuucuccaca cuc                                              23

<210> SEQ ID NO 1188
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1188
uuauagagua uaaccuucca uuu                                              23

<210> SEQ ID NO 1189
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1189
uuaaauuugc cucaguucau uca                                              23

<210> SEQ ID NO 1190
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1190
auugccuuuu aaauuugccu cag                                              23

<210> SEQ ID NO 1191
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1191
uauuacagau uuuuacacau acu                                              23

<210> SEQ ID NO 1192
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1192
uagaaaacac caaaucuuug uuu                                              23

<210> SEQ ID NO 1193
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1193
auuuagguug uuucuccac acu                                              23

<210> SEQ ID NO 1194
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1194
uuuauagagu auaaccuucc auu                                             23

<210> SEQ ID NO 1195
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1195
uuuaaauuug ccucaguuca uuc                                             23

<210> SEQ ID NO 1196
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1196
uauugccuuu uaaauuugcc uca                                             23

<210> SEQ ID NO 1197
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1197
aaguagaaaa caccaaaucu uug                                             23

<210> SEQ ID NO 1198
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1198
uauuuaccau uuagguuguu uuc                                             23

```
<210> SEQ ID NO 1199
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1199
uugguugauu uuauagagua uaa                                             23

<210> SEQ ID NO 1200
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1200
uuuuaaauuu gccucaguuc auu                                             23

<210> SEQ ID NO 1201
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1201
uuauugccuu uuaaauuugc cuc                                             23

<210> SEQ ID NO 1202
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1202
uuugugaucc caaguagaaa aca                                             23

<210> SEQ ID NO 1203
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1203
auauuuacca uuuagguugu uuu                                             23

<210> SEQ ID NO 1204
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1204
uuugguugau uuuauagagu aua                                             23
```

-continued

```
<210> SEQ ID NO 1205
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1205
uuuuuaaauu ugccucaguu cau                                            23

<210> SEQ ID NO 1206
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1206
aagauuuuua cacauacucu gug                                            23

<210> SEQ ID NO 1207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 1207
cuuacgcuga guacuucgat t                                              21

<210> SEQ ID NO 1208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: see specification as filed for detailed
      description of substitutions and preferred embodiments

<400> SEQUENCE: 1208
ucgaaguacu cagcguaagt t                                              21
```

MODIFIED RNAi AGENTS

RELATED APPLICATION

This application is a continuation of U.S. patent application Ser. No. 16/850,555, filed Apr. 16, 2020, which is a continuation of U.S. patent application Ser. No. 16/165,343, filed Oct. 19, 2018, now U.S. Pat. No. 10,688,170, which is a continuation of U.S. patent application Ser. No. 15/706,389, filed Sep. 15, 2017, which is a continuation of U.S. patent application Ser. No. 14/358,009, filed May 13, 2014, now U.S. Pat. No. 9,796,974, which claims priority to PCT Application No. PCT/US2012/065601, filed Nov. 16, 2012, which claims benefit of priority to U.S. Provisional Application No. 61/561,710, filed on Nov. 18, 2011; all of which are herein incorporated by reference in their entirety.

SEQUENCE LISTING

The instant application contains a Sequence Listing which has been submitted via the USPTO patent electronic filing system in ASCII format and is hereby incorporated by reference in its entirety. Said ASCII copy, created on May 13, 2014, is named 29520_1082_ALN_158US_Sequence_Listing and is 315,935 bytes in size.

FIELD OF THE INVENTION

The invention relates to RNAi duplex agents having particular motifs that are advantageous for inhibition of target gene expression, as well as RNAi compositions suitable for therapeutic use. Additionally, the invention provides methods of inhibiting the expression of a target gene by administering these RNAi duplex agents, e.g., for the treatment of various diseases.

BACKGROUND

RNA interference or "RNAi" is a term initially coined by Fire and co-workers to describe the observation that double-stranded RNA (dsRNA) can block gene expression (Fire et al. (1998) Nature 391, 806-811; Elbashir et al. (2001) Genes Dev. 15, 188-200). Short dsRNA directs gene-specific, post-transcriptional silencing in many organisms, including vertebrates, and has provided a new tool for studying gene function. RNAi is mediated by RNA-induced silencing complex (RISC), a sequence-specific, multi-component nuclease that destroys messenger RNAs homologous to the silencing trigger. RISC is known to contain short RNAs (approximately 22 nucleotides) derived from the double-stranded RNA trigger, but the protein components of this activity remained unknown.

Double-stranded RNA (dsRNA) molecules with good gene-silencing properties are needed for drug development based on RNA interference (RNAi). An initial step in RNAi is the activation of the RNA induced silencing complex (RISC), which requires degradation of the sense strand of the dsRNA duplex. Sense strand was known to act as the first RISC substrate that is cleaved by Argonaute 2 in the middle of the duplex region. Immediately after the cleaved 5'-end and 3'-end fragments of the sense strand are removed from the endonuclease Ago2, the RISC becomes activated by the antisense strand (Rand et al. (2005) Cell 123, 621).

It was believed that when the cleavage of the sense strand is inhibited, the endonucleolytic cleavage of target mRNA is impaired (Leuschner et al. (2006) EMBO Rep., 7, 314; Rand et al. (2005) Cell 123, 621; Schwarz et al. (2004) Curr. Biol. 14, 787). Leuschner et al. showed that incorporation of a 2'-O-Me ribose to the Ago2 cleavage site in the sense strand inhibits RNAi in HeLa cells (Leuschner et al. (2006) EMBO Rep., 7, 314). A similar effect was observed with phosphorothioate modifications, showing that cleavage of the sense strand was required for efficient RNAi also in mammals.

Morrissey et al. used a siRNA duplex containing 2'-F modified residues, among other sites and modifications, also at the Ago2 cleavage site, and obtained compatible silencing compared to the unmodified siRNAs (Morrissey et al. (2005) Hepatology 41, 1349). However, Morrissey's modification is not motif specific, e.g., one modification includes 2'-F modifications on all pyrimidines on both sense and antisense strands as long as pyrimidine residue is present, without any selectivity; and hence it is uncertain, based on these teachings, if specific motif modification at the cleavage site of sense strand can have any actual effect on gene silencing activity.

Muhonen et al. used a siRNA duplex containing two 2'-F modified residues at the Ago2 cleavage site on the sense or antisense strand and found it was tolerated (Muhonen et al. (2007) Chemistry & Biodiversity 4, 858-873). However, Muhonen's modification is also sequence specific, e.g., for each particular strand, Muhonen only modifies either all pyrimidines or all purines, without any selectivity.

Choung et al. used a siRNA duplex containing alternative modifications by 2'-OMe or various combinations of 2'-F, 2'-OMe and phosphorothioate modifications to stabilize siRNA in serum to Sur10058 (Choung et al. (2006) Biochemical and Biophysical Research Communications 342, 919-927). Choung suggested that the residues at the cleavage site of the antisense strand should not be modified with 2'-OMe in order to increase the stability of the siRNA.

There is thus an ongoing need for iRNA duplex agents to improve the gene silencing efficacy of siRNA gene therapeutics. This invention is directed to that need.

SUMMARY

This invention provides effective nucleotide or chemical motifs for dsRNA agents optionally conjugated to at least one ligand, which are advantageous for inhibition of target gene expression, as well as RNAi compositions suitable for therapeutic use.

The inventors surprisingly discovered that introducing one or more motifs of three identical modifications on three consecutive nucleotides at or near the cleavage site of a dsRNA agent that is comprised of modified sense and antisense strands enhances the gene silencing activity of the dsRNA agent.

In one aspect, the invention relates to a double-stranded RNAi (dsRNA) agent capable of inhibiting the expression of a target gene. The dsRNA agent comprises a sense strand and an antisense strand, each strand having 14 to 30 nucleotides. The dsRNA duplex is represented by formula (III):

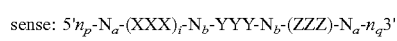

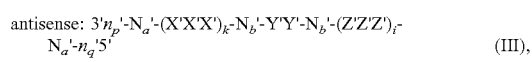

(III),

In formula (III), i, j, k, and l are each independently 0 or 1; p and q are each independently 0-6; n represents a nucleotide; each $N_a$ and $N_a'$ independently represents an oligonucleotide sequence comprising 0-25 nucleotides which are either modified or unmodified or combinations thereof, each sequence comprising at least two differently modified nucleotides; each $N_b$ and $N_b'$ independently represents an oligonucleotide sequence comprising 0-10 nucleotides which are either modified or unmodified or combinations thereof, each $n_p$ and $n_q$ independently represents an overhang nucleotide sequence comprising 0-6 nucleotides; and XXX, YYY, ZZZ, X'X'X', Y'Y'Y', and Z'Z'Z' each independently represent one motif of three identical modifications on three consecutive nucleotides; wherein the modifications on Nb is different than the modification on Y and the modifications on Nb' is different than the modification on Y'. At least one of the Y nucleotides forms a base pair with its complementary Y' nucleotides, and wherein the modification on the Y nucleotide is different than the modification on the Y' nucleotide.

Each $n_p$ and $n_q$ independently represents an overhang nucleotide sequence comprising 0-6 nucleotides; each n and n' represents an overhang nucleotide; and p and q are each independently 0-6.

In another aspect, the invention relates to a dsRNA agent capable of inhibiting the expression of a target gene. The dsRNA agent comprises a sense strand and an antisense strand, each strand having 14 to 30 nucleotides. The sense strand contains at least two motifs of three identical modifications on three consecutive nucleotides, where at least one of the motifs occurs at or near the cleavage site within the strand and at least one of the motifs occurs at another portion of the strand that is separated from the motif at the cleavage site by at least one nucleotide. The antisense strand contains at least one motif of three identical modifications on three consecutive nucleotides, where at least one of the motifs occurs at or near the cleavage site within the strand and at least one of the motifs occurs at another portion of the strand that is separated from the motif at or near cleavage site by at least one nucleotide. The modification in the motif occurring at or near the cleavage site in the sense strand is different than the modification in the motif occurring at or near the cleavage site in the antisense strand.

In another aspect, the invention relates to a dsRNA agent capable of inhibiting the expression of a target gene. The dsRNA agent comprises a sense strand and an antisense strand, each strand having 14 to 30 nucleotides. The sense strand contains at least one motif of three 2'-F modifications on three consecutive nucleotides, where at least one of the motifs occurs at or near the cleavage site in the strand. The antisense strand contains at least one motif of three 2'-O-methyl modifications on three consecutive nucleotides at or near the cleavage site.

In another aspect, the invention relates to a dsRNA agent capable of inhibiting the expression of a target gene. The dsRNA agent comprises a sense strand and an antisense strand, each strand having 14 to 30 nucleotides. The sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In another aspect, the invention further provides a method for delivering the dsRNA to a specific target in a subject by subcutaneous or intravenenuous administration.

DETAILED DESCRIPTION

A superior result may be obtained by introducing one or more motifs of three identical modifications on three consecutive nucleotides into a sense strand and/or antisense strand of a dsRNA agent, particularly at or near the cleavage site. The sense strand and antisense strand of the dsRNA agent may otherwise be completely modified. The introduction of these motifs interrupts the modification pattern, if present, of the sense and/or antisense strand. The dsRNA agent optionally conjugates with a GalNAc derivative ligand, for instance on the sense strand. The resulting dsRNA agents present superior gene silencing activity.

The inventors surprisingly discovered that having one or more motifs of three identical modifications on three consecutive nucleotides at or near the cleavage site of at least one strand of a dsRNA agent superiorly enhanced the gene silencing activity of the dsRNA agent.

Accordingly, the invention provides a double-stranded RNAi (dsRNA) agent capable of inhibiting the expression of a target gene. The dsRNA agent comprises a sense strand and an antisense strand. Each strand of the dsRNA agent can range from 12-30 nucleotides in length. For example, each strand can be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex dsRNA. The duplex region of a dsRNA agent may be 12-30 nucleotide pairs in length. For example, the duplex region can be between 14-30 nucleotide pairs in length, 17-30 nucleotide pairs in length, 25-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27.

In one embodiment, the dsRNA agent of the invention comprises may contain one or more overhang regions and/or capping groups of dsRNA agent at the 3'-end, or 5'-end or both ends of a strand. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be other sequence. The first and second strands can also be joined, e.g., by additional bases to form a hairpin, or by other non-base linkers.

In one embodiment, the nucleotides in the overhang region of the dsRNA agent of the invention can each independently be a modified or unmodified nucleotide including, but no limited to 2'-sugar modified, such as, 2-F 2'-Omethyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be other sequence.

The 5'- or 3'-overhangs at the sense strand, antisense strand or both strands of the dsRNA agent of the invention may be phosphorylated. In some embodiments, the overhang region contains two nucleotides having a phosphorothioate between the two nucleotides, where the two nucleotides can be the same or different. In one embodiment, the overhang is present at the 3'-end of the sense strand, antisense strand or both strands. In one embodiment, this 3'-overhang is present in the antisense strand. In one embodiment, this 3'-overhang is present in the sense strand.

The dsRNA agent of the invention comprises only single overhang, which can strengthen the interference activity of the dsRNA, without affecting its overall stability. For example, the single-stranded overhang is located at the 3-terminal end of the sense strand or, alternatively, at the 3-terminal end of the antisense strand. The dsRNA may also have a blunt end, located at the 5'-end of the antisense strand (or the 3'-end of the sense strand) or vice versa. Generally, the antisense strand of the dsRNA has a nucleotide overhang at the 3'-end, and the 5'-end is blunt. While not bound by theory, the asymmetric blunt end at the 5'-end of the antisense strand and 3'-end overhang of the antisense strand favor the guide strand loading into RISC process.

In one embodiment, the dsRNA agent of the invention may also have two blunt ends, at both ends of the dsRNA duplex.

In one embodiment, the dsRNA agent of the invention is a double ended bluntmer of 19 nt in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11,12,13 from the 5'end.

In one embodiment, the dsRNA agent of the invention is a double ended bluntmer of 20 nt in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In one embodiment, the dsRNA agent of the invention is a double ended bluntmer of 21 nt in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the dsRNA agent of the invention comprises a 21 nucleotides (nt) sense strand and a 23 nucleotides (nt) antisense, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the dsRNA is blunt, while the other end is comprises a 2 nt overhang. Preferably, the 2 nt overhang is at the 3'-end of the antisense. Optionally, the dsRNA further comprises a ligand (preferably GalNAc$_3$).

In one embodiment, the dsRNA agent of the invention comprising a sense and antisense strands, wherein: the sense strand is 25-30 nucleotide residues in length, wherein starting from the 5' terminal nucleotide (position 1) positions 1 to 23 of said first strand comprise at least 8 ribonucleotides; antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when said double stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the dsRNA agent of the invention comprising a sense and antisense strands, wherein said dsRNA agent comprises a first strand having a length which is at least 25 and at most 29 nucleotides and a second strand having a length which is at most 30 nucleotides with at least one motif of three 2'-O-methyl modifications on three consecutive nucleotides at position 11,12,13 from the 5' end; wherein said 3' end of said first strand and said 5' end of said second strand form a blunt end and said second strand is 1-4 nucleotides longer at its 3' end than the first strand, wherein the duplex region which is at least 25 nucleotides in length, and said second strand is sufficiently complementary to a target mRNA along at least 19 nt of said second strand length to reduce target gene expression when said dsRNA agent is introduced into a mammalian cell, and wherein dicer cleavage of said dsRNA preferentially results in an siRNA comprising said 3' end of said second strand, thereby reducing expression of the target gene in the mammal. Optionally, the dsRNA agent further comprises a ligand.

In one embodiment, the sense strand of the dsRNA agent contains at least one motif of three identical modifications on three consecutive nucleotides, where one of the motifs occurs at the cleavage site in the sense strand.

In one embodiment, the antisense strand of the dsRNA agent can also contain at least one motif of three identical modifications on three consecutive nucleotides, where one of the motifs occurs at or near the cleavage site in the antisense strand.

For dsRNA agent having a duplex region of 17-23 nt in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the $1^{st}$ nucleotide from the 5'-end of the antisense strand, or, the count starting from the $1^{st}$ paired nucleotide within the duplex region from the 5'-end of the antisense strand. The cleavage site in the antisense strand may also change according to the length of the duplex region of the dsRNA from the 5'-end.

The sense strand of the dsRNA agent comprises at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides of the motifs from both strands may overlap, or all three nucleotides may overlap.

In one embodiment, the sense strand of the dsRNA agent comprises more than one motif of three identical modifications on three consecutive nucleotides. The first motif should occur at or near the cleavage site of the strand and the other motifs may be a wing modifications. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other the chemistry of the motifs are distinct from each other and when the motifs are separated by one or more nucleotide the chemistries of the motifs can be the same or different. Two or more wing modifications may be present. For instance, when two wing modifications are present, the wing modifications may both occur at one end of the duplex region relative to the first motif which is at or near the cleavage site or each of the wing modifications may occur on either side of the first motif.

Like the sense strand, the antisense strand of the dsRNA agent comprises at least two motifs of three identical modifications on three consecutive nucleotides, with at least one of the motifs occurring at or near the cleavage site of the strand. This antisense strand may also contain one or more wing modifications in an alignment similar to the wing modifications that is present on the sense strand.

In one embodiment, the wing modification on the sense strand, antisense strand, or both strands of the dsRNA agent typically does not include the first one or two terminal nucleotides at the 3'-end, 5'-end or both ends of the strand.

In another embodiment, the wing modification on the sense strand, antisense strand, or both strands of the dsRNA agent typically does not include the first one or two paired nucleotides within the duplex region at the 3'-end, 5'-end or both ends of the strand.

When the sense strand and the antisense strand of the dsRNA agent each contain at least one wing modification, the wing modifications may fall on the same end of the duplex region, and have an overlap of one, two or three nucleotides.

When the sense strand and the antisense strand of the dsRNA agent each contain at least two wing modifications, the sense strand and the antisense strand can be aligned so that two wing modifications each from one strand fall on one end of the duplex region, having an overlap of one, two or three nucleotides; two modifications each from one strand fall on the other end of the duplex region, having an overlap of one, two or three nucleotides.

In one embodiment, every nucleotide in the sense strand and antisense strand of the dsRNA agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand.

A modification may occur in a double strand region, a single strand region, or in both. A modification may occur only in the double strand region of a RNA or may only occur in a single strand region of a RNA. E.g., a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. E.g., it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with LNA, HNA, CeNA, 2'-methoxyethyl, 2'-O-methyl, 2'-O-allyl, 2'-C-allyl, 2'-deoxy, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the sense strand and antisense strand each contains two differently modified nucleotides selected from 2'-O-methyl or 2'-fluoro.

In one embodiment, each residue of the sense strand and antisense strand is independently modified with 2'-O-methyl nucleotide, 2'-deoxyfluoro nucleotide, 2'-O-N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, or 2'-ara-F nucleotide.

In one embodiment, the $N_a$ and/or $N_b$ comprise modifications of an alternating pattern. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ,"

"AABAABAABAAB . . . ," "AAABAAABAAAB . . . ," "AAABBBAAABBB . . . ," or "ABCABCABCABC . . . ," etc.

In one embodiment, the $N_a'$ and/or $N_b'$ comprise modifications of an alternating pattern. The term "alternating motif" or "alternative pattern" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AABBAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In one embodiment, the dsRNA agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 3'-5' of the strand within the duplex region. As another example, the alternating motif in the sense strand may start with "AABBAABB" from 5'-3' of the strand and the alternating motif in the antisense strand may start with "BBAABBAA" from 3'-5' of the strand within the duplex region, so that there is a complete or partial shift of the modification patterns between the sense strand and the antisense strand.

In one embodiment, the dsRNA agent of the invention comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing activity to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The dsRNA agent of the invention may further comprise at least one phosphorothioate or methylphosphonate internucleotide linkage. The phosphorothioate or methylphosphonate internucleotide linkage modification may occur on any nucleotide of the sense strand or antisense strand or both in any position of the strand. For instance, the internucleotide linkage modification may occur on every nucleotide on the sense strand and/or antisense strand; each internucleotide linkage modification may occur in an alternating pattern on the sense strand or antisense strand; or the sense strand or antisense strand comprises both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In one embodiment, the dsRNA comprises the phosphorothioate or methylphosphonate internucleotide linkage modification in the overhang region. For example, the overhang region comprises two nucleotides having a phosphorothioate or methylphosphonate internucleotide linkage between the two nucleotides. Internucleotide linkage modifications also may be made to link the overhang nucleotides with the terminal paired nucleotides within duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. Preferably, these terminal three nucleotides may be at the 3'-end of the antisense strand.

In one embodiment the sense strand of the dsRNA comprises 1-10 blocks of two to ten phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said sense strand is paired with an antisense strand comprising any combination of phosphorothioate, methylphosphonate and phosphate internucleotide linkages or an antisense strand comprising either phosphorothioate or methylphophonate or phosphate linkage.

In one embodiment the antisense strand of the dsRNA comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In one embodiment the antisense strand of the dsRNA comprises two blocks of three phosphorothioate or methylphosphonate internucleotide linkages separated by 1, 2, 3, 4, 5, 6, 7, 8, 9, 10, 11, 12, 13, 14, 15 or 16 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In one embodiment the antisense strand of the dsRNA comprises two blocks of four phosphorothioate or methylphosphonate internucleotide linkages separated by 1, 2, 3, 4, 5, 6, 7, 8, 9, 10, 11, 12, 13 or 14 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In one embodiment the antisense strand of the dsRNA comprises two blocks of five phosphorothioate or methylphosphonate internucleotide linkages separated by 1, 2, 3, 4, 5, 6, 7, 8, 9, 10, 11 or 12 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In one embodiment the antisense strand of the dsRNA comprises two blocks of six phosphorothioate or methylphosphonate internucleotide linkages separated by 1, 2, 3, 4, 5, 6, 7, 8, 9 or 10 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In one embodiment the antisense strand of the dsRNA comprises two blocks of seven phosphorothioate or methylphosphonate internucleotide linkages separated by 1, 2, 3, 4, 5, 6, 7 or 8 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In one embodiment the antisense strand of the dsRNA comprises two blocks of eight phosphorothioate or methylphosphonate internucleotide linkages separated by 1, 2, 3, 4, 5 or 6 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In one embodiment the antisense strand of the dsRNA comprises two blocks of nine phosphorothioate or methylphosphonate internucleotide linkages separated by 1, 2, 3 or 4 phosphate internucleotide linkages, wherein one of the phosphorothioate or methylphosphonate internucleotide linkages is placed at any position in the oligonucleotide sequence and the said antisense strand is paired with a sense strand comprising any combination of phosphorothioate, methylphosphonate and phosphate internucleotide linkages or an antisense strand comprising either phosphorothioate or methylphophonate or phosphate linkage.

In one embodiment, the dsRNA of the invention further comprises one or more phosphorothioate or methylphosphonate internucleotide linkage modification within 1-10 of the termini position(s) of the sense and/or antisense strand. For example, at least 2, 3, 4, 5, 6, 7, 8, 9 or 10 nucleotides may be linked through phosphorothioate or methylphosphonate internucleotide linkage at one end or both ends of the sense and/or antisense strand.

In one embodiment, the dsRNA of the invention further comprises one or more phosphorothioate or methylphosphonate internucleotide linkage modification within 1-10 of the internal region of the duplex of each of the sense and/or antisense strand. For example, at least 2, 3, 4, 5, 6, 7, 8, 9 or 10 nucleotides may be linked through phosphorothioate methylphosphonate internucleotide linkage at position 8-16 of the duplex region counting from the 5'-end of the sense strand; the dsRNA can optionally further comprise one or more phosphorothioate or methylphosphonate internucleotide linkage modification within 1-10 of the termini position(s).

In one embodiment, the dsRNA of the invention further comprises one to five phosphorothioate or methylphosphonate internucleotide linkage modification(s) within position 1-5 and one to five phosphorothioate or methylphosphonate internucleotide linkage modification(s) within position 18-23 of the sense strand (counting from the 5'-end), and one to five phosphorothioate or methylphosphonate internucleotide linkage modification at positions 1 and 2 and one to five within positions 18-23 of the antisense strand (counting from the 5'-end).

In one embodiment, the dsRNA of the invention further comprises one phosphorothioate internucleotide linkage modification within position 1-5 and one phosphorothioate or methylphosphonate internucleotide linkage modification within position 18-23 of the sense strand (counting from the 5'-end), and one phosphorothioate internucleotide linkage modification at positions 1 and 2 and two phosphorothioate or methylphosphonate internucleotide linkage modifications within positions 18-23 of the antisense strand (counting from the 5'-end).

In one embodiment, the dsRNA of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In one embodiment, the dsRNA of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In one embodiment, the dsRNA of the invention further comprises two phosphorothioate internucleotide linkage modifications within position 1-5 and two phosphorothioate internucleotide linkage modifications within position 18-23 of the sense strand (counting from the 5'-end), and one phosphorothioate internucleotide linkage modification at positions 1 and 2 and one phosphorothioate internucleotide linkage modification within positions 18-23 of the antisense strand (counting from the 5'-end).

In one embodiment, the dsRNA of the invention further comprises one phosphorothioate internucleotide linkage modification within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In one embodiment, the dsRNA of the invention further comprises one phosphorothioate internucleotide linkage modification within position 1-5 and one within position 18-23 of the sense strand (counting from the 5'-end), and two phosphorothioate internucleotide linkage modification at positions 1 and 2 and one phosphorothioate internucleotide linkage modification within positions 18-23 of the antisense strand (counting from the 5'-end).

In one embodiment, the dsRNA of the invention further comprises one phosphorothioate internucleotide linkage modification within position 1-5 (counting from the 5'-end), and two phosphorothioateinternucleotide linkage modifications at positions 1 and 2 and one phosphorothioate internucleotide linkage modification within positions 18-23 of the antisense strand (counting from the 5'-end).

In one embodiment, the dsRNA of the invention further comprises two phosphorothioate internucleotide linkage modifications within position 1-5 (counting from the 5'-end), and one phosphorothioateinternucleotide linkage modification at positions 1 and 2 and two phosphorothioate internucleotide linkage modifications within positions 18-23 of the antisense strand (counting from the 5'-end).

In one embodiment, the dsRNA of the invention further comprises two phosphorothioate internucleotide linkage modifications within position 1-5 and one within position 18-23 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

In one embodiment, the dsRNA of the invention further comprises two phosphorothioate internucleotide linkage modifications within position 1-5 and one phosphorothioate internucleotide linkage modification within position 18-23 of the sense strand (counting from the 5'-end), and two phosphorothioate internucleotide linkage modifications at positions 1 and 2 and two phosphorothioate internucleotide linkage modifications within positions 18-23 of the antisense strand (counting from the 5'-end).

In one embodiment, the dsRNA of the invention further comprises two phosphorothioate internucleotide linkage modifications within position 1-5 and one phosphorothioate internucleotide linkage modification within position 18-23 of the sense strand (counting from the 5'-end), and one phosphorothioate internucleotide linkage modification at positions 1 and 2 and two phosphorothioate internucleotide linkage modifications within positions 18-23 of the antisense strand (counting from the 5'-end).

In one embodiment, the dsRNA of the invention further comprises two phosphorothioate internucleotide linkage modifications at position 1 and 2, and two phosphorothioate internucleotide linkage modifications at position 20 and 21 of the sense strand (counting from the 5'-end), and one phosphorothioate internucleotide linkage modification at positions 1 and one at position 21 of the antisense strand (counting from the 5'-end).

In one embodiment, the dsRNA of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 20 and 21 the antisense strand (counting from the 5'-end).

In one embodiment, the dsRNA of the invention further comprises two phosphorothioate internucleotide linkage modifications at position 1 and 2, and two phosphorothioate internucleotide linkage modifications at position 21 and 22 of the sense strand (counting from the 5'-end), and one phosphorothioate internucleotide linkage modification at positions 1 and one phosphorothioate internucleotide linkage modification at position 21 of the antisense strand (counting from the 5'-end).

In one embodiment, the dsRNA of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 21 and 22 the antisense strand (counting from the 5'-end).

In one embodiment, the dsRNA of the invention further comprises two phosphorothioate internucleotide linkage modifications at position 1 and 2, and two phosphorothioate internucleotide linkage modifications at position 22 and 23 of the sense strand (counting from the 5'-end), and one phosphorothioate internucleotide linkage modification at positions 1 and one phosphorothioate internucleotide linkage modification at position 21 of the antisense strand (counting from the 5'-end).

In one embodiment, the dsRNA of the invention further comprises one phosphorothioate internucleotide linkage modification at position 1, and one phosphorothioate internucleotide linkage modification at position 21 of the sense strand (counting from the 5'-end), and two phosphorothioate internucleotide linkage modifications at positions 1 and 2 and two phosphorothioate internucleotide linkage modifications at positions 23 and 23 the antisense strand (counting from the 5'-end).

In one embodiment, the dsRNA agent of the invention comprises mismatch(es) with the target, within the duplex, or combinations thereof. The mismatch can occur in the overhang region or the duplex region. The base pair can be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the dsRNA agent of the invention comprises at least one of the first 1, 2, 3, 4, or 5 base pairs within the duplex regions from the 5'-end of the antisense strand can be chosen independently from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In one embodiment, the sense strand sequence may be represented by formula (I):

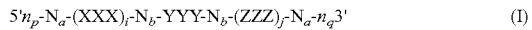  (I)

wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides; each $N_b$ independently represents an oligonucleotide sequence comprising 0-10 modified nucleotides;
each $n_p$ and $n_q$ independently represent an overhang nucleotide;
wherein $N_b$ and Y do not have the same modification; and
XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the dsRNA agent has a duplex region of 17-23 nucleotide pairs in length, the YYY motif can occur at or the vicinity of the cleavage site (e.g.: can occur at positions 6, 7, 8, 7, 8, 9, 8, 9, 10, 9, 10, 11, 10, 11,12 or 11, 12, 13) of—the sense strand, the count starting from the 1st nucleotide, from the 5'-end; or optionally, the count starting at the 1$^{st}$ paired nucleotide within the duplex region, from the 5'-end.

In one embodiment, i is 1 and j is 0, or i is 0 and j is 1, or both i and j are 1. The sense strand can therefore be represented by the following formulas:

  (Ia);

  (Ib); or

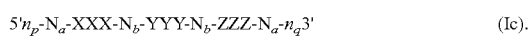  (Ic).

When the sense strand is represented by formula (Ia), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ib), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Ic), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides.

Each of X, Y and Z may be the same or different from each other.

In one embodiment, the antisense strand sequence of the dsRNA may be represented by formula (II):

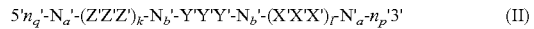  (II)

wherein:
k and l are each independently 0 or 1;
p and q are each independently 0-6;
each $N_a'$ independently represents an oligonucleotide sequence comprising 0-25 modified nucleotides, each sequence comprising at least two differently modified nucleotides;
each $N_b'$ independently represents an oligonucleotide sequence comprising 0-10 modified nucleotides;
each $n_p'$ and $n_q'$ independently represent an overhang nucleotide comprising 0-6 nucleotides;
wherein $N_b'$ and Y' do not have the same modification; and
X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the dsRNA agent has a duplex region of 17-23 nt in length, the Y'Y'Y' motif can occur at positions 9, 10, 11; 10, 11, 12; 11, 12, 13; 12, 13, 14; or 13, 14, 15 of the antisense strand, with the count starting from the 1$^{st}$ nucleotide, from the 5'-end; or optionally, the count starting at the 1$^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

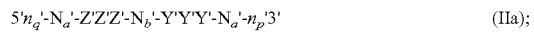  (IIa);

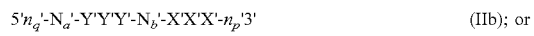  (IIb); or

  (IIc).

When the antisense strand is represented by formula (IIa), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIb), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the dsRNA agent comprises YYY motif occurring at 9, 10 and 11 positions of the strand when the duplex region is 21 nt, the count starting from the 1$^{st}$ nucleotide from the 5'-end, or optionally, the count starting at the 1$^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1$^{st}$ nucleotide from the 5'-end, or optionally, the count starting at the 1$^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib) and (Ic) forms a duplex with a antisense strand being represented by any one of formulas (IIa), (IIb) and (IIc), respectively.

Accordingly, the dsRNA agent may comprise a sense strand and an antisense strand, each strand having 14 to 30 nucleotides, the dsRNA duplex represented by formula (III):

sense: 5'$n_p$-$N_a$-(XXX)$_i$-$N_b$-YYY-$N_b$-(ZZZ)$_j$-$N_a$-$n_q$3'

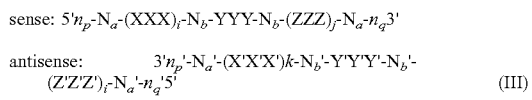
(III)

wherein:
i, j, k, and l are each independently 0 or 1;
p and q are each independently 0-6;
each $N_a$ and $N_a'$ independently represents an oligonucleotide sequence comprising 0-25 modified nucleotides, each sequence comprising at least two differently modified nucleotides;
each $N_b$ and $N_b'$ independently represents an oligonucleotide sequence comprising 0-10 modified nucleotides;
wherein
each $n_p'$, $n_p$, $n_q'$, and $n_q$ independently represents an overhang nucleotide sequence; and
XXX, YYY, ZZZ, X'X'X', Y'Y'Y', and Z'Z'Z' each independently represent one motif of three identical modifications on three consecutive nucleotides.

In one embodiment, i is 1 and j is 0; or i is 0 and j is 1; or both i and j are 1. In another embodiment, k is 1 and l is 0; k is 0 and l is 1; or both k and l are 1.

In one embodiment, the dsRNA agent of the invention comprises a sense strand and an antisense strand, each strand having 14 to 30 nucleotides, the dsRNA duplex represented by formula (V):

sense: 5'$N_a$-(XXX)$_i$-$N_b$-YYY-$N_b$-(ZZZ)$_j$-$N_a$-$n_q$3'

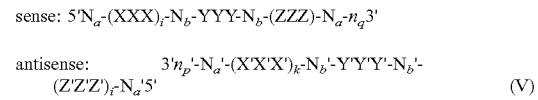
(V)

wherein:
i, j, k, and l are each independently 0 or 1;
p and q are each independently 2;
each $N_a$ and $N_a'$ independently represents an oligonucleotide sequence comprising 0-25 modified nucleotides, each sequence comprising at least two differently modified nucleotides;
each $N_b$ and $N_b'$ independently represents an oligonucleotide sequence comprising 0-10 modified nucleotides;
wherein
each $n_p'$, and $n_q$ independently represents an overhang nucleotide sequence; and
XXX, YYY, ZZZ, X'X'X', Y'Y'Y', and Z'Z'Z' each independently represent one motif of three identical modifications on three consecutive nucleotides.

In one embodiment, i is 1 and j is 0; or i is 0 and j is 1; or both i and j are 1. In another embodiment, k is 1 and l is 0; k is 0 and l is 1; or both k and l are 1.

In one embodiment, the dsRNA agent of the invention comprises a sense strand and an antisense strand, each strand having 14 to 30 nucleotides, the dsRNA duplex represented by formula (Va):

sense: 5'$N_a$-(XXX)$_i$-$N_b$-YYY-$N_b$-(ZZZ)$_j$-$N_a$3'

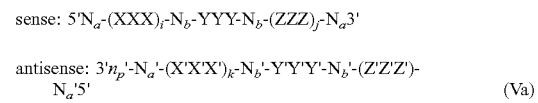
(Va)

wherein:
i, j, k, and l are each independently 0 or 1;
p and q are each independently 2;
each $N_a$ and $N_a'$ independently represents an oligonucleotide sequence comprising 0-25 modified nucleotides, each sequence comprising at least two differently modified nucleotides;
each $N_b$ and $N_b'$ independently represents an oligonucleotide sequence comprising 0-10 modified nucleotides;
wherein
$n_p'$ represents an overhang nucleotide sequence; and
XXX, YYY, ZZZ, X'X'X', Y'Y'Y', and Z'Z'Z' each independently represent one motif of three identical modifications on three consecutive nucleotides.

Exemplary combinations of the sense strand and antisense strand forming a dsRNA duplex include the formulas below:

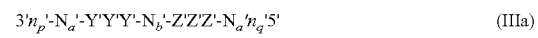
(IIIa)

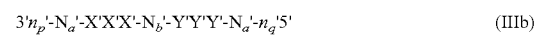
(IIIb)

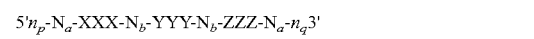

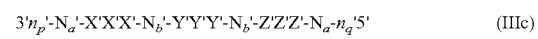
(IIIc)

When the dsRNA agent is represented by formula (IIIa), each $N_b$ and $N_b'$ independently represents an oligonucleotide sequence comprising 1-10, 1-7, 1-5 or 1-4 modified nucleotides. Each $N_a$ and $N_a'$ independently represents an oligonucleotide sequence comprising 2-20, 2-15, or 2-10 modified nucleotides.

When the dsRNA agent is represented as formula (IIIb), each $N_b$ and $N_b'$ independently represents an oligonucleotide sequence comprising 0-10, 0-7, 0-10, 0-7, 0-5, 0-4, 0-2 or 0 modified nucleotides. Each $N_a$ and $N_a'$ independently represents an oligonucleotide sequence comprising 2-20, 2-15, or 2-10 modified nucleotides.

When the dsRNA agent is represented as formula (IIIc), each $N_b$ and $N_b'$ independently represents an oligonucleotide sequence comprising 0-10, 0-7, 0-10, 0-7, 0-5, 0-4, 0-2 or 0 modified nucleotides. Each $N_a$ and $N_a'$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

Each of X, Y and Z in formulas (III), (IIIa), (IIIb) and (IIIc) may be the same or different from each other.

When the dsRNA agent is represented by formula (III), (IIIa), (IIIb) or (IIIc), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

It is understood that $N_a$ nucleotides from base pair with $N_a'$, $N_b$ nucleotides from base pair with $N_b'$, X nucleotides from base pair with X', Y nucleotides from base pair with Y', and Z nucleotides from base pair with Z'.

When the dsRNA agent is represented by formula (IIIa) or (IIIc), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the dsRNA agent is represented as formula (IIIb) or (IIIc), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, the dsRNA agent is a multimer containing at least two duplexes represented by formula (III), (IIIa), (IIIb) or (IIIc), wherein said duplexes are connected by a linker. The linker can be cleavable or non-cleavable. Optionally, said multimer further comprise a ligand. Each of the dsRNA can target the same gene or two different genes; or each of the dsRNA can target same gene at two different target sites.

In one embodiment, the dsRNA agent is a multimer containing three, four, five, six or more duplexes represented by formula (III), (IIIa), (IIIb) or (IIIc), wherein said duplexes are connected by a linker. The linker can be cleavable or non-cleavable. Optionally, said multimer further comprises a ligand. Each of the dsRNA can target the same gene or two different genes; or each of the dsRNA can target same gene at two different target sites.

In one embodiment, two dsRNA agent represented by formula (III), (IIIa), (IIIb) or (IIIc) are linked to each other at the 5' end, and one or both of the 3' ends of the are optionally conjugated to a ligand. Each of the dsRNA can target the same gene or two different genes; or each of the dsRNA can target same gene at two different target sites.

Various publications described multimeric siRNA and can all be used with the dsRNA of the invention. Such publications include WO2007/091269, U.S. Pat. No. 7,858,769, WO2010/141511, WO2007/117686, WO2009/014887 and WO2011/031520 which are hereby incorporated by their entirely.

The dsRNA agent that contains conjugations of one or more carbohydrate moieties to a dsRNA agent can optimize one or more properties of the dsRNA agent. In many cases, the carbohydrate moiety will be attached to a modified subunit of the dsRNA agent. E.g., the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

In embodiment the dsRNA of the invention is conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

The double-stranded RNA (dsRNA) agent of the invention may optionally be conjugated to one or more ligands. The ligand can be attached to the sense strand, antisense strand or both strands, at the 3'-end, 5'-end or both ends. For instance, the ligand may be conjugated to the sense strand, in particular, the 3'-end of the sense strand.

Ligands

A wide variety of entities can be coupled to the oligonucleotides of the present invention. Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH. The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., Biochemistry, 1987, 26: 2964-2972), the EALA peptide (Vogel et al., J. Am. Chem. Soc., 1996, 118: 1581-1586), and their derivatives (Turk et al., Biochem. Biophys. Acta, 2002, 1559: 56-68). In one embodiment, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g. an aptamer). Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer. Table 2 shows some examples of targeting ligands and their associated receptors.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases or a chelator (e.g. EDTA), lipophilic molecules, e.g, cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, multivalent fucose, or aptamers. The ligand can be, for example, a lipopolysaccharide, an activator of p38 MAP kinase, or an activator of NF-κB.

The ligand can be a substance, e.g, a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculinA, phalloidin, swinholide A, indanocine, or myoservin.

The ligand can increase the uptake of the oligonucleotide into the cell by activating an inflammatory response, for example. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP (SEQ ID NO: 1). An RFGF analogue (e.g., amino acid sequence AALLPVLLAAP (SEQ ID NO: 2)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ) (SEQ ID NO: 3) and the Drosophila Antennapedia protein (RQIKIWFQNRRMKWKK) (SEQ ID NO: 4) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., Cancer Res., 62:5139-43, 2002). An RGD peptide can facilitate targeting of an iRNA agent to tumors of a variety of other tissues, including the lung, kidney, spleen, or liver (Aoki et al., Cancer Gene Therapy 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., Jour. Nucl. Med., 42:326-336, 2001). Peptides that target markers enriched in proliferating cells can be used. E.g., RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogeneis. Preferred conjugates of this type ligands that targets PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, S. clava peptides, hagfish intestinal antimicrobial peptides (HFIAPs), magainines, brevinins-2, dermaseptins, melittins, pleurocidin, $H_2A$ peptides, Xenopus peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix.

Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; a, 3, or 7 peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor. Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycaboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulator include lipophiles, bile acids, steroids, phospholipid analogues, peptides, protein binding agents, PEG, vitamins etc. Examplary PK modulator include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g. oligonucleotides of about 5 bases, 10 bases, 15 bases or 20 bases, comprising multiple of phosphorothioate linkages in the backbaone are also amenable to the present invention as ligands (e.g. as PK modulating ligands).

In addition, aptamers that bind serum components (e.g. serum proteins) are also amenable to the present invention as PK modulating ligands.

Other ligand conjugates amenable to the invention are described in U.S. patent application Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser. No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g. a carrier described herein. The ligand or tethered ligand may be present on a monomer when said monomer is incorporated into the growing strand. In some embodiments, the ligand may be incorporated via coupling to a "precursor" monomer after said "precursor" monomer has been incorporated into the growing strand. For example, a monomer having, e.g., an amino-terminated tether (i.e., having no associated ligand), e.g., TAP—$(CH_2)_n N_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties. For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylglucosamine) derivatives attached through a bivalent or trivalent branched linker.

In one embodiment, the dsRNA of the invention is conjugated to a bivalent and trivalent branched linkers include the structures shown in any of formula (IV)-(VII):

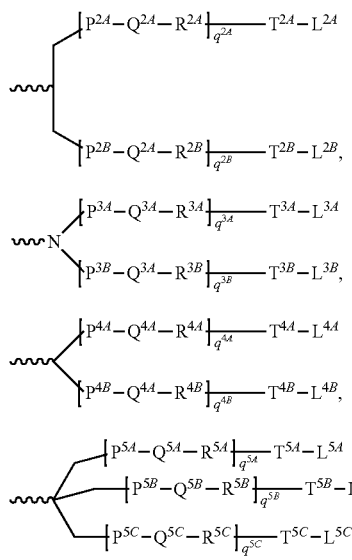

wherein:
- $q^{2A}$, $q^{2B}$, $q^{3A}$, $q^{4A}$, $q^{4B}$, $q^{5A}$, $q^{5B}$ and $q^{5C}$ represent independently for each occurrence 0-20 and wherein the repeating unit can be the same or different;
- $P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), $CH_2$, $CH_2NH$ or $CH_2O$;
- $Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), $SO_2$, $N(R^N)$, C(R')=C(R''), C≡C or C(O);
- $R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, $CH_2$, C(O)O, C(O)NH, $NHCH(R^a)C(O)$, —C(O)—CH($R^a$)—NH—, CO, CH=N—O,

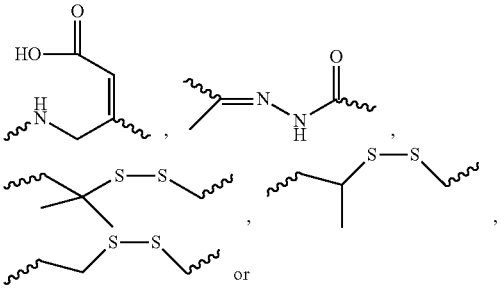

heterocyclyl;
- $L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and
- $R^a$ is H or amino acid side chain.

Trivalent conjugating GalNAc derivatives are particularly useful for use with RNAi agents for inhibiting the expression of a target gene, such as those of formula (VII):

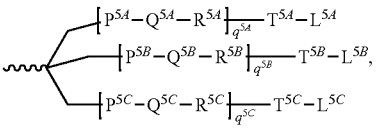

wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the following compounds:

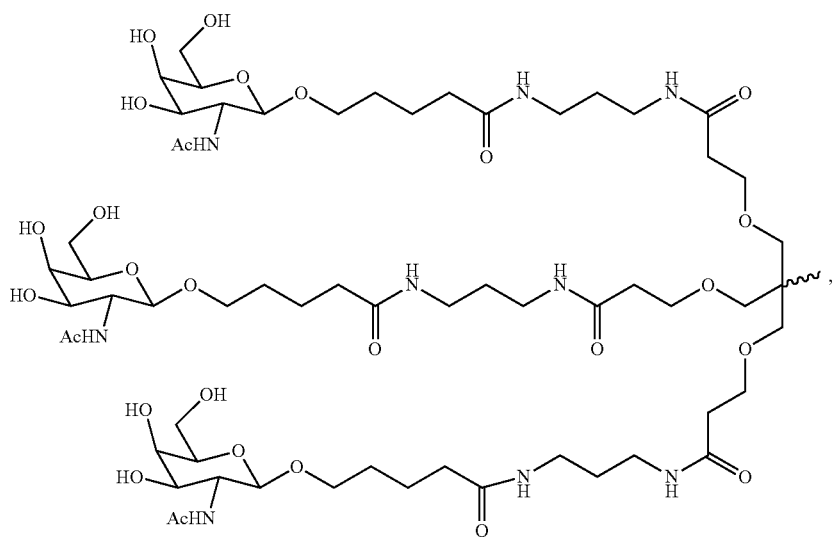

29
-continued
30
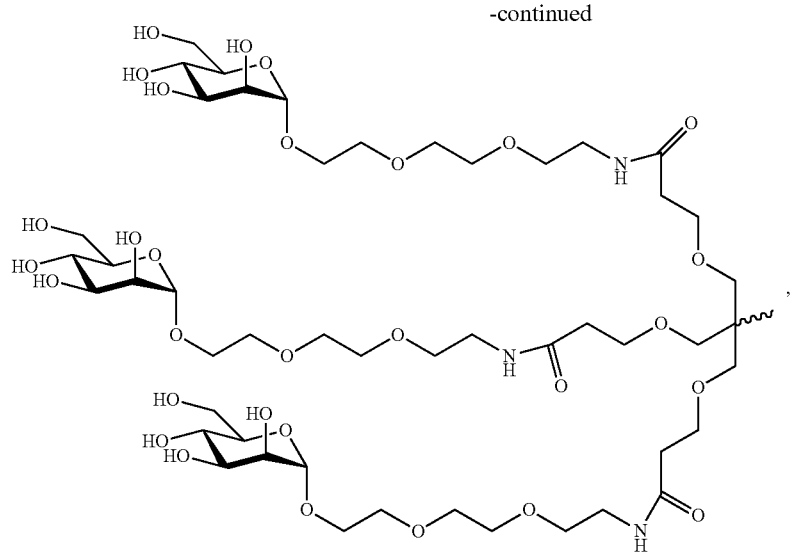
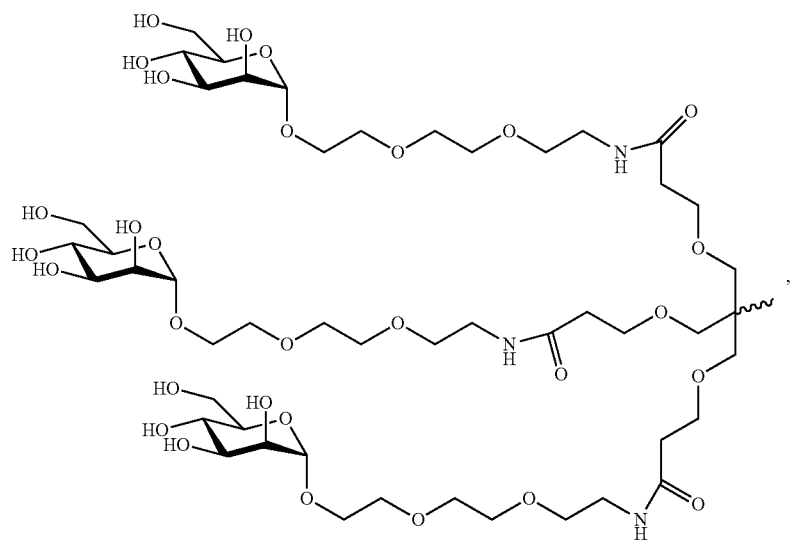
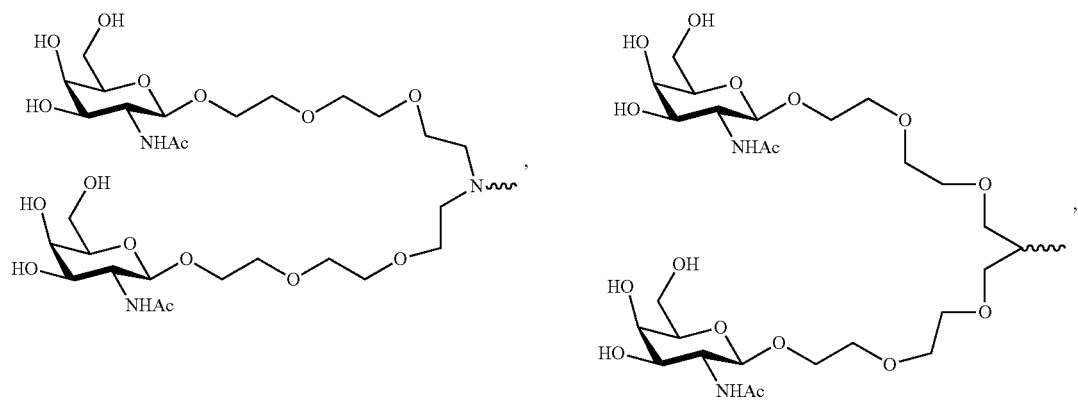

31
32
-continued
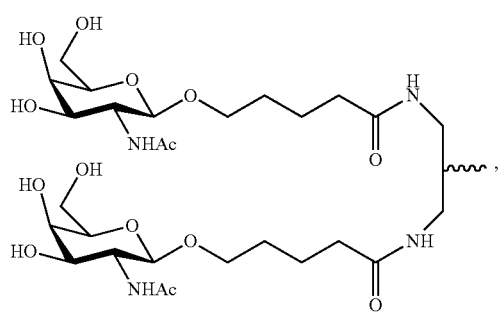
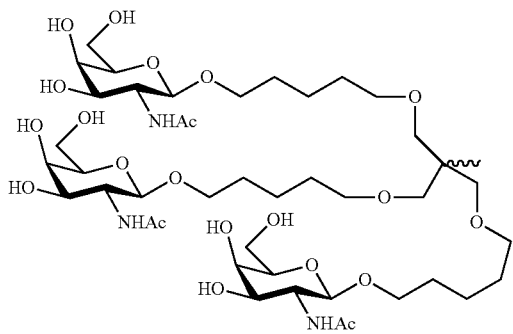
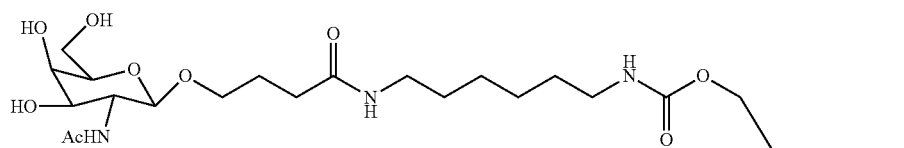
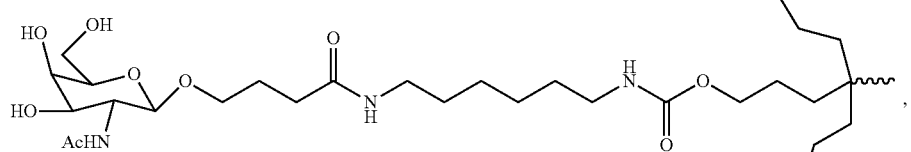
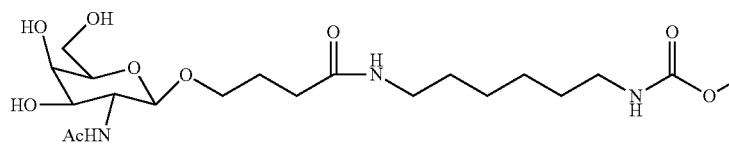
,
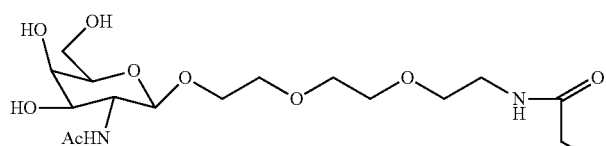
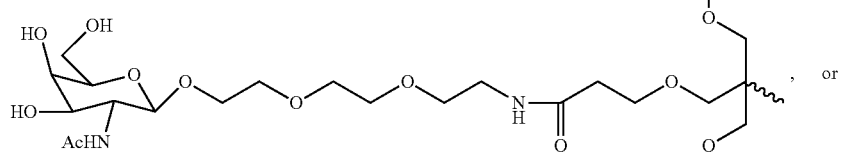
, or
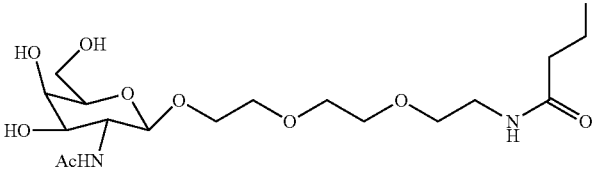

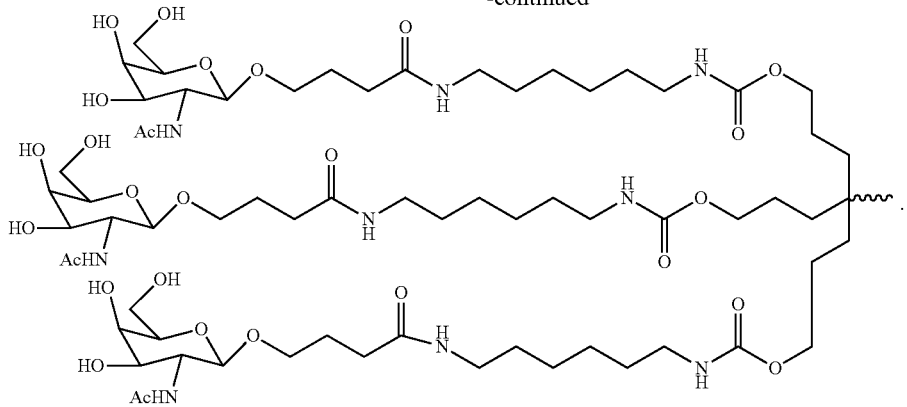

-continued

Definitions

As used herein, the terms "dsRNA", "siRNA", and "iRNA agent" are used interchangeably to agents that can mediate silencing of a target RNA, e.g., mRNA, e.g., a transcript of a gene that encodes a protein. For convenience, such mRNA is also referred to herein as mRNA to be silenced. Such a gene is also referred to as a target gene. In general, the RNA to be silenced is an endogenous gene or a pathogen gene. In addition, RNAs other than mRNA, e.g., tRNAs, and viral RNAs, can also be targeted.

As used herein, the phrase "mediates RNAi" refers to the ability to silence, in a sequence specific manner, a target RNA. While not wishing to be bound by theory, it is believed that silencing uses the RNAi machinery or process and a guide RNA, e.g., an siRNA agent of 21 to 23 nucleotides.

As used herein, "specifically hybridizable" and "complementary" are terms which are used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, i.e., under physiological conditions in the case of assays or therapeutic treatment, or in the case of in vitro assays, under conditions in which the assays are performed. The non-target sequences typically differ by at least 5 nucleotides.

In one embodiment, a dsRNA agent of the invention is "sufficiently complementary" to a target RNA, e.g., a target mRNA, such that the dsRNA agent silences production of protein encoded by the target mRNA. In another embodiment, the dsRNA agent of the invention is "exactly complementary" to a target RNA, e.g., the target RNA and the dsRNA duplex agent anneal, for example to form a hybrid made exclusively of Watson-Crick base pairs in the region of exact complementarity. A "sufficiently complementary" target RNA can include an internal region (e.g., of at least 10 nucleotides) that is exactly complementary to a target RNA. Moreover, in some embodiments, the dsRNA agent of the invention specifically discriminates a single-nucleotide difference. In this case, the dsRNA agent only mediates RNAi if exact complementary is found in the region (e.g., within 7 nucleotides of) the single-nucleotide difference.

As used herein, the term "oligonucleotide" refers to a nucleic acid molecule (RNA or DNA) for example of length less than 100, 200, 300, or 400 nucleotides.

The term "halo" refers to any radical of fluorine, chlorine, bromine or iodine. The term "alkyl" refers to saturated and unsaturated non-aromatic hydrocarbon chains that may be a straight chain or branched chain, containing the indicated number of carbon atoms (these include without limitation propyl, allyl, or propargyl), which may be optionally inserted with N, O, or S. For example, $C_1$-$C_{10}$ indicates that the group may have from 1 to 10 (inclusive) carbon atoms in it. The term "alkoxy" refers to an —O-alkyl radical. The term "alkylene" refers to a divalent alkyl (i.e., —R—). The term "alkylenedioxo" refers to a divalent species of the structure —O—R—O—, in which R represents an alkylene. The term "aminoalkyl" refers to an alkyl substituted with an amino The term "mercapto" refers to an —SH radical. The term "thioalkoxy" refers to an —S-alkyl radical.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, for example, 3 to 8 carbons, and, for example, 3 to 6 carbons, wherein the cycloalkyl group additionally may be optionally substituted. Cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include trizolyl, tetrazolyl, piperazinyl, pyrrolidinyl, dioxanyl, morpholinyl, tetrahydrofuranyl, and the like.

The term "oxo" refers to an oxygen atom, which forms a carbonyl when attached to carbon, an N-oxide when attached to nitrogen, and a sulfoxide or sulfone when attached to sulfur.

The term "acyl" refers to an alkylcarbonyl, cycloalkylcarbonyl, arylcarbonyl, heterocyclylcarbonyl, or heteroarylcarbonyl substituent, any of which may be further substituted by substituents.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent can be further substituted.

Cleavable Linking Groups

A cleavable linking group is one which is sufficiently stable outside the cell, but which upon entry into a target cell is cleaved to release the two parts the linker is holding together. In a preferred embodiment, the cleavable linking group is cleaved at least 10 times or more, preferably at least 100 times faster in the target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing the cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, liver targeting ligands can be linked to the cationic lipids through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It may be useful to make initial evaluations in cell-free or culture conditions and to confirm by further evaluations in whole animals. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

Redox Cleavable Linking Groups

One class of cleavable linking groups are redox cleavable linking groups that are cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In a preferred embodiment, candidate compounds are cleaved by at most 10% in the blood. In preferred embodiments, useful candidate compounds are degraded at least 2, 4, 10 or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

Phosphate-based cleavable linking groups Phosphate-based cleavable linking groups are cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)

(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, S—P(S)(H)—O—, —S—P(O)(H)—S—, —O—P(S)(H)—S—. A preferred embodiment is —O—P(O)(OH)-O-. These candidates can be evaluated using methods analogous to those described above.

Acid Cleavable Linking Groups

Acid cleavable linking groups are linking groups that are cleaved under acidic conditions. In preferred embodiments acid cleavable linking groups are cleaved in an acidic environment with a pH of about 6.5 or lower (e.g., about 6.0, 5.5, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

Ester-Based Linking Groups

Ester-based cleavable linking groups are cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

Peptide-Based Cleaving Groups

Peptide-based cleavable linking groups are cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH-). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above. As used herein, "carbohydrate" refers to a compound which is either a carbohydrate per se made up of one or more monosaccharide units having at least 6 carbon atoms (which may be linear, branched or cyclic) with an oxygen, nitrogen or sulfur atom bonded to each carbon atom; or a compound having as a part thereof a carbohydrate moiety made up of one or more monosaccharide units each having at least six carbon atoms (which may be linear, branched or cyclic), with an oxygen, nitrogen or sulfur atom bonded to each carbon atom. Representative carbohydrates include the sugars (mono-, di-, tri- and oligosaccharides containing from about 4-9 monosaccharide units), and polysaccharides such as starches, glycogen, cellulose and polysaccharide gums. Specific monosaccharides include $C_5$ and above (preferably $C_5$-$C_8$) sugars; di- and trisaccharides include sugars having two or three monosaccharide units (preferably $C_5$-$C_8$).

ALTERNATIVE EMBODIMENTS

In another embodiment, the invention relates to a dsRNA agent capable of inhibiting the expression of a target gene. The dsRNA agent comprises a sense strand and an antisense strand, each strand having 14 to 30 nucleotides. The sense strand contains at least one motif of three identical modifications on three consecutive nucleotides, where at least one of the motifs occurs at or near the cleavage site in the antisense strand. Every nucleotide in the sense strand and antisense strand has been modified. The modifications on sense strand and antisense strand each independently comprises at least two different modifications.

In another embodiment, the invention relates to a dsRNA agent capable of inhibiting the expression of a target gene. The dsRNA agent comprises a sense strand and an antisense strand, each strand having 14 to 30 nucleotides. The sense strand contains at least one motif of three identical modifications on three consecutive nucleotides, where at least one of the motifs occurs at or near the cleavage site in the antisense strand. The antisense strand contains at least one motif of three identical modifications on three consecutive nucleotides. The modification pattern of the antisense strand is shifted by one or more nucleotides relative to the modification pattern of the sense strand.

In another embodiment, the invention relates to a dsRNA agent capable of inhibiting the expression of a target gene. The dsRNA agent comprises a sense strand and an antisense strand, each strand having 14 to 30 nucleotides. The sense strand contains at least two motifs of three identical modifications on three consecutive nucleotides, when at least one of the motifs occurs at the cleavage site in the strand and at least one of the motifs occurs at another portion of the strand that is separated from the motif at the cleavage site by at least one nucleotide. The antisense strand contains at least one motif of three identical modifications on three consecutive nucleotides, where at least one of the motifs occurs at or near the cleavage site in the strand and at least one of the motifs occurs at another portion of the strand that is separated from the motif at or near cleavage site by at least one nucleotide.

In another embodiment, the invention relates to a dsRNA agent capable of inhibiting the expression of a target gene. The dsRNA agent comprises a sense strand and an antisense strand, each strand having 14 to 30 nucleotides. The sense strand contains at least two motifs of three identical modifications on three consecutive nucleotides, where at least one of the motifs occurs at the cleavage site in the strand and at least one of the motifs occurs at another portion of the strand that is separated from the motif at the cleavage site by at least one nucleotide. The antisense strand contains at least one motif of three identical modifications on three consecutive nucleotides, where at least one of the motifs occurs at or near the cleavage site in the strand and at least one of the motifs occurs at another portion of the strand that is separated from the motif at or near cleavage site by at least one nucleotide. The modification in the motif occurring at the cleavage site in the sense strand is different than the modification in the motif occurring at or near the cleavage site in the antisense strand. In another embodiment, the invention relates to a dsRNA agent capable of inhibiting the expression of a target gene. The dsRNA agent comprises a sense strand and an antisense strand, each strand having 12 to 30 nucleotides. The sense strand contains at least one motif of three 2'-F modifications on three consecutive nucleotides, where at least one of the motifs occurs at the cleavage site in the strand. The antisense strand contains at least one motif of three 2'-O-methyl modifications on three consecutive nucleotides.

The sense strand may further comprises one or more motifs of three identical modifications on three consecutive nucleotides, where the one or more additional motifs occur at another portion of the strand that is separated from the three 2'-F modifications at the cleavage site by at least one nucleotide. The antisense strand may further comprises one or more motifs of three identical modifications on three consecutive nucleotides, where the one or more additional motifs occur at another portion of the strand that is separated from the three 2'-O-methyl modifications by at least one nucleotide. At least one of the nucleotides having a 2'-F modification may form a base pair with one of the nucleotides having a 2'-O-methyl modification.

In one embodiment, the dsRNA of the invention is administered in buffer.

In one embodiment, siRNA compounds described herein can be formulated for administration to a subject. A formulated siRNA composition can assume a variety of states. In some examples, the composition is at least partially crystalline, uniformly crystalline, and/or anhydrous (e.g., less than 80, 50, 30, 20, or 10% water). In another example, the siRNA is in an aqueous phase, e.g., in a solution that includes water.

The aqueous phase or the crystalline compositions can, e.g., be incorporated into a delivery vehicle, e.g., a liposome (particularly for the aqueous phase) or a particle (e.g., a microparticle as can be appropriate for a crystalline composition). Generally, the siRNA composition is formulated in a manner that is compatible with the intended method of administration, as described herein. For example, in particular embodiments the composition is prepared by at least one of the following methods: spray drying, lyophilization, vacuum drying, evaporation, fluid bed drying, or a combination of these techniques; or sonication with a lipid, freeze-drying, condensation and other self-assembly.

A siRNA preparation can be formulated in combination with another agent, e.g., another therapeutic agent or an agent that stabilizes a siRNA, e.g., a protein that complexes with siRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

In one embodiment, the siRNA preparation includes another siNA compound, e.g., a second siRNA that can mediate RNAi with respect to a second gene, or with respect to the same gene. Still other preparation can include at least 3, 5, ten, twenty, fifty, or a hundred or more different siRNA species. Such siRNAs can mediate RNAi with respect to a similar number of different genes.

In one embodiment, the siRNA preparation includes at least a second therapeutic agent (e.g., an agent other than a RNA or a DNA). For example, a siRNA composition for the treatment of a viral disease, e.g., HIV, might include a known antiviral agent (e.g., a protease inhibitor or reverse transcriptase inhibitor). In another example, a siRNA composition for the treatment of a cancer might further comprise a chemotherapeutic agent.

Exemplary formulations are discussed below.

Liposomes. For ease of exposition the formulations, compositions and methods in this section are discussed largely with regard to unmodified siRNA compounds. It may be understood, however, that these formulations, compositions and methods can be practiced with other siRNA compounds, e.g., modified siRNAs, and such practice is within the invention. An siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparation can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the siRNA composition. The lipophilic material isolates the aqueous interior from an aqueous exterior, which typically does not include the siRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the siRNA are delivered into the cell where the siRNA can specifically bind to a target RNA and can mediate RNAi. In some cases the liposomes are also specifically targeted, e.g., to direct the siRNA to particular cell types.

A liposome containing a siRNA can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The siRNA preparation is then added to the micelles that include the lipid component. The cationic groups on the lipid interact with the siRNA and condense around the siRNA to form a liposome. After condensation, the detergent is removed, e.g., by dialysis, to yield a liposomal preparation of siRNA.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Further description of methods for producing stable polynucleotide delivery vehicles, which incorporate a polynucleotide/cationic lipid complex as structural components of the delivery vehicle, are described in, e.g., WO 96/37194. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. M. *Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging siRNA preparations into liposomes.

Liposomes that are pH-sensitive or negatively-charged entrap nucleic acid molecules rather than complex with them. Since both the nucleic acid molecules and the lipid are similarly charged, repulsion rather than complex formation occurs. Nevertheless, some nucleic acid molecules are entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 19, (1992) 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and include U.S. Pat. Nos. 5,283,185; 5,171,678; WO 94/00569; WO 93/24640; WO 91/16024; Felgner, *J Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver siRNAs to macrophages.

Further advantages of liposomes include: liposomes obtained from natural phospholipids are biocompatible and biodegradable; liposomes can incorporate a wide range of water and lipid soluble drugs; liposomes can protect encapsulated siRNAs in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of siRNA (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Indiana) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wisconsin) and dipalmitoylphosphatidylethanolamine 5-carboxyspermylamide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, California) and Lipofectamine (DOSPA) (Life Technology, Inc., Gaithersburg, Maryland). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer siRNA, into the skin. In some implementations, liposomes are used for delivering siRNA to epidermal cells and also to enhance the penetration of siRNA into dermal tissues, e.g., into skin. For example, the liposomes can be applied topically. Topical delivery of drugs formulated as liposomes to the skin has been documented (see, e.g., Weiner et al., *Journal of Drug Targeting*, 1992, vol. 2,405-410 and du Plessis et al., *Antiviral Research*, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with siRNA are useful for treating a dermatological disorder.

Liposomes that include siRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include siRNA can be delivered, for example, subcutaneously by infection in order to deliver siRNA to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Surfactants. For ease of exposition the formulations, compositions and methods in this section are discussed largely with regard to unmodified siRNA compounds. It may be understood, however, that these formulations, compositions and methods can be practiced with other siRNA compounds, e.g., modified siRNA compounds, and such practice is within the scope of the invention. Surfactants find wide application in formulations such as emulsions (including microemulsions) and liposomes (see above). siRNA (or a precursor, e.g., a larger dsiRNA which can be processed into a siRNA, or a DNA which encodes a siRNA or precursor) compositions can include a surfactant. In one embodiment, the siRNA is formulated as an emulsion that includes a surfactant. The most common way of classifying and ranking the properties of the many different types of surfactants, both natural and synthetic, is by the use of the hydrophile/lipophile balance (HLB). The nature of the hydrophilic group provides the most useful means for categorizing the different surfactants used in formulations (Rieger, in "Pharmaceutical Dosage Forms," Marcel Dekker, Inc., New York, NY, 1988, p. 285).

If the surfactant molecule is not ionized, it is classified as a nonionic surfactant. Nonionic surfactants find wide application in pharmaceutical products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms," Marcel Dekker, Inc., New York, NY, 1988, p. 285).

Micelles and other Membranous Formulations. For ease of exposition the micelles and other formulations, compositions and methods in this section are discussed largely with regard to unmodified siRNA compounds. It may be understood, however, that these micelles and other formulations, compositions and methods can be practiced with other siRNA compounds, e.g., modified siRNA compounds, and such practice is within the invention. The siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof)) composition can be provided as a micellar formulation. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

Particles. For ease of exposition the particles, formulations, compositions and methods in this section are discussed largely with regard to modified siRNA compounds. It may be understood, however, that these particles, formulations, compositions and methods can be practiced with other siRNA compounds, e.g., unmodified siRNA compounds, and such practice is within the invention. In another embodiment, an siRNA compound, e.g., a double-stranded siRNA compound, or ssiRNA compound, (e.g., a precursor, e.g., a larger siRNA compound which can be processed into a ssiRNA compound, or a DNA which encodes an siRNA compound, e.g., a double-stranded siRNA compound, or ssiRNA compound, or precursor thereof) preparations may be incorporated into a particle, e.g., a microparticle. Microparticles can be produced by spray-drying, but may also be produced by other methods including lyophilization, evaporation, fluid bed drying, vacuum drying, or a combination of these techniques.

Pharmaceutical Compositions

The iRNA agents of the invention may be formulated for pharmaceutical use. Pharmaceutically acceptable compositions comprise a therapeutically-effective amount of one or more of the dsRNA agents in any of the preceding embodiments, taken alone or formulated together with one or more pharmaceutically acceptable carriers (additives), excipient and/or diluents.

The pharmaceutical compositions may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally. Delivery using subcutaneous or intravenous methods can be particularly advantageous.

The phrase "therapeutically-effective amount" as used herein means that amount of a compound, material, or composition comprising a compound of the invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

iRNA agent preparation can be formulated in combination with another agent, e.g., another therapeutic agent or an agent that stabilizes a iRNA, e.g., a protein that complexes with iRNA to form an iRNP. Still other agents include chelators, e.g., EDTA (e.g., to remove divalent cations such as $Mg^{2+}$), salts, RNAse inhibitors (e.g., a broad specificity RNAse inhibitor such as RNAsin) and so forth.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

The compounds according to the invention may be formulated for administration in any convenient way for use in human or veterinary medicine, by analogy with other pharmaceuticals.

The term "treatment" is intended to encompass also prophylaxis, therapy and cure. The patient receiving this treatment is any animal in need, including primates, in particular humans, and other mammals such as equines, cattle, swine and sheep; and poultry and pets in general.

Double-stranded RNAi agents are produced in a cell in vivo, e.g., from exogenous DNA templates that are delivered into the cell. For example, the DNA templates can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) Proc. Natl. Acad. Sci. USA 91:3054-3057). The pharmaceutical preparation of the gene therapy vector can include the gene therapy vector in an acceptable diluent, or can comprise a slow release matrix in which the gene delivery vehicle is imbedded. The DNA templates, for example, can include two transcription units, one that produces a transcript that includes the top strand of a dsRNA agent and one that produces a transcript that includes the bottom strand of a dsRNA agent. When the templates are transcribed, the dsRNA agent is produced, and processed into siRNA agent fragments that mediate gene silencing.

Routes of Delivery

A composition that includes an iRNA can be delivered to a subject by a variety of routes. Exemplary routes include: intravenous, subcutaneous, topical, rectal, anal, vaginal, nasal, pulmonary, ocular.

The iRNA molecules of the invention can be incorporated into pharmaceutical compositions suitable for administration. Such compositions typically include one or more species of iRNA and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the present invention may be administered in a number of ways depending upon whether local or systemic treatment is desired and upon the area to be treated. Administration may be topical (including ophthalmic, vaginal, rectal, intranasal, transdermal), oral or parenteral. Parenteral administration includes intravenous drip, subcutaneous, intraperitoneal or intramuscular injection, or intrathecal or intraventricular administration.

The route and site of administration may be chosen to enhance targeting. For example, to target muscle cells, intramuscular injection into the muscles of interest would be a logical choice. Lung cells might be targeted by administering the iRNA in aerosol form. The vascular endothelial cells could be targeted by coating a balloon catheter with the iRNA and mechanically introducing the DNA.

Dosage

In one aspect, the invention features a method of administering a dsRNA agent, e.g., a siRNA agent, to a subject (e.g., a human subject). The method includes administering a unit dose of the dsRNA agent, e.g., a siRNA agent, e.g., double stranded siRNA agent that (a) the double-stranded part is 14-30 nucleotides (nt) long, for example, 21-23 nt, (b) is complementary to a target RNA (e.g., an endogenous or pathogen target RNA), and, optionally, (c) includes at least one 3' overhang 1-5 nucleotide long. In one embodiment, the unit dose is less than 10 mg per kg of bodyweight, or less than 10, 5, 2, 1, 0.5, 0.1, 0.05, 0.01, 0.005, 0.001, 0.0005, 0.0001, 0.00005 or 0.00001 mg per kg of bodyweight, and less than 200 nmole of RNA agent (e.g., about $4.4 \times 10^{16}$ copies) per kg of bodyweight, or less than 1500, 750, 300, 150, 75, 15, 7.5, 1.5, 0.75, 0.15, 0.075, 0.015, 0.0075, 0.0015, 0.00075, 0.00015 nmole of RNA agent per kg of bodyweight.

The defined amount can be an amount effective to treat or prevent a disease or disorder, e.g., a disease or disorder associated with the target RNA. The unit dose, for example, can be administered by injection (e.g., intravenous, subcutaneous or intramuscular), an inhaled dose, or a topical application. In some embodiments dosages may be less than 10, 5, 2, 1, or 0.1 mg/kg of body weight.

In some embodiments, the unit dose is administered less frequently than once a day, e.g., less than every 2, 4, 8 or 30 days. In another embodiment, the unit dose is not administered with a frequency (e.g., not a regular frequency). For example, the unit dose may be administered a single time.

In one embodiment, the effective dose is administered with other traditional therapeutic modalities. In one embodiment, the subject has a viral infection and the modality is an antiviral agent other than a dsRNA agent, e.g., other than a siRNA agent. In another embodiment, the subject has atherosclerosis and the effective dose of a dsRNA agent, e.g., a siRNA agent, is administered in combination with, e.g., after surgical intervention, e.g., angioplasty.

In one embodiment, a subject is administered an initial dose and one or more maintenance doses of a dsRNA agent, e.g., a siRNA agent, (e.g., a precursor, e.g., a larger dsRNA agent which can be processed into a siRNA agent, or a DNA which encodes a dsRNA agent, e.g., a siRNA agent, or precursor thereof). The maintenance dose or doses can be the same or lower than the initial dose, e.g., one-half less of the initial dose. A maintenance regimen can include treating the subject with a dose or doses ranging from 0.01 g to 15 mg/kg of body weight per day, e.g., 10, 1, 0.1, 0.01, 0.001, or 0.00001 mg per kg of bodyweight per day. The maintenance doses are, for example, administered no more than once every 2, 5, 10, or 30 days. Further, the treatment regimen may last for a period of time which will vary depending upon the nature of the particular disease, its severity and the overall condition of the patient. In certain embodiments the dosage may be delivered no more than once per day, e.g., no more than once per 24, 36, 48, or more hours, e.g., no more than once for every 5 or 8 days. Following treatment, the patient can be monitored for changes in his condition and for alleviation of the symptoms of the disease state. The dosage of the compound may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable.

In one embodiment, the composition includes a plurality of dsRNA agent species. In another embodiment, the dsRNA agent species has sequences that are non-overlapping and non-adjacent to another species with respect to a naturally occurring target sequence. In another embodiment, the plurality of dsRNA agent species is specific for different naturally occurring target genes. In another embodiment, the dsRNA agent is allele specific.

The dsRNA agents of the invention described herein can be administered to mammals, particularly large mammals such as nonhuman primates or humans in a number of ways.

In one embodiment, the administration of the dsRNA agent, e.g., a siRNA agent, composition is parenteral, e.g., intravenous (e.g., as a bolus or as a diffusible infusion), intradermal, intraperitoneal, intramuscular, intrathecal, intraventricular, intracranial, subcutaneous, transmucosal, buccal, sublingual, endoscopic, rectal, oral, vaginal, topical, pulmonary, intranasal, urethral or ocular. Administration can be provided by the subject or by another person, e.g., a health care provider. The medication can be provided in measured doses or in a dispenser which delivers a metered dose. Selected modes of delivery are discussed in more detail below.

The invention provides methods, compositions, and kits, for rectal administration or delivery of dsRNA agents described herein Methods of Inhibiting Expression of the Target Gene Embodiments of the invention also relate to methods for inhibiting the expression of a target gene. The method comprises the step of administering the dsRNA agents in any of the preceding embodiments, in an amount sufficient to inhibit expression of the target gene.

Another aspect the invention relates to a method of modulating the expression of a target gene in a cell, comprising providing to said cell a dsRNA agent of this invention. In one embodiment, the target gene is selected from the group consisting of Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erk1/2 gene, PCNA(p21) gene, MYB gene, JUN gene, FOS gene, BCL-2 gene, hepciden, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF1/CIP1) gene, mutations in the p27(KIP1) gene, mutations in the PPM1D gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

The invention is further illustrated by the following examples, which should not be construed as further limiting. The contents of all references, pending patent applications and published patents, cited throughout this application are hereby expressly incorporated by reference.

EXAMPLES

Example 1. In Vitro Screening of siRNA Duplexes

Cell culture and transfections:

Human Hep3B cells or rat H.II.4.E cells (ATCC, Manassas, VA) were grown to near confluence at 37° C. in an atmosphere of 5% $CO_2$ in RPMI (ATCC) supplemented with 10% FBS, streptomycin, and glutamine (ATCC) before being released from the plate by trypsinization. Transfection was carried out by adding 14.8 µl of Opti-MEM plus 0.2 µl of Lipofectamine RNAiMax per well (Invitrogen, Carlsbad CA. cat #13778-150) to 5 µl of siRNA duplexes per well into a 96-well plate and incubated at room temperature for 15 minutes. 80 µl of complete growth media without antibiotic containing ~$2 \times 10^4$ Hep3B cells were then added to the siRNA mixture. Cells were incubated for either 24 or 120 hours prior to RNA purification. Single dose experiments were performed at 10 nM and 0.1 nM final duplex concentration and dose response experiments were done using 8, 4 fold serial dilutions with a maximum dose of 10 nM final duplex concentration.

Total RNA Isolation Using DYNABEADS mRNA Isolation Kit (Invitrogen, Part #: 610-12):

Cells were harvested and lysed in 150 µl of Lysis/Binding Buffer then mixed for 5 minute at 850 rpm using an Eppendorf Thermomixer (the mixing speed was the same throughout the process). Ten microliters of magnetic beads and 80 µl Lysis/Binding Buffer mixture were added to a round bottom plate and mixed for 1 minute. Magnetic beads were captured using magnetic stand and the supernatant was removed without disturbing the beads. After removing supernatant, the lysed cells were added to the remaining beads and mixed for 5 minutes. After removing supernatant, magnetic beads were washed 2 times with 150 µl Wash Buffer A and mixed for 1 minute. Beads were capture again and supernatant removed. Beads were then washed with 150 µl Wash Buffer B, captured and supernatant was removed. Beads were next washed with 150 µl Elution Buffer, captured and supernatant removed. Beads were allowed to dry for 2 minutes. After drying, 50 µl of Elution Buffer was added and mixed for 5 minutes at 70° C. Beads were captured on magnet for 5 minutes. 40 µl of supernatant was removed and added to another 96 well plate.

cDNA Synthesis Using ABI High Capacity cDNA Reverse Transcription Kit (Applied Biosystems, Foster City, CA, Cat #4368813):

A master mix of 1 µl 10× Buffer, 0.4 µl 25× dNTPs, 1 µl Random primers, 0.5 µl Reverse Transcriptase, 0.5 µl RNase inhibitor and 1.6 µl of H$_2$O per reaction were added into 5 µl total RNA. cDNA was generated using a Bio-Rad C-1000 or 5-1000 thermal cycler (Hercules, CA) through the following steps: 25° C. 10 min, 37° C. 120 min, 85° C. 5 sec, 4° C. hold.

Real Time PCR:

2 µl of cDNA were added to a master mix containing 0.5 µl GAPDH TaqMan Probe (Applied Biosystems Cat #4326317E (human) Cat #4308313 (rodent)), 0.5 µl TTR TaqMan probe (Applied Biosystems cat #HS00174914_m1 (human) cat #Rn00562124_m1 (rat)) and 5 µl Lightcycler 480 probe master mix (Roche Cat #04887301001) per well in a 384 well plate (Roche cat #04887301001). Real time PCR was done in a Roche LC 480 Real Time PCR machine (Roche). Each duplex was tested in at least two independent transfections and each transfection was assayed in duplicate, unless otherwise noted.

To calculate relative fold change, real time data were analyzed using the ΔΔCt method and normalized to assays performed with cells transfected with 10 nM AD-1955, or mock transfected cells. IC$_{50}$s were calculated using a 4 parameter fit model using XLFit and normalized to cells transfected with AD-1955 or naïve cells over the same dose range, or to its own lowest dose. IC$_{50}$s were calculated for each individual transfection as well as in combination, where a single IC$_{50}$ was fit to the data from both transfections.

The results of gene silencing of the exemplary siRNA duplex with various motif modifications of the invention are shown in the table below.

Example 2. RNA Synthesis and Duplex Annealing

1. Oligonucleotide Synthesis:

All oligonucleotides were synthesized on an AKTAoligopilot synthesizer or an ABI 394 synthesizer. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3'-O-N,N'-diisopropyl-2-cyanoethylphosphoramidite, 5'-O-dimethoxytrityl-N4-acetyl-2'-t-butyldimethylsilyl-cytidine-3'-O-N,N'-diisopropyl-2-cyanoethylphosphoramidite, 5'-O-dimethoxytrityl-N2-isobutryl-2'-t-butyldimethylsilyl-guanosine-3'-O-N,N'-diisopropyl-2-cyanoethylphosphoramidite, and 5'-O-dimethoxytrityl-2'-t-butyldimethylsilyl-uridine-3'-O-N,N'-diisopropyl-2-cyanoethylphosphoramidite (Pierce Nucleic Acids Technologies) were used for the oligonucleotide synthesis unless otherwise specified. The 2'-F phosphoramidites, 5'-O-dimethoxytrityl-N4-acetyl-2'-fluro-cytidine-3'-O-N,N'-diisopropyl-2-cyanoethyl-phosphoramidite and 5'-O-dimethoxytrityl-2'-fluro-uridine-3'-O-N,N'-diisopropyl-2-cyanoethyl-phosphoramidite were purchased from (Promega). All phosphoramidites were used at a concentration of 0.2M in acetonitrile (CH$_3$CN) except for guanosine which was used at 0.2M concentration in 10% THF/ANC (v/v). Coupling/recycling time of 16 minutes was used. The activator was 5-ethyl thiotetrazole (0.75M, American International Chemicals), for the PO-oxidation Iodine/Water/Pyridine was used and the PS-oxidation PADS (2%) in 2,6-lutidine/ACN (1:1 v/v) was used.

Ligand conjugated strands were synthesized using solid support containing the corresponding ligand. For example, the introduction of carbohydrate moiety/ligand (for e.g., GalNAc) at the 3'-end of a sequence was achieved by starting the synthesis with the corresponding carbohydrate solid support. Similarly a cholesterol moiety at the 3'-end was introduced by starting the synthesis on the cholesterol support. In general, the ligand moiety was tethered to trans-4-hydroxyprolinol via a tether of choice as described in the previous examples to obtain a hydroxyprolinol-ligand moiety. The hydroxyprolinol-ligand moiety was then coupled to a solid support via a succinate linker or was converted to phosphoramidite via standard phosphitylation conditions to obtain the desired carbohydrate conjugate building blocks. Fluorophore labeled siRNAs were synthesized from the corresponding phosphoramidite or solid support, purchased from Biosearch Technologies. The oleyl lithocholic (GalNAc)$_3$ polymer support made in house at a loading of 38.6 mol/gram. The Mannose (Man)$_3$ polymer support was also made in house at a loading of 42.0 mol/gram.

Conjugation of the ligand of choice at desired position, for example at the 5'-end of the sequence, was achieved by coupling of the corresponding phosphoramidite to the growing chain under standard phosphoramidite coupling conditions unless otherwise specified. An extended 15 min coupling of 0.1M solution of phosphoramidite in anhydrous CH$_3$CN in the presence of 5-(ethylthio)-1H-tetrazole activator to a solid bound oligonucleotide. Oxidation of the internucleotide phosphite to the phosphate was carried out using standard iodine-water as reported (1) or by treatment with tert-butyl hydroperoxide/acetonitrile/water (10:87:3) with 10 min oxidation wait time conjugated oligonucleotide. Phosphorothioate was introduced by the oxidation of phosphite to phosphorothioate by using a sulfur transfer reagent such as DDTT (purchased from AM Chemicals), PADS and or Beaucage reagent The cholesterol phosphoramidite was synthesized in house, and used at a concentration of 0.1 M in dichloromethane. Coupling time for the cholesterol phosphoramidite was 16 minutes.

2. Deprotection-I (Nucleobase Deprotection)

After completion of synthesis, the support was transferred to a 100 ml glass bottle (VWR). The oligonucleotide was cleaved from the support with simultaneous deprotection of base and phosphate groups with 80 mL of a mixture of ethanolic ammonia [ammonia:ethanol (3:1)] for 6.5 h at 55° C. The bottle was cooled briefly on ice and then the ethanolic ammonia mixture was filtered into a new 250 ml bottle. The CPG was washed with 2×40 mL portions of ethanol/water (1:1 v/v). The volume of the mixture was then reduced to ~30 ml by roto-vap. The mixture was then frozen on dry ice and dried under vacuum on a speed vac.

3. Deprotection-I (Removal of 2' TBDMS group)

The dried residue was resuspended in 26 ml of triethylamine, triethylamine trihydrofluoride (TEA·3HF) or pyridine-HF and DMSO (3:4:6) and heated at 60° C. for 90 minutes to remove the tert-butyldimethylsilyl (TBDMS) groups at the 2' position. The reaction was then quenched with 50 ml of 20 mM sodium acetate and pH adjusted to 6.5, and stored in freezer until purification.

4. Analysis

The oligonucleotides were analyzed by high-performance liquid chromatography (HPLC) prior to purification and selection of buffer and column depends on nature of the sequence and or conjugated ligand.

5. HPLC Purification

The ligand conjugated oligonucleotides were purified reverse phase preparative HPLC. The unconjugated oligonucleotides were purified by anion-exchange HPLC on a TSK gel column packed in house. The buffers were 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides were pooled, desalted, and lyophilized. Approximately 0.15 OD of desalted oligonucleotides were diluted in water to 150 μl and then pipetted in special vials for CGE and LC/MS analysis. Compounds were finally analyzed by LC-ESMS and CGE.

6. siRNA Preparation

For the preparation of siRNA, equimolar amounts of sense and antisense strand were heated in 1×PBS at 95° C. for 5 min and slowly cooled to room temperature. Integrity of the duplex was confirmed by HPLC analysis.

TABLE 2

ANGPTL3 modified duplex

| Duplex ID | S ID | Sense strand (S) (SEQ ID NOS 5-424, respectively, in order of appearance) | AS ID | Antisense strand(AS) (SEQ ID NOS 425-844, respectively, in order of appearance) | % of mRNA remained conc, of siRNA | | | IC50 (nM) |
|---|---|---|---|---|---|---|---|---|
| | | | | | 1 nM | 0.1 nM | 0.01 nM | |
| D1000 | S1000 | AfuGfuAfacCfcAfAfGfaGfuAfuCfcCfasu | AS1000 | AfUfgFaAtuAfcIlfcuuGfguUfaAfcAfusGfsa | 0.03 | 0.1 | 0.47 | 0.006 |
| D1001 | S1001 | AfsuGfuAfaCfcAfcAfAfGfaGfuAfuuCfasUf | AS1001 | aUfsgGfaAfAfuAfcUfcuuGfgUfuAfcAfusGfsa | 0.03 | 0.10 | 0.49 | 0.0065 |
| D1002 | S1002 | AfuGfuAfaCfcAfcAfAfGfaGfuAfuuCfasUf | AS1002 | aUfgGfaAfAfuAfcUfcuuGfgsUfuAfcAfusGfsa | 0.04 | 0.10 | 0.46 | 0.0068 |
| D1003 | S1003 | AfuGfuAfaCfcAfAfGfaGfuAfuuCfasUf | AS1003 | aUfgGfaAfAfuAfcUfcuuGfgUfsuAfcAfusGfsa | 0.05 | 0.12 | 0.56 | 0.0073 |
| D1004 | S1004 | aUGuaAfccAfccAfAfgagUfauuCcasu | AS1004 | AUggAtuaCUcuUgguUAcaUsGsa | 0.07 | 0.13 | 0.44 | 0.008 |
| D1005 | S1005 | AfuGfuAfaCfcAfAfGfaGfuAfuuCfasUf | AS1005 | aUfgGfaAfAfuAfcUfcuuGfgsUfsuAfcAfusGfsa | 0.06 | 0.11 | 0.53 | 0.0093 |
| D1006 | S1006 | AfuGfuAfaAfccAfAfGfaGfuAfuuCfasUf | AS1006 | aUfgGfaAfAfuAfcUfcuuGfgUfuAfcAfusGfsa | 0.05 | 0.16 | 0.55 | 0.0095 |
| D1007 | S1007 | AfuGfuAfAfCfcAfAfGfaGfuAfuUfCfcAfgsAf | AS1007 | aUfgGfaAfAfuAfcUfcuuGfguuAfcAfusGfsa | 0.05 | 0.14 | 0.48 | 0.0098 |
| D1008 | S1008 | auguaaccaadGaQguAudAcdGasu | AS1008 | aUfgGfaAfAfuAfcUfcUfuGfgUfuAfcAfusGfsa | 0.07 | 0.11 | 0.33 | 0.010 |
| D1009 | S1009 | UfgGfGfaIfuCfAfUfgUfaAfccCfAfAfgsaAf | AS1009 | uCfuugGfuAfCfaugAfaAfuccAfaCfasUfsc | 0.03 | 0.14 | 0.56 | 0.0101 |
| D1010 | S1010 | UfgGfgauUfuCfAfUfgUfaAfcAfcAfasAf | AS1010 | uCfuUfgGfuUfaCfaugAfaAfuAfaAfUfCfcCfasUfsc | 0.03 | 0.14 | 0.65 | 0.0101 |
| D1011 | S1011 | AfuGfgAfuUfuCfAfAfGfuAfuAfuUfCfcCfasUf | AS1011 | aUfgGfaAfAfuAfcUfcuuGfguuAfcAfUfsgsa | 0.06 | 0.10 | 0.55 | 0.011 |
| D1012 | S1012 | UfgGfgAfuUfuCfAfUfgUfaaCfaAfgsAf | AS1012 | uCfuUfgGfUfUfaCfaugAfaAfaAfuCfcCfasUfsc | 0.04 | 0.13 | 0.54 | 0.0114 |
| D1013 | S1013 | auguaaccaadGaQguAudAcdGasu | AS1013 | aUfgGfaAfAfuAfcUfcUfugdGudTadCadTsgsa | 0.11 | 0.19 | 0.49 | 0.011 |
| D1014 | S1014 | AfuGfuaaCfcAfAfGfaGfuAfuUfCfcCfasUf | AS1014 | aUfgGfaAfAfuAfcUfcuuGfgUfUfAfcAfusGfsa | 0.04 | 0.16 | 0.59 | 0.013 |
| D1015 | S1015 | AfsuGfuaaCfaAfaGfdAfGfdTAfdTrudCcdAsu | AS1015 | dAUdGgdAadTAfdCUfcUfuGfgUfuAfcAfusGfsa | 0.07 | 0.15 | 0.51 | 0.013 |
| D1016 | S1016 | auGfuAfaCfcAfAfGfaGfuAfuuCfcCfasUf | AS1016 | aUfgGfaAfAfuAfcUfcuuGfgUfuAfcAfusGfsa | 0.05 | 0.14 | 0.64 | 0.013 |
| D1017 | S1017 | UfgGfggAfuUfuCfAfUfgUfaAfcCfaAfgsAf | AS1017 | uCfuufgGfuuaCfaugAfaAfuCfcaAfgsAf | 0.09 | 0.41 | 0.74 | 0.0133 |
| D1018 | S1018 | AfuguAfaCfcAfAfGfaGfuAfuUfcCfasUf | AS1018 | aUfgGfaAfAfuAfcUfcuuGfgUfuAfcCfAfusGfsa | 0.03 | 0.14 | 0.61 | 0.014 |
| D1019 | S1019 | AfuGfuAfaccAfcAfAfGfaGfuAfuuCfcCfasUf | AS1019 | aUfgGfaAfAfuAfcUfcuuGfgUfUfuAfcAfusGfsa | 0.02 | 0.2 | 0.7 | 0.014 |
| D1020 | S1020 | AfsuGfuAfccAfAfgGfuAfAfCfuuuCcasUf | AS1020 | asUfsgGfaAfAfuAfcUfcuuGfgUfuAfcAfusGfsa | 0.04 | 0.16 | 0.67 | 0.0156 |
| D1021 | S1021 | aUfguAfAfccAfgGfaugUfaUfCfcasUf | AS1021 | aUfgGfaAfaUfaCfUfCfuugGfuuAfcCfaUfsgsa | 0.11 | 0.24 | 0.64 | 0.016 |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1022 | S1022 | dTdGgdAdTuudCdAugdTdAacdCdAagsdA | AS1022 | udCdTugdGdTuadCdAugdAdAaudCdCcasdTsc | 0.08 | 0.27 | 0.64 | 0.0161 |
| D1023 | S1023 | AfsuGfuAfaCfcAfAfGfaGfuAfuuccCfasAf | AS1023 | aUfgsGfAfAfuAfcUfcuuGfgUfuAfcAfusGfsa | 0.03 | 0.19 | 0.63 | 0.0163 |
| D1024 | S1024 | UfgGfgAfuUfuCfAfUfguaAfcCfaAfgsAf | AS1024 | uCfuUfgGfuUfAfCfaugAfaAfuCfcCfasUfsc | 0.05 | 0.25 | 0.69 | 0.0164 |
| D1025 | S1025 | UfgGfgAfuUfuCfAfUfgUfAfAfcCfaAfgsAf | AS1025 | uCfuUfgGfuuaCfaugAfaAfuCfcCfasUfsc | 0.04 | 0.18 | 0.75 | 0.0166 |
| D1026 | S1026 | UfgGfgAfuUfuCfAfUfgUfaAfcCfaAfgsAf | AS1026 | uCfuUfgGfuUfaCfaugAfaAfuCfcCfasUfsc | 0.04 | 0.19 | 0.66 | 0.0178 |
| D1027 | S1027 | UfgGfgAfuUfuCfAfUfUfgUfaAfccaAfgsAf | AS1027 | uCfuUfgGfuUfaCfaugAfaAfuCfcCfasUfsc | 0.04 | 0.19 | 0.69 | 0.018 |
| D1028 | S1028 | dAdTgudAdAccdAdAgadGdTaudTdCcasdT | AS1028 | adTdGgadAdTacdTdCuudGGuudAdCausdGsa | 0.15 | 0.29 | 0.72 | 0.018 |
| D1029 | S1029 | AdTGdTAdAdCdCdAdAgaGdTAdTUdCCdAsU | AS1029 | dAUdGgAAdTAdCUdCUdTdGdGUdTAdCAdTsGsdA | 0.1 | 0.27 | 0.61 | 0.0187 |
| D1030 | S1030 | UfgGfGfAfuuuCfAfUfgUfaAfCfaAfgsAf | AS1030 | uCfuUfgGfuUfaCfaugAfaAfuCfcCfasUfsc | 0.04 | 0.21 | 0.64 | 0.019 |
| D1031 | S1031 | AfuGfuAfAfccAfaCfcAfAfGfAfGfuAfuuccAfsu | AS1031 | AfUfGfGfAfAfuAfCfuUfcUfuGfuGfuuAfcAfusGfsa | 0.06 | 0.15 | 0.62 | 0.021 |
| D1032 | S1032 | AfsuGfuAfaCfcAfAfGfaGfuGfUfaacCfaAfgsAf | AS1032 | asUfgGfGfAfAfuAfCfUfuCfuUfGfuuAfcAfusGfsa | 0.09 | 0.34 | 0.78 | 0.0212 |
| D1033 | S1033 | UfgGfgAfuUfgUfCfaUfGfgUfaacCfaAfgsAf | AS1033 | uCfuUfgGfuUfaAfcUfcCfaAfgsAf | 0.06 | 0.26 | 0.57 | 0.0216 |
| D1034 | S1034 | AfuGfuAfAfccAfaGfaGfuAfuAfcCfaAfgsAf | AS1034 | aUfgGfeaAfuUfcUfcuuGfgAfaAfAfuCfcUfasGfsa | 0.11 | 0.39 | 0.82 | 0.0222 |
| D1035 | S1035 | UfgGfgAfuuuCfAfUfgUfCfaAfcCfaAfgsAf | AS1035 | uCfuUfgGfuUfaCfaugAfaAfAfuCfcCfasUfsc | 0.04 | 0.16 | 0.56 | 0.0234 |
| D1036 | S1036 | UfgGfGfAfuUfuCfaAfUfgUfAfaCfCfAfAfgsAf | AS1036 | uCfuugGfuUfaCfaUfgAfaUfgCfaAfuccCfasUfsc | 0.06 | 0.31 | 0.78 | 0.0235 |
| D1037 | S1037 | UfgGfgAfuUfuCfAfUfUfgUfaAfCfcAfaAfgsAf | AS1037 | uCfuUfgGfuUfaCfaugAfaAfuCfcCfasUfsc | 0.03 | 0.14 | 0.62 | 0.0239 |
| D1038 | S1038 | UfgGfggAfUfuuCfAfuuaCfAfAfaccCfAfagsAf | AS1038 | uCfUfugGfUfuacCfAfuugAfAfAfauCfCfCfasUfsc | 0.09 | 0.39 | 0.78 | 0.025 |
| D1039 | S1039 | AfuGfuAfacfcAfAfGfaGfuAfuAfaccCfasaAf | AS1039 | aUfgGfAfAfuAfcUfcuuGfgUfAfAfcAfusGfsa | 0.03 | 0.14 | 0.59 | 0.025 |
| D1040 | S1040 | AfuGfuAfacfcAfAfGfaGfuAfuuccCfaUf | AS1040 | aUfgGfAfAfuAfcUfcuuGfgUfuAfcAfusGfsa | 0.03 | 0.13 | 0.56 | 0.0252 |
| D1041 | S1041 | AfsuGfuAfaCfcAfAfGfaGfuAfuuccCfaAfgsAf | AS1041 | asUfgGfAfAfuAfcUfcuuGfgUfuAfcAfusGfsa | 0.06 | 0.27 | 0.79 | 0.0259 |
| D1042 | S1042 | UfgGfgAfuuuCfAfUfgUfgAfaccCfaAfgsAf | AS1042 | uCfuUfgGfuuaCfaugAfaAfuCfcCfasUfsc | 0.05 | 0.27 | 0.67 | 0.027 |
| D1043 | S1043 | AfsuGfuAfaCfcAfAfGfaGfuauuuCfcCfasAf | AS1043 | aUfgGfeaAfuAfcUfcuuGfgUfuAfcAfusGfsa | 0.02 | 0.16 | 0.63 | 0.0271 |
| D1044 | S1044 | AfsuGfuAfaCfcAfcAfAfGfaGfuauuccCfasuf | AS1044 | asUfgGfAfAfuAfcUfcuuGfgsUfsuAfcAfusGfsa | 0.06 | 0.30 | 0.81 | 0.0271 |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1045 | S1045 | aUfguAfaccAfAfgaGfauUfCfcasUf | AS1045 | aUfgGfgaAfUfacUfCfuuGfGfuuAfCfaUfsgsa | 0.12 | 0.29 | 0.8 | 0.028 |
| D1046 | S1046 | AfuGfuAfaCfcAfAfgGfaguAfuUfcCfasUf | AS1046 | aUfgGfaAfuAfUfCfuuGfgUfuAfcAfusGfsa | 0.03 | 0.15 | 0.59 | 0.030 |
| D1047 | S1047 | UfgGfGfAfUfuCfaUfgUfAfAfcCfaAfgsAf | AS1047 | uCfuUfgGfuuaCfaUfgAfaAfuccCfasUfsc | 0.08 | 0.44 | 0.83 | 0.0324 |
| D1048 | S1048 | AfuGfuAfaCfcAfAfgGfaGfuuAfuUfcCfasUf | AS1048 | aUfgGfaAfuAfUfcUfcuuGfgUfuAfcAfusGfsa | 0.07 | 0.23 | 0.67 | 0.036 |
| D1049 | S1049 | AfuGfuAfaCfcAfAfgGfAfGfuAfuuccAfsu | AS1049 | AfUfGfGfAfAfuAfUfCfUfUfGfGfuAfCfcUfasUf | 0.08 | 0.23 | 0.73 | 0.037 |
| D1050 | S1050 | UfgGfgAfuucCfaUfgUfaAfcCfAfAfgsAf | AS1050 | uCfuuggGfuUfaCfaUfgAfaAfuCfcCfasUfsc | 0.06 | 0.29 | 0.78 | 0.0372 |
| D1051 | S1051 | AfuGfuAfaccaagaguAfuUfcCfasUf | AS1051 | aUfgGfaAfudAcdTcdTudGgdTuAfcAfusgsa | 0.12 | 0.41 | 0.86 | 0.040 |
| D1052 | S1052 | AfuguAfaccAfaGfdAGfdAGfdTAdTUdCcdAsu | AS1052 | aUfgGfaAfuAfcUfcUfuGfGfUfuAfCfAfusGfsa | 0.1 | 0.22 | 0.72 | 0.042 |
| D1053 | S1053 | AfuguAfaccAfaCfAfaGfdAGfAfAfcCfaAfgsAf | AS1053 | dAUdGGdAaAfTafdCfcUfcUfuGfGfUfuAfCfAfusGfsa | 0.09 | 0.31 | 0.69 | 0.044 |
| D1054 | S1054 | AfuguAfaccAfaCfcAfaGfaGfdTAfuUfcCfdAAfsu | AS1054 | adTdgGfaAfudAdAfTafcUfcUfuGfGfuUfgUfuAfcAfusGfsa | 0.1 | 0.45 | 0.75 | 0.047 |
| D1055 | S1055 | AfuguAfaccAfaCfaGfaGfdTAdTUdCcdAsu | AS1055 | dAUdGGdAadTadCafdTdCuudGdGuudAdCadTsgsa | 0.12 | 0.26 | 0.7 | 0.049 |
| D1056 | S1056 | AuGuAaCCaGaGuAuUcCasU | AS1056 | aUfgGaAuAcUcUuGgUuAcAusGsa | 0.08 | 0.24 | 0.65 | 0.050 |
| D1057 | S1057 | AfuguAfaccAfaGfuauUfccasUf | AS1057 | aUfGfGfaAfuAfAfcUfcUfuGfGfUfuAfcfAfAfusGfsa | 0.14 | 0.42 | 0.62 | 0.051 |
| D1058 | S1058 | AfuGfuAfaccaagaguAfuUfcCfasUf | AS1058 | aUfgGfaAfudAcdTcdTudGgdTuAfcAfusGfsa | 0.12 | 0.36 | 0.86 | 0.053 |
| D1059 | S1059 | AfuguAfaccAfaGfdAGfdAGfdTAdTUdCcdAsu | AS1059 | dAUdGGdAaaTafdCfUfcUfuGfUfuAfcAfusGfsa | 0.09 | 0.27 | 0.7 | 0.054 |
| D1060 | S1060 | adTguAfAdccdAdAgagdTadTudCcasdT | AS1060 | adTdGgdAadTadCafTdCuudGdGuudAdCadTsgsa | 0.11 | 0.37 | 0.66 | 0.056 |
| D1061 | S1061 | AfuGfuAfaCfcAfAfgGfdAdAGuAfuiUfcdCdAsUf | AS1061 | adTdGGfaAfuAfdCdTcUfcUfuGfGfuUfaAfcAfusGfsa | 0.1 | 0.31 | 0.77 | 0.059 |
| D1062 | S1062 | AfuguAfaccAfaGfdAGfdAGfdTAdTUdCcdAsu | AS1062 | aUfgGfaAfuAfUfcUfcUfuGfgUfuAfcAfusGfsa | 0.1 | 0.27 | 0.65 | 0.059 |
| D1063 | S1063 | adTdGuadAdCccdAdGagdTdAuudCdCasu | AS1063 | dAdTggdAdAuadCdTcudTdGgudTdAcadTsdGsa | 0.12 | 0.44 | 0.82 | 0.064 |
| D1064 | S1064 | AfuGfuAfaCfcAfaGfdAGfdTdAuUfcdAsUf | AS1064 | adTdGGfaAfdTdAcUfcUfuGfGfuAfcAfusGfsa | 0.12 | 0.32 | 0.83 | 0.064 |
| D1065 | S1065 | AfuguAfaccAfaGfdAGfdTadTudCcdAsu | AS1065 | dAUdGGdAadTafcUfcUfuGfuUfgUfuAfcAfusGfsa | 0.13 | 0.34 | 0.72 | 0.066 |
| D1066 | S1066 | AfuguAfaCfcAfaGfaGfudAdTUfcdCdAsUf | AS1066 | adTdGGfadAdTafUfcUfuGfuGfuUfaAfcAfusGfsa | 0.11 | 0.33 | 0.72 | 0.067 |
| D1067 | S1067 | AfuguAfaccAfaCfAfaGfdTAdTUdCcdAsu | AS1067 | aUfgGfaAfuAfcUfcUfuGfuUfgUfuAfcAfusGfsa | 0.11 | 0.37 | 0.62 | 0.070 |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1068 | S1068 | AfuguAfaccAfaGfaGfaGfQTAdTUdCcdAsu | AS1068 | dAUdGgdAAuAfcUfcUfuGfGfUfUfAfCfAfusGfsa | 0.16 | 0.33 | 0.64 | 0.072 |
| D1069 | S1069 | aUfGfuaAfcCfccAfGfagUfAfuuCfCfasu | AS1069 | AfUfggAfAfuaCfUfcuUfgGfguUfAfcaUfsGfsa | 0.14 | 0.43 | 0.73 | 0.074 |
| D1070 | S1070 | AfuGfuAfcCfCfAfaGfaguAfuUfcCfasUf | AS1070 | aUfGfaAfuAfcCfUfcUfuggUfuAfcAfcaUfsGfsa | 0.08 | 0.42 | 0.94 | 0.075 |
| D1071 | S1071 | UfgGfgAfuuuCfaUfGfuAfcCfaAfgsAf | AS1071 | ucfuUfgGfuUfaCfauGfaUfgAfAfAfuCfcCfasUfsc | 0.14 | 0.28 | 0.83 | 0.0797 |
| D1072 | S1072 | AfuGfuAfcCfcAfaGfAfGfuauUfcCfasUf | AS1072 | aUfgGfaAfuUfAfcucUfuGfuGftuAfcAfusGfsa | 0.05 | 0.26 | 0.8 | 0.082 |
| D1073 | S1073 | AfuGfuAfcCfcAfaGfaGdTdAdTUfccfasUf | AS1073 | aUfgGfadAdTdAdCfUfcUfuGfgUfuAfcAfusGfsa | 0.12 | 0.41 | 0.73 | 0.083 |
| D1074 | S1074 | AfUfguAfAfccAfAfgaGfUfauUfCfasUf | AS1074 | aUfGfaAfUfacUfcUfuuGfGfuuAfcAfausGfsa | 0.14 | 0.44 | 0.75 | 0.086 |
| D1075 | S1075 | AfuGfuAfcCfcAfaGfcAfaGfudAdTdAdCfasUf | AS1075 | aUfgGfdAdAdTdAcUfcUfuGfgUfuAfcAfusGfsa | 0.1 | 0.41 | 0.72 | 0.088 |
| D1076 | S1076 | AfuGfuAfcCfcAfaGfaGfudAdTdCCfasUf | AS1076 | aUfgGfdAdAdTAfcUfcUfuGfgUfuAfcAfusGfsa | 0.15 | 0.45 | 0.86 | 0.088 |
| D1077 | S1077 | AfuGfuAfcCfcAfaGfaGfuAfuUfcCfasu | AS1077 | AfUfGfaAfuAfcUfcUfuGfgUfuAfcAfusGfsa | 0.08 | 0.46 | 0.95 | 0.092 |
| D1078 | S1078 | AfuGfuAfcCfcAfaGfaGfuAfuUfcCfasUf | AS1078 | dAUdGgdAaTAfcUfcUfuGfgUfuAfcAfusGfsa | 0.09 | 0.32 | 0.76 | 0.093 |
| D1079 | S1079 | AfuguAfaccAfaGfaGfTadTudCcdAsu | AS1079 | aUfgGfAfaAfuAfcUfcucUfuGfgUfuAfcAfusGfsa | 0.14 | 0.38 | 0.76 | 0.095 |
| D1080 | S1080 | AfuGfuAfcCfcAfaGfaGfuAfiuuCfCfasUf | AS1080 | aUfGfaAfAfafcucUfuGfgUfuAfcAfusGfsa | 0.05 | 0.42 | 0.86 | 0.099 |
| D1081 | S1081 | AfuGfuAfcCfcAfaGfaGfaUfuUfdCdCdAsdT | AS1081 | dAdTdGdGaAfuAfcUfudACUfcUfuGfUfUfAfCfAfusgsa | 0.17 | 0.47 | 0.9 | 0.105 |
| D1082 | S1082 | AfuGfuAfccaagaguAfiuUfcCfasUf | AS1082 | aUfgGfaAfudACfudACUfcUfuGfGGfudTAfcAfAfusGfsa | 0.12 | 0.44 | 0.83 | 0.106 |
| D1083 | S1083 | AfuGfuAfcCfcAfaGfadTaUfcCfasUf | AS1083 | adTdGGfaAfudATdAcUfcUfuGfgUfuAfcAfusGfsa | 0.11 | 0.34 | 0.74 | 0.109 |
| D1084 | S1084 | AfuGfuAfcCfAfaGfagfauauUfcCfasUf | AS1084 | aUfgGfaAfuUfAfcUfcUfuGfguuAfcAfusGfsa | 0.1 | 0.45 | 0.93 | 0.117 |
| D1085 | S1085 | AfuGfuAfcCfcAfaGfaGfuauUfcCfasUf | AS1085 | aUfgGfaAfuUfAfcUfcUfuGfgUfuacAfusGfsa | 0.07 | 0.42 | 0.78 | 0.120 |
| D1086 | S1086 | aUfGfuAfcCfcAfAfaGfaGfuAfuUfcCfasUf | AS1086 | AfuGfgAfAfuUfcUfuuGfGfuuAfcAfusgsa | 0.17 | 0.45 | 0.83 | 0.1197 |
| D1087 | S1087 | AfuGfuAfcCfcAfaGfaGfuAfuUfcCfasu | AS1087 | AfUfggAfAfuacUfcUfCfuUfAfcAfusGfsa | 0.05 | 0.3 | 0.7 | 0.120 |
| D1088 | S1088 | AfuGfuAfcCfcAfaGfaGfaAfuUfcCfasUf | AS1088 | aUfgGfaAfuAfudACfUfcUfuGfuUfuAfcAfusgsa | 0.11 | 0.46 | 0.8 | 0.120 |
| D1089 | S1089 | AfuGfuAfcCfcAfaGfaGfuauUfcCfasUf | AS1089 | aUfgGfAfauacUfcUfuuGfguUfuAfcAfusGfsa | 0.14 | 0.49 | 0.85 | 0.122 |
| D1090 | S1090 | AfuGfuAfcCfcAfaGfaGfuauUfcCfasUf | AS1090 | aUfgGfaAfuAfcUfcUfuGfgUfuAfcAfusGfsa | 0.1 | 0.41 | 0.85 | 0.125 |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1091 | S1091 | AfuguAfaccAfaGfaGfQTAdTudCcdAsu | AS1091 | aUfgGfaAfuAfcUfcUfuGfgUfuAfcAfusGfsa | 0.16 | 0.38 | 0.77 | 0.125 |
| D1092 | S1092 | AfuGfuAfafcAfcFcAfaGfaGfaGfuAfaUfcCfasu | AS1092 | AfUfgGfaAfuAfcUfcucUfuGfgUfuAfcAfusGfsa | 0.05 | 0.31 | 0.93 | 0.126 |
| D1093 | S1093 | auGfuAfafcAfcTcAfaGfaGfaGfuAfaUfcCfasUf | AS1093 | aUfgGfaAfuAfcUfcucUfuGfgUfuAfcAfUfsGfsa | 0.06 | 0.33 | 0.9 | 0.135 |
| D1094 | S1094 | AfuGfuAfafcAfcTcAfaGfaGfaGfuAfaUfcCfasUf | AS1094 | aUfgGfaAfuAfacUfcUfcUfuGfgUfuAfcAfusGfsa | 0.07 | 0.39 | 0.85 | 0.142 |
| D1095 | S1095 | AfuGfuAfafcAfcTcAfaGfaGfaGfuAfaUfcCfasUf | AS1095 | aUfgGfaAfuAfcucUfcUfuGfgUfuAfcAfusGfsa | 0.09 | 0.39 | 0.76 | 0.146 |
| D1096 | S1096 | AfuGfuAfafAfcTcAfaGfaGfaGfuAfuucCfasUf | AS1096 | aUfgGfaAfAfuAfcUfcUfuGfgUfuAfcAfusGfsa | 0.06 | 0.38 | 0.85 | 0.147 |
| D1097 | S1097 | AfuGfuAfafAfcTcAfaGfaGfaGfuAfaUfcCfasUf | AS1097 | aUfgGfaAfAfuAfcUfcUfuGfgUfuacAfusGfsa | 0.12 | 0.47 | 0.87 | 0.147 |
| D1098 | S1098 | AfuGfuAfafAfcTcAfaGfaGfaGfuAfUfUfcCfasUf | AS1098 | aUfgGfaauAfcUfcUfuGfgUfuAfcAfusGfsa | 0.06 | 0.42 | 0.85 | 0.151 |
| D1099 | S1099 | AfuGfuAfafAfcTcAfaGfaGfaGfuAfaUfcCfasUf | AS1099 | dAUdGgGdAadTAfdCfcUfuGfgUfuAfcAfaGfsa | 0.16 | 0.41 | 0.85 | 0.152 |
| D1100 | S1100 | AfuguAfafcAfacAfaGfaGfaGfuAfaUfcCfasUf | AS1100 | aUfGfGfaAfuAfcucUfuGfgUfuAfcAfusGfsa | 0.15 | 0.48 | 0.72 | 0.152 |
| D1101 | S1101 | AfuGfuAfafcAfcTcAfaGfaGfaGfuAfiuCfasUf | AS1101 | aUfGfGfaAfuAfcucUfuGfgUfuAfcAfusGfsa | 0.06 | 0.38 | 0.94 | 0.158 |
| D1102 | S1102 | AfuGfuAfafaccaagaguAtuFcCfasUf | AS1102 | aUfgGfaAfuAfdCfuCfdTudGdGuUfacAfusGfsa | 0.21 | 0.45 | 0.89 | 0.162 |
| D1103 | S1103 | AfuGfuAfafcCfcAfafcAfaGfuAfuUfcCfasUf | AS1103 | aUfgGfaAfuAfcUfcUfuggUfuAfcAfusGfsa | 0.14 | 0.49 | 0.95 | 0.163 |
| D1104 | S1104 | AfuGfuAfafaccAfaCfcAfaGfuAfafucCfasUf | AS1104 | aUfgGfaAfuacUfcUfcUfuGfgUfuAfcAfusGfsa | 0.06 | 0.36 | 0.92 | 0.163 |
| D1105 | S1105 | AfuGfuAfafcAfcTcAfaGfaGfuAfUucCfasUf | AS1105 | aUfgGfAfAfuAfcUfcUfuGfgUfuAfcAfusGfsa | 0.1 | 0.45 | 0.84 | 0.167 |
| D1106 | S1106 | AfuGfuAfuaaCfcAfaGfaGfuAfaUfcCfasUf | AS1106 | aUfgGfaAfuAfcucUfuGfgUfuAfcAfusGfsa | 0.09 | 0.43 | 0.91 | 0.170 |
| D1107 | S1107 | AfuGfuAfuaCfaAfaGfaGfuAfaUfcCfasUf | AS1107 | aUfgGfaAfuAfcUfcUfuGfgUfuAfcAfusGfsa | 0.09 | 0.46 | 1 | 0.171 |
| D1108 | S1108 | AfuguAfaccAfaGfaGfdTadTudCcdAsu | AS1108 | aUfgGfaAfuAfcUfcUfuGfgUfuAfcAfusGfsa | 0.11 | 0.39 | 0.71 | 0.176 |
| D1109 | S1109 | AfuGfuAfafaCfcAfaGfaGfuAfcCfasUf | AS1109 | aUfgGfaAfuAfcUfcUfuGfgUfuacAfusGfsa | 0.1 | 0.43 | 0.9 | 0.180 |
| D1110 | S1110 | AfuGfuAfafcAfcTcAfagUfaUfcCfasUf | AS1110 | aUfgGfaauAfcUfCfUfUfuGfgUfuAfcAfusGfsa | 0.06 | 0.42 | 0.88 | 0.182 |
| D1111 | S1111 | AfuGfuAfafcAfcfcAfaGfaGfuAfUfcCfasUf | AS1111 | dAUdGgGdAAuAfcUfcUfuGfgUfuAfcAfusGfsa | 0.18 | 0.49 | 0.79 | 0.183 |
| D1112 | S1112 | AfuGfuAfafcaAfaCfaGfaGfuAfUfcCfasUf | AS1112 | aUfgGfaAfuAfcUfcUfuGfGfUfuacAfusGfsa | 0.14 | 0.48 | 0.85 | 0.195 |
| D1113 | S1113 | AfuGfuAfafcfcAfaguAfuFcCfasUf | AS1113 | aUfgGfaAfuAfCfUfcUfuGfgUfuAfcAfusGfsa | 0.09 | 0.41 | 0.85 | 0.201 |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1114 | S1114 | auGfuAfaCfcAfaGfaGfuAfaUfcCfasUf | AS1114 | aUfgGfaAfuacUfCfuGfgUfuAfcAfUfsGfsa | 0.05 | 0.44 | 0.94 | 0.201 |
| D1115 | S1115 | AfuguAfaCfcAfaGfaGfuAfaUfcCfasUf | AS1115 | aUfgGfaAfuacUfCfuGfgUfuAfcAfCfAfusGfsa | 0.08 | 0.41 | 0.96 | 0.204 |
| D1116 | S1116 | AfuGfuAfaCfcAfaGfaGfuAfaUfcCfasUf | AS1116 | adTdGfadAdTAfcUfCfuGfgUfuAfcAfusGfsa | 0.15 | 0.47 | 0.79 | 0.208 |
| D1117 | S1117 | AfuGfuaaCfcAfaGfaGfuAfaUfcCfasUf | AS1117 | aUfgGfaAfuacUfcUfgGfgUfuAfcAfusGfsa | 0.08 | 0.42 | 0.92 | 0.224 |
| D1118 | S1118 | auguaaccaaguauuccasu | AS1118 | AfUfGfGfAAfuAfCfUfCfUfGfGfUfuAfCfAfUfsgsa | 0.19 | 0.5 | 0.87 | 0.303 |
| D1119 | S1119 | AfuGfuAfaCfcAfaGfaGfuAfaUfcCfasUf | AS1119 | aUfgGfaAfuAfcUfcUfuGfcUfuAfcAfusGfsa | 0.14 | 0.55 | 0.89 | |
| D1120 | S1120 | AfuGfuAfaCfcAfaGfaGfuAfaUfcCfasUf | AS1120 | aUfgGfaAfuAfcUfcUfuGfgUfuAfcAfusGfsa | 0.19 | 0.63 | 0.72 | |
| D1121 | S1121 | AfuGfuAfaccAfaGfaGfuAfaUfcCfasUf | AS1121 | aUfgGfaAfuAfaCfcUfcUfuGfgUfuAfcAfusGfsa | 0.14 | 0.61 | 0.91 | |
| D1122 | S1122 | AfuGfGfuAfaCfcAfaGfaGfuAfaUfcCfasUf | AS1122 | aUfGfGfaAfuAfcUfcUfuGfcUfuAfcAfusGfsa | 0.14 | 0.54 | 0.95 | |
| D1123 | S1123 | auGfuAfaCfcAfaGfaGfuAfaUfcCfasUf | AS1123 | aUfgGfaAfuAfcUfcUfuGfguuAfcAfusGfsa | 0.13 | 0.61 | 0.97 | |
| D1124 | S1124 | AfuGfuAfaCfcAfaGfaGfuAfaUfcCfasUf | AS1124 | aUfgGfaauAfAfcUfcUfuGfgUfuAfcAfusGfsa | 0.14 | 0.56 | 0.94 | |
| D1125 | S1125 | AfuGfuAfaGfcaaGfaGfuAfaUfcCfasUf | AS1125 | aUfgGfaAfuAfcUfcUfuGfgUfuAfcAfusGfsa | 0.21 | 0.74 | 0.95 | |
| D1126 | S1126 | AfUfGfuAfaCfaGfaGfaGfauucCfasUf | AS1126 | aUfgGfaAfuAfcUfcUfuGfgUfuAfcausGfsa | 0.2 | 0.69 | 0.91 | |
| D1127 | S1127 | AfuguAfaCfcAfaGfaGfuAfaUfcCfasUf | AS1127 | aUfgGfaAfuAfcUfcUfuGfguuAfcAfusGfsa | 0.17 | 0.7 | 0.96 | |
| D1128 | S1128 | AfuGfuAfaCfcAfaGfaGfuAfaUfcCfasUf | AS1128 | aUfgGfaAfuAfcUfcUfuGfcUfuAfcausGfsa | 0.19 | 0.62 | 0.85 | |
| D1129 | S1129 | AfuGfuAfaCfcAfaGfadfcaUfUfcCfasUf | AS1129 | aUfggaAfuAfcUfcUfuGfgUfuAfcAfusGfsa | 0.23 | 0.76 | 0.98 | |
| D1130 | S1130 | AfuGfuAfaCfcAfafgaGfuAfuUfcCfasUf | AS1130 | aUfgGfaAfuAfcUfcUfuGfgUfuAfcAfusGfsa | 0.21 | 0.64 | 0.9 | |
| D1131 | S1131 | AfuuGfuAfAfCfcAfaGfuAfaUfcCfasUf | AS1131 | aUfgGfaAfuAfcUfcUfuGfguuAfcAfusGfsa | 0.17 | 0.7 | 1.01 | |
| D1132 | S1132 | AfuGfuAfaAfCfcAfaGfaGfuAfuUfcCfasUf | AS1132 | aUfgGfaAfuAfcUfcUfuGfguuacAfusGfsa | 0.17 | 0.58 | 0.87 | |
| D1133 | S1133 | AfuGfuAfaAfCfcAfaCfaGfuAfaUfcCfasUf | AS1133 | aUfgGfaAfuAfcUfcUfuGfgUfuacAfusGfsa | 0.33 | 0.89 | 1.05 | |
| D1134 | S1134 | auGfuAfaCfcAfaGfagauAfuUfcCfasUf | AS1134 | augGfaAfuAfcUfcUfuGfgUfuAfcausGfsa | 0.16 | 0.64 | 0.96 | |
| D1135 | S1135 | AfuGfuAfaAfCfcAfaGfagauAfuUfcCfasUf | AS1135 | aUfgGfaAfuAfcUfCfUfuGfgUfuGfuacAfusGfsa | 0.12 | 0.53 | 0.96 | |
| D1136 | S1136 | AfuGfuAfAfCfcAfagaGfuAfuUfcCfasUf | AS1136 | aUfgGfaAfuAfcUfCfUfuGfguuAfcAfusGfsa | 0.16 | 0.58 | 0.98 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1137 | S1137 | AfuGfuAfAfCfcAfaGfaGfuAfgUfuUfcCfasUf | AS1137 | aUfgGfaAfuAfcUfcUfuGfguuAfcAfusGfsa | 0.16 | 0.6 | 0.91 | |
| D1138 | S1138 | AfuGfuAfAfCfcAfaGfaGfaGfuUfgUfuUfcCfasUf | AS1138 | aUfgGfaAfuAfcUfcUfuGfugUfuAfcAfusGfsAf | 0.1 | 0.54 | 0.91 | |
| D1139 | S1139 | AfuUfGfuAfAfCfcAfagaGfuUfgUfuUfcCfasUf | AS1139 | aUfgGfaAfuAfcUfCfUfuCfgUfuAfcAfusGfsa | 0.24 | 0.68 | 0.98 | |
| D1140 | S1140 | AfuGfuAfAfCfcAfagaGfuUfgUfuUfcCfasUf | AS1140 | aUfgGfaAfuAfcUfcUfuGfgUfuAfcAfusGfsa | 0.13 | 0.75 | 0.9 | |
| D1141 | S1141 | AfuGfuAfAfCfcAfaGfagaAfuUfgUfuUfcCfasUf | AS1141 | aUfgGfaAfuAfcUfUfcUfuGfguuAfcAfusGfsa | 0.15 | 0.52 | 1.05 | |
| D1142 | S1142 | AfuGfuAfCfCfAfaGfaGfuAfuUfcUfcCfasUf | AS1142 | aUfgGfaAfuAfcUfcUfuGfguuGfuAfcAfusGfsa | 0.16 | 0.66 | 0.89 | |
| D1143 | S1143 | auGfuAfaCfaCfaAfaGfaGfuuUfgUfuUfcCfasUf | AS1143 | aUfgGfaAfuAfcUfcUfuGfgUfuAfcAfUfsGfsa | 0.12 | 0.51 | 0.89 | |
| D1144 | S1144 | AfuGfuAfaCfcAfaGfaGfuUfgUfuUfcCfasUf | AS1144 | aUfgGfaAfuAfcUfcUfuGfgUfuAfcAfusGfsa | 0.25 | 0.71 | 0.95 | |
| D1145 | S1145 | AfuGfUfAfaCfcAfaGfaGfuUfgUfuUfcCfasUf | AS1145 | aUfgGfaAfuAfcUfcUfuGfgUfuGfcAfusGfsa | 0.17 | 0.74 | 0.98 | |
| D1146 | S1146 | AfuGfuAfaCfcAfAfGfaGfuAfuUfcCfasUf | AS1146 | aUfgGfaAfuAfcUfcUfuGfguuacAfusGfsa | 0.11 | 0.51 | 0.86 | |
| D1147 | S1147 | AfuGfuAfaCfcAfaGfaGfuUfgUfuAfcCfcasUf | AS1147 | aUfgGfaAfuAfcUfcUfuGfgUfuAfcAfusGfsa | 0.1 | 0.52 | 0.83 | |
| D1148 | S1148 | AfuGfuAfaccAfaGfaGfuUfgUfuUfcCfasUf | AS1148 | aUfgGfaAfuAfcUfcUfuGfGfUfuAfcAfusGfsa | 0.14 | 0.63 | 0.98 | |
| D1149 | S1149 | AfuGfuAfAfCfcAfaGfagGfuUfuUfcCfasUf | AS1149 | aUfgGfaAfuAfcUfcUfuGfguuAfcAfusGfsa | 0.13 | 0.58 | 0.88 | |
| D1150 | S1150 | AfuGfuaaCfcAfaGfaGfuUfgUfuUfcCfasUf | AS1150 | aUfgGfaAfuAfcUfcUfuGfgUfuAfcAfusGfsa | 0.15 | 0.62 | 0.94 | |
| D1151 | S1151 | AfuUfGfuaaCfcAfaGfaGfuUfgUfuUfcCfasUf | AS1151 | aUfgGfaAfuAfcUfcUfuGfgUfuAfcausGfsa | 0.18 | 0.73 | 0.94 | |
| D1152 | S1152 | auGfuUfAfaCfcAfaGfaGfuUfgUfuUfcCfasUf | AS1152 | aUfgGfaAfuAfcUfcUfuGfgUfuacAfUfsGfsa | 0.13 | 0.53 | 0.97 | |
| D1153 | S1153 | AfuGfuAfAfCfcAfaGfaGfuUfgUfuuccasUf | AS1153 | aUfgGfaAfuAfcUfcUfuGfguuAfcAfusGfsa | 0.13 | 0.53 | 0.98 | |
| D1154 | S1154 | UfgGfuAfAfuCfuUfuCfaUfgAfaAfcCfaAfgsAf | AS1154 | uCfuUfgGfuuaCfaUfgAfaAfAfucCfcCfasUfsc | 0.09 | 0.5 | 0.78 | |
| D1155 | S1155 | UfgGfgAfuuuCfaUfgUfaAfcCfaAfgsAf | AS1155 | uCfuUfgGfuuaaCfaUfgAfaAfAfAfucCfasUfsc | 0.13 | 0.62 | 0.89 | |
| D1156 | S1156 | UfgGfgAfuuuCfaUfgUfUfaAfcCfaAfgsAf | AS1156 | uCfuUfgGfuuacaUfgAfaUfgAfaUfcCfasUfsc | 0.12 | 0.65 | 0.85 | |
| D1157 | S1157 | UfgGfgAfuUfuCfaUfgUfAfAfcCfaAfgsAf | AS1157 | uCfuUfgGfuuaCfaUfgAfaAfAfucCfcCfasUfsc | 0.11 | 0.54 | 0.85 | |
| D1158 | S1158 | UfgGfgAfuuuCfaUfgUfAfAfcCfaAfgsAf | AS1158 | uCfuUfgGfuuaCfaUfgAfaUfcCfcCfasUfsc | 0.13 | 0.53 | 0.8 | |
| D1159 | S1159 | UfgGfggAfUfuUfcAfuGfuAfAfccAfAfgsAf | AS1159 | uCfuugGfuuAfcAfuGaAfauCfCfcasUfsc | 0.59 | 0.89 | 0.81 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1160 | S1160 | UfGfggAfUfuuCfaUfgUfAfAfcCfaAfgsAf | AS1160 | uCfuUfgGfuuaCfaUfgGfaAfauCfCfcasUfsc | 0.16 | 0.72 | 0.9 | |
| D1161 | S1161 | UfgGfgAfuUfucaUfgUfaAfcCfaAfgsAf | AS1161 | uCfuUfgGfuUfacaUfGfaAfuCfcCfasUfsc | 0.27 | 0.69 | 0.86 | |
| D1162 | S1162 | AfuGfuAfaCfcaaGfaGfuAfUfUfUfcCfasUf | AS1162 | aUfgGfaAfuacAfcUfcUfgUfgUfaAfcfasUfsGfsa | 0.12 | 0.6 | 0.95 | |
| D1163 | S1163 | AfuGfuAfaccAfaGfaGfuAfUfUfUfcCfasUf | AS1163 | aUfgGfaAfaauAfcUfcUfuGfgUfuAfcAfusGfsa | 0.05 | 0.56 | 1.02 | |
| D1164 | S1164 | AfuGfuAfaCfcAfagaGfUfAfUfUfUfcCfasUf | AS1164 | aUfgGfaAfuacUfcUfcUfgUfuAfcAfusGfsa | 0.13 | 0.55 | 1 | |
| D1165 | S1165 | AfuGfuAfaCfcaaGfaGfuAfUfUfUfcCfasUf | AS1165 | aUfgGfaAfuaUfcUfcUfgUfuAfcAfusGfsa | 0.09 | 0.6 | 0.97 | |
| D1166 | S1166 | AfuGfuAfaCfcfAfaGfaGfuAfUfUfcCfasUf | AS1166 | aUfgGfaAfuAfcUfcUfuggUfuAfCfAfusGfsa | 0.15 | 0.59 | 0.91 | |
| D1167 | S1167 | AfuGfuAfaCfcAfagaGfuAfUfUfUfcCfasUf | AS1167 | aUfgGfaAfuAfcUfcUfuUfugUfaAfcfAfusGfsa | 0.11 | 0.59 | 1 | |
| D1168 | S1168 | AfuGfuAfaCfcfAfagaGfuAfUfUfUfcCfasUf | AS1168 | aUfgGfaAfuAfcUfcUfcUfuGfgUfuAfcAfusGfsa | 0.13 | 0.57 | 0.94 | |
| D1169 | S1169 | auGfuAfaCfcAfaGfaGfuAfUfUfUfcCfasUf | AS1169 | aUfgGfaAfaUfAfcUfcUfuGfgUfuAfcAfusGfsa | 0.08 | 0.5 | 0.9 | |
| D1170 | S1170 | AfuGfuAfaCfcAfaGfaGfuAfUfUfUfcCfasUf | AS1170 | aUfgGfaAfuAfcUfcUfcUfgGfuAfcAfusGfsa | 0.06 | 0.53 | 0.91 | |
| D1171 | S1171 | auGfuAfaCfcAfaGfaGfuAfUfUfUfcCfasUf | AS1171 | aUfgGfaaAfuAfcUfcUfcUfuGfgUfuAfcAfusGfsa | 0.07 | 0.56 | 0.89 | |
| D1172 | S1172 | AfGfuAfaCfcfAfaGfaGfuAfUfUfUfcCfasUf | AS1172 | aUfgGfaAfuAfaCfuCfUfuggUfuAfCfAfusGfsa | 0.13 | 0.59 | 0.98 | |
| D1173 | S1173 | AfuGfuAfaCfcfAfaGfaGfuAfUfUfuucCfasUf | AS1173 | aUfgGfaAfuAfcUfcucUfUfUfgGfuAfcAfusGfsa | 0.2 | 0.65 | 1.03 | |
| D1174 | S1174 | AfuGfuAfaCfcfAfaGfaGfuAfUfUfUfcCfasUf | AS1174 | aUfgGfaAfuAfcUfcUfgUfuGfuAfcAfusGfsa | 0.07 | 0.51 | 0.95 | |
| D1175 | S1175 | AfuGfuAfaCfcfAfaGfaGfuAfUfUfUfcCfAfsUf | AS1175 | aUfgGfaAfuAfcUfcUfcUfuGfgUfuAfcAfusGfsa | 0.2 | 0.53 | 0.76 | |
| D1176 | S1176 | auGfuAfaCfcAfaGfaGfaGfuAfUfUfUfcCfasUf | AS1176 | augGfaAfaAfuAfcUfcUfcUfuGfgUfuAfcAfusGfsa | 0.74 | 0.98 | 0.81 | |
| D1177 | S1177 | AfuGfuAfaCfcfAfaGfaGfuAfUfuucCfAfsUf | AS1177 | aUfgGfaAfuAfcUfcUfcUfuGfgUfuAfcAfusGfsa | 0.43 | 0.64 | 0.88 | |
| D1178 | S1178 | auguaaccAfaGfaGfuAfUfUfcCfasUf | AS1178 | aUfgGfaAfuAfcUfcUfgUfgUfUfAfcAfusGfsa | 0.17 | 0.49 | 0.81 | |
| D1179 | S1179 | AfuGfuAfaCfcfAfaGfaGfuAfUfUfCfCfasUf | AS1179 | aUfggaAfuAfAfcUfcUfcUfgUfuGfUfAfcAfusGfsa | 0.22 | 0.65 | 0.73 | |
| D1180 | S1180 | AfugUfAfaCfcfAfaGfaGfuAfUfUfuCfAfsUf | AS1180 | augGfaAfuAfAfcUfcUfcUfuGfgUfuAfcAfusGfsa | 0.6 | 1.09 | 0.8 | |
| D1181 | S1181 | auGfuAfaCfcAfaGfaGfuAfUfccasu | AS1181 | aUfgGfaAfAfAfcUfcUfuGfuAfcAfusGfsa | 0.3 | 0.78 | 0.78 | |
| D1182 | S1182 | auguaaccaaGfaGfuAfUfUfcCfasUf | AS1182 | aUfgGfaAfAfAfcUfcUfuGfuGfuUfaAfcAfusGfsa | 0.35 | 0.73 | 0.84 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1183 | S1183 | AfuGfuAfaccAfaGfaGfuAfuUfCfCfasUf | AS1183 | aUfggaAfuAfcUfcUfuGfcGfufuAfcAfusGfsa | 0.19 | 0.6 | 0.94 | |
| D1184 | S1184 | AfuGfuaaCfcAfaGfuAfuUfCfCfAfsUf | AS1184 | augGfaAfuAfcUfcUfuGfguGfufuAfCfAfusGfsa | 0.61 | 1.08 | 0.8 | |
| D1185 | S1185 | auGfuAfaCfcAfaGfaGfuAfuuccasu | AS1185 | aUfGfaaAfuAfcUfcUfugGfuGfufuAfcAfusGfsa | 0.16 | 0.52 | 0.72 | |
| D1186 | S1186 | auguaaccagaGfuAfuUfcCfasUf | AS1186 | aUfGfaAfuAfcUfcUfuGfgUfufuAfcAfusGfsa | 0.2 | 0.53 | 0.74 | |
| D1187 | S1187 | AfuGfuAfaCfcaaGfaGfuAfuUfCfCfAfsUf | AS1187 | aUfggaAfuAfcUfcUfuGfgUfGfufuAfcAfusGfsa | 0.34 | 0.66 | 0.85 | |
| D1188 | S1188 | AfuGfuAfaccAfaGfuAfuUfCfCfAfsUf | AS1188 | augGfaAfuAfcUfcUfuGfUfAfcAfusGfsa | 0.61 | 0.98 | 1.02 | |
| D1189 | S1189 | AfuGfuAfcCfcAfaGfaGfuAfuuccasu | AS1189 | aUfgGfaaAfuAfcUfcUfugGfuAfcAfusGfsa | 0.3 | 0.73 | 0.85 | |
| D1190 | S1190 | auguaaccaagaguauuccasu | AS1190 | aUfgGfaaAfuAfcUfcUfugGfuAfcAfusGfsa | 0.28 | 0.69 | 0.78 | |
| D1191 | S1191 | AfuGfuAfcCfcAfaGfaGfuAfuUfCfCfAfsUf | AS1191 | aUfGfaaAfuAfcUfcUfugGfudTadCadTsgsa | 0.33 | 0.88 | 0.64 | |
| D1192 | S1192 | AfuGfuAfcCfcAfaAgaGfaGfuAfuUfCfCfAfsUf | AS1192 | auGfGfaaAfuAfcUfcUfuGfuGfufuAfcAfusGfsa | 0.31 | 0.64 | 0.83 | |
| D1193 | S1193 | AfuGfuAfcCfcaaGfaGfuAfuUfCfCfAfsUf | AS1193 | aUfGfuAfaAfuAfcUfcUfuGfgUfufuAfcAfusGfsa | 0.64 | 0.82 | 0.92 | |
| D1194 | S1194 | AfuGfuAfcCfcAfaGfaGfuauuccasu | AS1194 | aUfgGfaAfuAfcUfcUfuGfgUfufuAfcAfusGfsa | 0.21 | 0.62 | 0.77 | |
| D1195 | S1195 | AfuGfuAfcCfcAfaGfuAfuUfcCfAfsUf | AS1195 | aUfGfGfaAfuAfcUfcUfuGfGfUfuAfcAfAfusGfsa | 0.17 | 0.7 | 0.95 | |
| D1196 | S1196 | AfuGfuAfacCfcAfagaGfuAfuUfCfCfAfsUf | AS1196 | augGfaAfuAfCfUfcUfuGfgUfuAfcAfusGfsa | 0.19 | 0.71 | 0.65 | |
| D1197 | S1197 | AfuGfuAfcCfcAfagaGfuAfuUfcCfAfsUf | AS1197 | augGfaAfuAfCfUfcUfuGfgUfuAfcAfusGfsa | 0.64 | 0.82 | 0.93 | |
| D1198 | S1198 | auguAfcCfaAfaGfuAfuAfuUfccasu | AS1198 | augGfaAfuAfcUfcUfuGfgUfuAfcAfusGfsa | 0.19 | 0.65 | 0.72 | |
| D1199 | S1199 | AfuGfuAfcCfaAfaGfaGfuaUfcCfAfsUf | AS1199 | aUfggaAfuAfcUfcUfuGfgUfuAfcAfusGfsa | 0.15 | 0.52 | 0.64 | |
| D1200 | S1200 | AfuGfuAfcCfaAfaGfagUfAfuUfCfCfAfsUf | AS1200 | augGfaAfuAfcUfcUfuGfgUfuAfcAfusGfsa | 0.48 | 0.74 | 0.92 | |
| D1201 | S1201 | auguAfcCfaAfaGfaGfuAfuUfcCfasu | AS1201 | aUfggaAfuAfcUfcUfuGfgUfuAfcAfusGfsa | 0.17 | 0.71 | 0.77 | |
| D1202 | S1202 | AfuGfuAfcCfaAfcAfaGfaGfuauUfCfAfsUf | AS1202 | augGfaAfuAfCfUfcUfuauUfuAfcAfusGfsa | 0.43 | 0.69 | 0.85 | |
| D1203 | S1203 | auguaaCfcAfaGfaGfuAfuUfccasUf | AS1203 | augGfaAfuAfcUfcUfuGfgUfuAfcAfusGfsa | 0.14 | 0.61 | 0.76 | |
| D1204 | S1204 | AfuGfuAfcCfaAfaGfaAfuUfcCfasu | AS1204 | adTdGGfaAfudAdCfUfUfGfUfuGfuAfcAfusGfsa | 0.16 | 0.56 | 0.89 | |
| D1205 | S1205 | AfuGfuAfcCfcAfcAfaGfaGfdTdAdTccfasUf | AS1205 | aUfuGfAdAdTdAcUfcUfuGfGfuUfuAfcAfusGfsa | 0.13 | 0.57 | 0.9 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1206 | S1206 | AfuGfuAfaCfcAfaGfaGfuAfuUfccCfasUf | AS1206 | adTdGdGdAAfuAfcUfcUfuGfgUfuAfcAfusGfsa | 0.29 | 0.73 | 0.89 | |
| D1207 | S1207 | AfuGfuAfaCfcAfaGfaGfuAfuUfccCfasUf | AS1207 | adTdGGfaAfuAfdCdTcUfUfgUfuAfcAfusGfsa | 0.16 | 0.56 | 0.78 | |
| D1208 | S1208 | AfuGfuAfaCfcAfaGfaGfuAfuUfccCfasUf | AS1208 | aUfdGdGdAdAuAfcUfcUfuGfgUfuAfcAfusGfsa | 0.22 | 0.67 | 0.89 | |
| D1209 | S1209 | AfuguAfaccAfaGfaGfuAfuUfccCfasUf | AS1209 | aUfgGfaAfuAfcUfcUfuGfGfUfuAfcAfusGfsa | 0.14 | 0.55 | 0.78 | |
| D1210 | S1210 | AfuGfuAfaCfcAfaGfaGfuAfuUfccCfasUf | AS1210 | aUfgdGdAdAdTAfcUfcUfuGfgUfuAfcAfusGfsa | 0.14 | 0.5 | 0.84 | |
| D1211 | S1211 | AfuGfuAfaCfcAfaGfaGfuAfuUfccCfasUf | AS1211 | aUfgGfadAdTdAdCfcUfcUfuGfgUfuAfcAfusGfsa | 0.14 | 0.59 | 0.72 | |
| D1212 | S1212 | auguaaccaaGfaGfuAfuUfccCfasUf | AS1212 | aUfgGfaAfuAfcUfcUfugdGudTadCadTsgsa | 0.21 | 0.74 | 0.77 | |
| D1213 | S1213 | AfuGfuAfaCfcAfaGfaGfuAfudTdCdCdAsuUf | AS1213 | adTdGdGdAAfuAfcUfcUfuGfgUfuAfcAfusGfsa | 0.15 | 0.53 | 0.91 | |
| D1214 | S1214 | aUfgUfaAfccCfaAfgAfgUfauUfcCfcAfsu | AS1214 | aUfgGfaAfuAfcUfcUfuaGfguuGfuuAfcAfusGfsa | 0.12 | 0.71 | 0.87 | |
| D1215 | S1215 | AfuGfuAfaCfcAfaGfaGfuAfdTdTdCdCasUf | AS1215 | aUfdGdGdAdAuAfcUfcUfuGfgUfuAfcAfusGfsa | 0.18 | 0.67 | 0.97 | |
| D1216 | S1216 | AfuGfuAfaccaagaguAfuUfcCfasUf | AS1216 | aUfgGfaAfuacucuuggUfuAfcAfusgsa | 0.36 | 0.87 | 1.07 | |
| D1217 | S1217 | AfuGfuAfaccaagaguAfuUfcCfasUf | AS1217 | aUfgGfaAfuAfCfUfCfUfcUfuGfGfuuAfcAfusgsa | 0.37 | 0.73 | 1.03 | |
| D1218 | S1218 | AfUfguAfAfccAfAfgaGfuAfuUfcCfasUf | AS1218 | aUfgGfaAfUfaAfuCfuuGfGfuuAfCfauSfgsa | 0.23 | 0.42 | 0.84 | |
| D1219 | S1219 | AfuGfuAfaccaagaguAfuUfcCfasUf | AS1219 | aUfgGfaAfuaCfUfcUfuGfguuAfcAfusgsa | 0.43 | 0.71 | 1.03 | |
| D1220 | S1220 | AfuGfuAfaccaagaguAfuUfcCfasUf | AS1220 | aUfgGfaAfuAfcUfcUfuGfGfuuAfcAfusgsa | 0.37 | 0.63 | 0.99 | |
| D1221 | S1221 | AfuGfuAfaccaagaguAfuUfcCfasUf | AS1221 | aUfgGfaAfuAfcUfcUfuGfgUfgfGfuuAfacAfusgsa | 0.29 | 0.84 | 0.88 | |
| D1222 | S1222 | AfuGfuAfaccaagaguAfuUfcCfasUf | AS1222 | aUfgGfaAfuaCfucfuuUfgGfuuAfcAfsgsa | 0.31 | 0.8 | 0.99 | |
| D1223 | S1223 | auGfuAfAfaccaagaguAfuUfccAfsu | AS1223 | aUfgGfaAfuadCudCudTgdGuuAfcAfusgsa | 0.09 | 0.52 | 0.82 | |
| D1224 | S1224 | AfuGfuAfaccaagaguAfuUfcCfasUf | AS1224 | aUfgGfaAfuadCudCudTgdGuuAfcAfusgsa | 0.22 | 0.79 | 1 | |
| D1225 | S1225 | auGfuaAfcCfaAfguuAfuUfccCfasUf | AS1225 | aUfGfaAfAfuAfctuCfcUfuGfuAfcAfuUfaGfsa | 0.31 | 0.76 | 0.84 | |
| D1226 | S1226 | auGfuAfaccaagaguAfgAfuUfccCfasUf | AS1226 | aUfgGfaAfuadCfucdTUfgdGuuAfcAfusgsa | 0.26 | 0.64 | 0.87 | |
| D1227 | S1227 | augUfaaacTfaagAfguaUfuccAfsu | AS1227 | aUfgGfAfaAfuAfAfctuCfcUfuGfGfUfuAfcAfAfUfsGfsa | 0.33 | 0.79 | 0.81 | |
| D1228 | S1228 | AfuGfuAfaCfcAfaGfaGfuAfuUfccCfasUf | AS1228 | aUfgGfaAfuAfcUfcUfuGfGfuUfuAfcAfusGfsa | 0.464 | 0.932 | 0.978 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1229 | S1229 | AfuGfuAfaCfcAfaGfaGfuAfuUfcCfasUf | AS1229 | aUfgGfaAfaUfaUfcUfuGfgUfuGfaAfcAfusGfsa | 0.453 | 1.047 | 1.178 | |
| D1230 | S1230 | AfuGfuAfaCfcAfaGfaGfuAfuUfcCfasUf | AS1230 | aUfgGfaAfaUfaUfcUfcUfuGfuUfuGfaAfcAfusGfsa | 0.831 | 0.967 | 1.151 | |
| D1231 | S1231 | auGfuAfAfCfcAfaGfaGfuAfuUfcCfasu | AS1231 | AfUfgGfaAfuAfcUfcUfuGfguuAfcAfUfsGfsa | 0.09 | 0.5 | 1.07 | |
| D1232 | S1232 | AfuGfuAfaCfcAfaGfaGfuAfuUfcCfasu | AS1232 | AfUfgaAfaUfaUfcUfcUfuggUfuAfcAfusGfsa | 0.11 | 0.54 | 1.1 | |
| D1233 | S1233 | AfuGfuAfaCfcAfaGfaGfuAfuUfcCfasu | AS1233 | AfUfggaAfuAfcUfcUfuGfgUfuAfcAfusGfsa | 0.19 | 0.61 | 0.74 | |
| D1234 | S1234 | aUfgUfaAfcCfaAfgAfgfaUfaUfcCfAfsu | AS1234 | AfUfgAfaUfaCfuCfuUfgGfuUfaCfaUfsgsAf | 0.22 | 0.61 | 0.98 | |
| D1235 | S1235 | aUfgUfaAfcCfaAfgAfgfaUfaUfcCfAfsu | AS1235 | AfUfgAfaUfaCfuCfuUfgGfuUfaCfaUfsgsAf | 0.27 | 0.69 | 0.92 | |
| D1236 | S1236 | AfuGfuAfaCfcAfaGfaGfuAfuUfcCfasUf | AS1236 | AfUfgAfaUfaCfuCfuUfgGfuUfaCfaUfsgsAf | 0.54 | 1.08 | 0.8 | |
| D1237 | S1237 | augUfaAfccaAfgaGfguaUfcfcasu | AS1237 | AfUfgAfAfaUfAfcUfcUfuGfGfuUfaCfAfusgsa | 0.29 | 0.6 | 0.79 | |
| D1238 | S1238 | AfugUfaAfccaAfgaAfguaUfcfcasu | AS1238 | AfUfgAfgAfuAfAfcUfuGfgUfuaCfAfusgsa | 0.31 | 0.67 | 0.88 | |
| D1239 | S1239 | AfuGfuAfaCfcAfaGfaGfuAfuUfcCfasUf | AS1239 | dAUdGGdAAauAfcUfcUfuGfgUfuAfcAfusGfsa | 0.2 | 0.67 | 0.85 | |
| D1240 | S1240 | AfuGfuAfaCfcAfaGfaGfuAfuUfcCfasUf | AS1240 | dAUdgGdAauAfcUfcUfuGfgUfuAfcAfusGfsa | 0.23 | 0.58 | 0.68 | |
| D1241 | S1241 | AfuGfuAfaCfcAfaGfaGfuAfuUfcCfasUf | AS1241 | dAudGGdAauAfcUfcUfuGfgUfuAfcAfusGfsa | 0.25 | 0.65 | 0.78 | |
| D1242 | S1242 | AfuGfuAfaCfcAfaGfaGfuAfuUfcCfasUf | AS1242 | dAUdgGdAaTdAfcUfcUfuGfgUfuAfcAfusGfsa | 0.18 | 0.64 | 0.84 | |
| D1243 | S1243 | AfuGfuAfaCfcAfaGfaGfuAfuUfcCfasUf | AS1243 | dAUdGGdAAfcUfcUfuGfGfuAfcAfusGfsa | 0.19 | 0.72 | 0.87 | |
| D1244 | S1244 | AfuGfuAfaCfcAfaGfaGfuAfuUfcCfasUf | AS1244 | dAUdgGdAaTdQfcUfuGfuGfgUfuAfcAfusGfsa | 0.16 | 0.55 | 0.8 | |
| D1245 | S1245 | AfuGfuAfaCfcAfaGfaGfuAfuUfcCfasUf | AS1245 | dAUdGGdAAuAfcUfcUfuGfgUfuAfcAfusGfsa | 0.22 | 0.51 | 0.9 | |
| D1246 | S1246 | AfuGfuAfaCfcAfaGfaGfuAfuUfcCfasUf | AS1246 | dAudgGdAaTdAfcUfcUfuGfgUfuAfcAfusGfsa | 0.27 | 0.78 | 0.66 | |
| D1247 | S1247 | AfuGfuAfaCfcAfaGfaGfuAfuUfcCfasUf | AS1247 | dAdTdGGdAAfaUfcUfcUfuGfgUfuAfcAfusGfsa | 0.16 | 0.57 | 0.97 | |
| D1248 | S1248 | AfacAfuguUfcUfuGfdCudCudAudAsa | AS1248 | dTUdAudAgdAGfcAfaGfaFfaCfUfgUfuUfsu | 0.06 | 0.09 | 0.36 | 0.0047 |
| D1249 | S1249 | AfaCfaGfuGfuUfcUfcUfuGfCfUfcUfaUfasa | AS1249 | UfUfaUfagcAfagcAfaGaCfaCfUfgUfuUfsu | 0.06 | 0.10 | 0.47 | 0.005 |
| D1250 | S1250 | AfaCfaGfuGfuUfcUfcUfugcUfcUfaUfUfasAf | AS1250 | uUfauaAfgFfcCfaAfaGfaAfcAfCfUfgUfuUfsu | 0.07 | 0.14 | 0.55 | 0.005 |
| D1251 | S1251 | AfaCfaGfuGfuUfcUfcUfucUfcUfaUfUfasAf | AS1251 | uUfauaAfgFfcCfaAfaGfaAfcAfCfUfgUfuUfsu | 0.07 | 0.14 | 0.49 | 0.006 |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1252 | S1252 | cAGuGuucuuGcucuAuAAdTdT | AS1252 | UuAuAGAGcAAGAAcACUGdTdT | | | | 0.006 |
| D1253 | S1253 | AfacfaGfuGfuUfcUfugcUfcUfcUfaUfasAf | AS1253 | uUfaUfagaGfcAfaGfaAfcAfcUfgUfusUfsu | 0.05 | 0.12 | 0.43 | 0.006 |
| D1254 | S1254 | AfacfaGfuGfuUfcUfuGfcUfcUfcUfaUfasa | AS1254 | UfUfaUfagaGfcAfagaAfcAfcUfgUfusUfsu | 0.06 | 0.13 | 0.39 | 0.006 |
| D1255 | S1255 | AfacfaGfuGfuUfcUfuGfcUfGfcUfcUfaUfasa | AS1255 | UfUfaUfagaGfcAfaGfaAfcAfcUfgUfusUfsu | 0.08 | 0.17 | 0.48 | 0.007 |
| D1256 | S1256 | AfacfaGfuGfuUfcUfuGfcUfGfcUfcUfaUfasa | AS1256 | UfUfaUfagaGfcaaGfaAfcAfcUfgUfusUfsu | 0.08 | 0.14 | 0.40 | 0.007 |
| D1257 | S1257 | AfacfaGfuGfuUfcUfuGfcUfcUfcUfaUfasAf | AS1257 | uUfaUfagaGfcAfaAfcAfcUfgUfusUfsUf | 0.07 | 0.12 | 0.40 | 0.007 |
| D1258 | S1258 | AfacfaguGfuUfcUfuGfcUfcUfcUfaUfasAf | AS1258 | uUfaUfaGfaGfcAfagaAfcAfcUfgUfusUfsu | 0.08 | 0.13 | 0.41 | 0.007 |
| D1259 | S1259 | AfacfAfGfuGfuUfcUfuGfcUfcUfcUfaUfasAf | AS1259 | uUfaUfaGfaGfcAfaGfaAfcAfcUfgUfusUfsu | 0.05 | 0.11 | 0.35 | 0.008 |
| D1260 | S1260 | AfacaGfuGfuUfcUfuGfcUfcUfcUfaUfasAf | AS1260 | uUfaUfagaGfcAfaGfaAfcAfcUfgUfusUfsu | 0.06 | 0.12 | 0.40 | 0.008 |
| D1261 | S1261 | AfacfaGfuGfuUfcUfuGfcUfGfcUfaUfasAf | AS1261 | uUfaUfaGfAfGfcAfaGfaAfcAfcUfgUfUfusUfsu | 0.06 | 0.13 | 0.42 | 0.008 |
| D1262 | S1262 | AfacfaGfuGfuUfcUfuGfcucUfaUfasAf | AS1262 | uUfaUfaGfAfGfcAfaGfaAfcAfcUfgUfusUfsu | 0.06 | 0.13 | 0.37 | 0.008 |
| D1263 | S1263 | cAGuGuucuuGcucuAuAAdTdT | AS1263 | UuAuAGAGcAAGAAcACUGdTdT | | | | 0.008 |
| D1264 | S1264 | AfacfaGfuGfuUfcUfuGfcUfcUfcUfaUfasAf | AS1264 | uUfaUfaGfaGfagcAfaGfaAfcAfcUfgUfusUfsu | 0.07 | 0.12 | 0.50 | 0.008 |
| D1265 | S1265 | AfacfaGfuguUfcUfuGfcUfcUfcUfaUfasAf | AS1265 | uUfaUfaGfaGfcAfagaAfcAfcAfcUfgUfusUfsu | 0.12 | 0.13 | 0.48 | 0.009 |
| D1266 | S1266 | AfacfaGfaGfuUfcUfuGfcUfcUfcUfaUfasAf | AS1266 | uUfauaGfaGfcAfaGfaAfcAfcUfgUfusUfsu | 0.07 | 0.15 | 0.51 | 0.009 |
| D1267 | S1267 | AfacaAfuguUfcUfuGfdCfudCfudAudAsa | AS1267 | dTudAudAgaGfcAfaGfaAfcAfcAfgUfusUfsu | 0.06 | 0.14 | 0.48 | 0.0088 |
| D1268 | S1268 | AfacfaGfuGfuUfcUfuGfcucUfuGfcucUfaUfasAf | AS1268 | uUfaUfaGfAfGfcAfagaAfcAfcUfgUfusUfsu | 0.05 | 0.09 | 0.35 | 0.009 |
| D1269 | S1269 | cAGuGuucuuGcucuAuAAdTdT | AS1269 | UuAuAGAGcAAGAAcACUGdTdT | | | | 0.009 |
| D1270 | S1270 | aaCfaGfuGfuUfcUfuGfcUfcUfcUfaUfasAf | AS1270 | uUfaUfaGfaGfcAfagaAfcAfcUfgUfUfusUfsu | 0.07 | 0.14 | 0.49 | 0.009 |
| D1271 | S1271 | AfacfaGfuGfuUfcUfuGfcucUfaUfasAf | AS1271 | uUfaUfaGfaGfcAfagaAfcacUfgUfusUfsu | 0.06 | 0.10 | 0.36 | 0.009 |
| D1272 | S1272 | cAGuGuucuuGcucuAuAAdTdT | AS1272 | UuAuAGAGcAAGAAcACUGdTdT | | | | 0.009 |
| D1273 | S1273 | AfacfaGfuGfuUfcUfuGfcUfcUfaUfasAf | AS1273 | uUfaUfaGfaGfcAfagaAfcacUfgUfusUfsUf | 0.06 | 0.13 | 0.51 | 0.009 |
| D1274 | S1274 | AfacfaGfuGfuUfcUfuGfcUfuGfcuaUfasAf | AS1274 | uUfaUfAfGfaGfcAfagaAfcAfcUfgUfusUfsu | 0.06 | 0.12 | 0.46 | 0.010 |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1275 | S1275 | cAGuGuucuuGcucuAuAAdTdT | AS1275 | UuAuAGAGcAAGAACACUGdTdT | | | | 0.010 |
| D1276 | S1276 | AfacCfaGfuGfuUfcUfuGfcUfcUfauasAf | AS1276 | uUfAfUfaGfaGfcAfagaAfcAfcUfgUfusUfsu | 0.06 | 0.14 | 0.47 | 0.010 |
| D1277 | S1277 | AfacCfagfuGfuUfcUfuGfcUfcUfaUfasAf | AS1277 | uUfaUfagaGfcAfaGfaAfcAfcUfgUfusUfsu | 0.07 | 0.15 | 0.50 | 0.010 |
| D1278 | S1278 | AfacCfaGfuGfuUfcUfugcUfcUfaUfasAf | AS1278 | uUfaUfaGfcFfAfagaAfcAfcUfgUfusUfsu | 0.06 | 0.13 | 0.43 | 0.010 |
| D1279 | S1279 | cAGuGuucuuGcucuAuAAdTdT | AS1279 | UuAuAGAGcAAGAcACUGdTdT | | | | 0.010 |
| D1280 | S1280 | AfacCfaGfuGfuUfcUfuGfcUfcUfaUfasa | AS1280 | UfUfaUfaGfaGfcAfaGfaAfcAfcUfgUfususu | 0.06 | 0.14 | 0.45 | 0.010 |
| D1281 | S1281 | AfacCfAfgfuGfuUfcUfuGfcUfcUfaUfasa | AS1281 | UfUfaUfaGfcAfaGfaAfcAfcUfgUfusUfsu | 0.07 | 0.18 | 0.46 | 0.011 |
| D1282 | S1282 | AfacCfaGfuGfuUfcUfuGfcUfcUfaUfasAf | AS1282 | uUfaUfaGfaGfcAfaGfaAfcAfcUfgUfusUfsu | 0.07 | 0.15 | 0.55 | 0.011 |
| D1283 | S1283 | AfacCfaGfuGfuUfcUfuGfcucUfcUfaUfasAf | AS1283 | uUfaUfaGfaGfcAfaGfaAfcAfcUfgUfususu | 0.07 | 0.12 | 0.45 | 0.011 |
| D1284 | S1284 | AfacaGfuGfuuUfcUfuGfcUfcUfaUfasAf | AS1284 | uUfaUfaGfaGfcAfaGfaAfcAfcUfgUfusUfsu | 0.06 | 0.13 | 0.48 | 0.011 |
| D1285 | S1285 | AfacCfaGfuGfuUfcUfuGfcUfcUfaUfasAf | AS1285 | uUfaUfaGfaGfAfGfcAfaGfaAfcAfcUfguusUfsu | 0.06 | 0.11 | 0.40 | 0.011 |
| D1286 | S1286 | AfacCfaGfuGfuUfcUfuGfcUfcUfaUfauasAf | AS1286 | uUfaUfaGfaGfcAfaGfaAfcAfcUfcugUfusUfsu | 0.06 | 0.16 | 0.47 | 0.011 |
| D1287 | S1287 | AfacCfaGfuGfuUfcUfuGfugcUfcUfaUfasAf | AS1287 | uUfaUfaGfaGfcAfaGfaAfcAfcUfgUfususu | 0.07 | 0.19 | 0.46 | 0.012 |
| D1288 | S1288 | AfacCfaGfuGfuUfcUfuGfcUfcUfaUfasAf | AS1288 | uUfaUfaGfaGfcAfaGfcaaGfcAfaAfcAfcUfgUfusUfsu | 0.06 | 0.17 | 0.46 | 0.012 |
| D1289 | S1289 | AfacCfaGfuGfuUfcUfuGfcucUfcUfaUfasAf | AS1289 | uUfaUfaGfaGfcAfaGfaAfcAfcUfguusUfsu | 0.05 | 0.09 | 0.31 | 0.012 |
| D1290 | S1290 | AfacCfaGfuGfuUfcUfuGfcUfcUfcUfaUfasa | AS1290 | UfUfaUfaGfaGfcAfagaAfcAfcUfguusUfsu | 0.06 | 0.16 | 0.49 | 0.013 |
| D1291 | S1291 | AfacCfaGfuGfuUfcUfuGfcUfcUfaUfasa | AS1291 | uUfaUfaGfaGfcAfagaAfcAfcUfgUfusUfsUf | 0.06 | 0.11 | 0.32 | 0.013 |
| D1292 | S1292 | AfacCfaGfuGfuUfcUfugcUfcUfaUfasAf | AS1292 | uUfaUfaGfaGfcAfaGfcAfAfaGfaAfcAfcUfcugUfusUfsu | 0.06 | 0.14 | 0.44 | 0.013 |
| D1293 | S1293 | AfacCfaGfuGfUfUfcUfuGfcUfcUfaUfasAf | AS1293 | UfUfaUfaGfaGfcAfaGfaAfcAfcUfcugUfusUfsu | 0.07 | 0.16 | 0.39 | 0.013 |
| D1294 | S1294 | AfacCfaGfuGfuUfcUfuGfcUfcuaUfasAf | AS1294 | uUfaUfAfGfaGfcAfaGfaAfcAfcUfcugUfusUfsu | 0.07 | 0.18 | 0.41 | 0.014 |
| D1295 | S1295 | AfacCfaGfuGfuUfcUfuGfcUfcuaUfasAf | AS1295 | uUfaUfaGfaGfcAfaGfaAfcAfcacUfgUfusUfsu | 0.07 | 0.18 | 0.47 | 0.014 |
| D1296 | S1296 | adAdCagdTdGuudCdTugdCdTcudAdTasa | AS1296 | dTdTaudAdGagdCdAagdAdAcadCdTgudTsdTsu | 0.12 | 0.21 | 0.68 | 0.0146 |
| D1297 | S1297 | AfacaGfUfGfuUfcUfuGfcUfcUfaUfasAf | AS1297 | uUfaUfaGfaGfcAfaGfaAfcAfcacUfgUfUfusUfsu | 0.06 | 0.15 | 0.50 | 0.016 |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1298 | S1298 | AfacCfaGfUfGfuUfcUfuGfcUfcUfcUfauasAf | AS1298 | uUfAfUfaGfaGfcAfaGfaAfcacUfgUfusUfsu | 0.08 | 0.17 | 0.50 | 0.016 |
| D1299 | S1299 | AfaCfaguGfuUfcUfuGfcUfcUfaUfasAf | AS1299 | uUfaUfaGfaGfcAfaGfaAfcAfcUfUfgUfususu | 0.07 | 0.16 | 0.50 | 0.018 |
| D1300 | S1300 | AfacCfaGfuGfuUfcUfUfGfcUfcUfaUfauasAf | AS1300 | uUfaUfaGfaGfcAfaGfcaaGfaAfcAfcUfgUfusUfsu | 0.06 | 0.12 | 0.43 | 0.020 |
| D1301 | S1301 | AfacCfaGfuGfuUfcUfugcUfcUfaUfaUfasAf | AS1301 | uUfAfUfaGfaGfcUfAfaGfaAfcacUfgUfusUfsu | 0.07 | 0.17 | 0.45 | 0.021 |
| D1302 | S1302 | AfaCfaGfuguUfcUfUfGfcUfcUfaUfasAf | AS1302 | uUfaUfaGfaGfcaaGfaAfcAfcUfgUfusUfsu | 0.06 | 0.14 | 0.49 | 0.021 |
| D1303 | S1303 | AfAfCfaGftuguUfcUfUfGfcUfcUfaUfasAf | AS1303 | uUfaUfaGfaGfcAfaGfaAfcAfcUfgUguusUfsu | 0.07 | 0.24 | 0.51 | 0.022 |
| D1304 | S1304 | AfacCfaGftuucGfuuGfcUfuGfcUfaUfasAf | AS1304 | uUfaUfaGfaGfcAfaGfaAfcAfcUfgUfususu | 0.09 | 0.27 | 0.47 | 0.033 |
| D1305 | S1305 | aadCfAguddGfTucdTdTgcdTdCuadTdAsa | AS1305 | udTadTdAgaGdCaadGdAacdAdCugdTdTsusu | 0.19 | 0.36 | 0.86 | 0.045 |
| D1306 | S1306 | AfacaGfuguUfcUfuGfdCfdCUdCUdAudAsa | AS1306 | dTUdAUdAGfagfcAfaGfaAfcFfAfcUfGfUfusUfsu | 0.08 | 0.22 | 0.61 | |
| D1307 | S1307 | AfacaGfuguUfcUfdFfdTGfdCUdCUdAudAsa | AS1307 | dTUdAUdAGftaGfcACfUdCUdAfcUfGfUfusUfsu | 0.13 | 0.39 | 0.84 | |
| D1308 | S1308 | AfacaGfuguUfcUfuGfdCUdCUdAudAsa | AS1308 | dTUdAUdAGfaGfcAfaGfaAfcAfcUfgUfusUfsu | 0.09 | 0.13 | 0.48 | |
| D1309 | S1309 | AfacaAfuguUfcUfdFfdTGfdCUdCUdAudAsa | AS1309 | dTUdAUdAggaGfdCAfaGfdAfdCUdAfcAfgUfusUfsu | 0.07 | 0.13 | 0.58 | |
| D1310 | S1310 | AfacaAfuguUfcUfdFfdTGfdCUdCUdAudAsa | AS1310 | dTUdAudAgaGfdGfCAfaGfaAfcAfcAfgUfusUfsu | 0.07 | 0.14 | 0.55 | |
| D1311 | S1311 | AfAfCfaAfuGfuUfcUfuGfcUfcUfdAdTdAdsdA | AS1311 | dTdTdAdTaGfcAfaGfaAfcAfcAfgUfusUfsu | 0.10 | 0.30 | 0.66 | |
| D1312 | S1312 | AfacaAfuguUfcUfuGfdCUdCUdAudAsa | AS1312 | dTUdAUdAgaGfcAfaGfaAfcAfcUfgusUfsu | 0.09 | 0.13 | 0.48 | |
| D1313 | S1313 | AfAfCfaGfuGfuuUfcUfcUfuGfcUfcUfaUfaUfasAf | AS1313 | uUfaUfaGfagfcAfaGfaAfcAfcUfgusUfsu | 0.14 | 0.38 | 0.74 | |
| D1314 | S1314 | AfAfCfaGfuGfuuUfcUfcUfuGfcUfcUfaUfasAf | AS1314 | uUfaUfaGfagfcAfaGfaAfcAfcUfgusUfsu | 0.07 | 0.19 | 0.54 | |
| D1315 | S1315 | AfAfCfaGfuGfuUfcUfuGfcUfcUfaUfasAf | AS1315 | uUfaUfaGfagfcAfaGfaAfcAfcUfgUfusUfsu | 0.07 | 0.15 | 0.55 | |
| D1316 | S1316 | AfacCfaGfuGfuUfcUfuGfcUfcUfaUfaUfasAf | AS1316 | uUfaUfaGfagfcAfaGfaAfcAfcUfgUfusUfsu | 0.07 | 0.16 | 0.53 | |
| D1317 | S1317 | AfacCfaGfuGfuUfcUfuGfcUfcUfaUfasAf | AS1317 | uUfaUfaGfagfcAfaGfcAfaGfaAfcAfcUfgUfGfUfususu | 0.07 | 0.16 | 0.55 | |
| D1318 | S1318 | AfAfCfaGfuguUfcUfcUfcUfaUfasAf | AS1318 | uUfaUfaGfagfcAfaGfaAfcAfcUfguusUfsu | 0.10 | 0.32 | 0.61 | |
| D1319 | S1319 | AfAfCfaGftuGfuUfcUfuGfcUfcUfaUfasAf | AS1319 | uUfaUfaGfagfcAfaGfaAfcAfcUfUfususu | 0.08 | 0.16 | 0.53 | |
| D1320 | S1320 | AfacCfaGfuGfuUfcUfuGfcUfcUfaUfasAf | AS1320 | uUfaUfaGfagfcAfaGfaAfcAfcUfgUfususu | 0.08 | 0.16 | 0.61 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1321 | S1321 | AfAcCfaGfuGfuUfcUfcUfcUfaUfasAf | AS1321 | uUfaUfagaGfcAfaGfaAfcAfcUfgUfusUfsu | 0.06 | 0.14 | 0.58 | |
| D1322 | S1322 | AfaCfaGfuGfuUfcuuGfcUfcUfaUfasAf | AS1322 | uUfaUfaGfaGfcAfaGfaAfcAfcUfgUfusUfsu | 0.15 | 0.49 | 0.84 | |
| D1323 | S1323 | AfaCfaGfuGfuUfcUfuGfcUfcUfcuaUfasAf | AS1323 | uUfaUfAfgAfcAfaGfaAfcAfcUfgUfususu | 0.07 | 0.20 | 0.62 | |
| D1324 | S1324 | AfAfCfaGfuGfuUfcUfcUfcUfaUfasAf | AS1324 | uUfaUfaGfaGfcAfaGfaAfcAfcUfguusUfsu | 0.08 | 0.25 | 0.78 | |
| D1325 | S1325 | AfAfCfaGfuGfuUfcUfcUfcUfaUfasAf | AS1325 | uUfaUfaGfaGfcAfaGfaAfcAfcUfgUfusUfsu | 0.08 | 0.18 | 0.80 | |
| D1326 | S1326 | AfAfCfaGfuGfuUfcUfcUfcUfAfUfasAf | AS1326 | uUfaUfaGfaGfcAfaGfaAfcAfcUfguusUfsu | 0.07 | 0.21 | 0.66 | |
| D1327 | S1327 | AfaCfaGfuuCfuUfcUfcUfaUfcUfasAf | AS1327 | uUfaUfaGfaGfcAfaGfaAfcAfcUfgUfusUfsu | 0.10 | 0.31 | 0.70 | |
| D1328 | S1328 | AfaCfaGfuGfuUfcUfcUfcUfauasAf | AS1328 | uUfaUfaGfaGfcAfaGfaAfcAfcAfcUfguusUfsu | 0.07 | 0.15 | 0.55 | |
| D1329 | S1329 | AfaCfaAfGfuGfuUfcUfcUfcUfaUfasAf | AS1329 | uUfaUfaGfaGfcAfaGfaAfcAfcUfguusUfsu | 0.08 | 0.19 | 0.71 | |
| D1330 | S1330 | AfAfCfaGfuGfuUfcUfcUfcUfaUfasAf | AS1330 | uuaUfaGfaGfcAfaGfaAfcAfcUfgUfusUfsu | 0.09 | 0.27 | 0.76 | |
| D1331 | S1331 | AfaCfaGfuguUfcUfcUfcUfcUfaUfasAf | AS1331 | uUfaUfaGfaGfcAfaGfaAfcAfcUfgUfusUfsu | 0.07 | 0.21 | 0.65 | |
| D1332 | S1332 | AfaCfaGfuGfuUfcUfcUfcUfcuaUfasAf | AS1332 | uUfaUfaGfaGfcAfaGfcAfcAfcUfguusUfsu | 0.07 | 0.17 | 0.53 | |
| D1333 | S1333 | AfaCfaGfuGfuUfcUfcUfcUfaUfasAf | AS1333 | uUfaUfaGfaGfcAfaGfaAfcAfcacUfgUfusUfsu | 0.08 | 0.25 | 0.73 | |
| D1334 | S1334 | AfCfaguUfcUfcUfcUfcUfaUfasAf | AS1334 | uUfaUfaGfaGfcAfaGfaAfcAfcUfgUfusUfsu | 0.07 | 0.18 | 0.54 | |
| D1335 | S1335 | AfaCfaGfuUfcUfcuuUfcUfcUfaUfasAf | AS1335 | uUfaUfaGfaGfcAfaGfaAfcAfcUfgUfususu | 0.14 | 0.38 | 0.57 | |
| D1336 | S1336 | AfaCfaGfuGfuUfcUfcUfcUfaUfasAf | AS1336 | uUfaUfaGfaGfcAfaGfaAfaacAfcUfgUfusUfsu | 0.16 | 0.50 | 0.96 | |
| D1337 | S1337 | AfaCfaGfuGfuUfcUfcUfcUfaUfauasAf | AS1337 | uUfaUfaGfaGfcAfaGfaAfcAfcUfgUfusUfsu | 0.08 | 0.19 | 0.54 | |
| D1338 | S1338 | AfAfCfaGfuGfuUfcUfcUfugcUfcUfaUfasAf | AS1338 | uUfaUfaGfaGfcAfaGfCfAfaGfaAfcAfcUfguusUfsu | 0.08 | 0.20 | 0.69 | |
| D1339 | S1339 | AfaCfaGfuGfuUfcUfcUfcuaUfasAf | AS1339 | uUfaUfaGfaGfcAfagaAfcAfcUfgUfusUfsu | 0.07 | 0.16 | 0.55 | |
| D1340 | S1340 | AfaCfaGfuGfuUfcUfcUfcUfaUfasAf | AS1340 | uUfaUfAfgAfcAfaGfaAfcAfcUfgUfusUfsu | 0.08 | 0.17 | 0.57 | |
| D1341 | S1341 | AfaCfaGfuguUfcUfcUfcUfaUfasAf | AS1341 | uUfaUfaGfaGfcAfaGfaAfcAfcUfgUfususu | 0.08 | 0.22 | 0.63 | |
| D1342 | S1342 | AfAfCfaGfuGfuUfcuuGfcUfcUfaUfasAf | AS1342 | uUfaUfaGfaGfcAfAfGfaAfcAfcUfguusUfsu | 0.21 | 0.56 | 0.86 | |
| D1343 | S1343 | AfacaGfuUfuUfcUfcUfcUfaUfasAf | AS1343 | uUfaUfaGfaGfcAfaacAfcAfcUfgUfusUfsu | 0.14 | 0.37 | 0.73 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1344 | S1344 | AfacCfaGfuGfuuCfUfGfcUfcUfaUfasAf | AS1344 | uUfaUfaGfaGfcaaGfAfAfcAfcUfgUfusUfsu | 0.08 | 0.20 | 0.66 | |
| D1345 | S1345 | AfacCfAfGfuGfuuGfcuuGfcUfcUfaUfasAf | AS1345 | uUfaUfaGfaGfcAfAfGfaAfcAfcugUfusUfsu | 0.12 | 0.34 | 0.73 | |
| D1346 | S1346 | AfacCfaGfuGfuUfcUfuGfcUfcUfaUfasAf | AS1346 | uUfaUfaGfaGfcAfaGfaAfcAfcUfgUfusUfsu | 0.16 | 0.42 | 0.90 | |
| D1347 | S1347 | AfacCfaGfuGfUfUfcUfuGfcUfcUfaUfasAf | AS1347 | uUfaUfaGfaGfcAfaGfaAfcAfcUfgUfgUfsUf | 0.17 | 0.43 | 0.85 | |
| D1348 | S1348 | AfacCfAfGfuGfuuGfcUfuGfcUfcUfaUfasAf | AS1348 | uUfaUfaGfaGfcAfaGfaAfcAfcugUfusUfsu | 0.08 | 0.21 | 0.58 | |
| D1349 | S1349 | AfacCfaGfUfGfUfcUfuGfcUfcuaUfasAf | AS1349 | uUfaUfAfGfaGfcAfaGfaAfcAfcUfgUfusUfsu | 0.21 | 0.39 | 0.88 | |
| D1350 | S1350 | AfacCfaguGfuUfcUfuGfcUfcUfaUfasAf | AS1350 | uUfaUfaGfaGfcaaGfaAfcAfcUfgUfusUfsu | 0.06 | 0.13 | 0.52 | |
| D1351 | S1351 | AfacCfAfgfuguGfuUfcuuGfcUfcUfaUfasAf | AS1351 | uUfaUfaGfaGfcAfaGfaACfAfcugUfusUfsu | 0.08 | 0.21 | 0.58 | |
| D1352 | S1352 | AfacCfaGfUfGfUfcUfuGfcUfcUfaUfasAf | AS1352 | uUfaUfaGfAfGfaGfaAfGfaAfcacUfgUfusUfsu | 0.18 | 0.49 | 0.84 | |
| D1353 | S1353 | AfacCfaGfuGfUfUfcUfcuGfcUfcUfaUfasAf | AS1353 | uUfaUfaGfaGfcAfaGfaacAfcUfgUfgUfsUf | 0.11 | 0.25 | 0.68 | |
| D1354 | S1354 | AfacCfAfGfUfGfUfcUfuGfcUfcUfaUfasAf | AS1354 | uUfaUfaGfaGfcaaGfaAfcAfcUfgUfusUfsu | 0.07 | 0.15 | 0.52 | |
| D1355 | S1355 | AfacCfaGfGfuuCfUfuGfcUfcUfaUfasAf | AS1355 | uUfaUfaGfaGfcAfaGfAfAfaUfcaUfgUfusUfsu | 0.10 | 0.26 | 0.63 | |
| D1356 | S1356 | AfacCfaGfuGfUfcUfugcUfcUfaUfasAf | AS1356 | uUfaUfaGfaGfCfAfaGfaacAfcUfgUfusUfsu | 0.16 | 0.33 | 0.79 | |
| D1357 | S1357 | AfacCfaGfuGfUfGfcUfUfUfGfcUfcUfaUfasAf | AS1357 | uUfaUfaGfaGfcAfaGfaAfcAfcugUfusUfsUf | 0.09 | 0.19 | 0.51 | |
| D1358 | S1358 | AfacCfaGfuGfUfcUfuGfcUfcUfaUfasAf | AS1358 | uUfaUfaGfaGfcAfaGfaAfcAfcUfgUfusUfsu | 0.22 | 0.48 | 0.71 | |
| D1359 | S1359 | AfacCfaGfUfGfUfUfcUfuGfcUfcUfaUfasAf | AS1359 | uUfaUfaGfaGfcAfaGfaAfcAfcUfgUfusUfsUf | 0.10 | 0.17 | 0.61 | |
| D1360 | S1360 | AfacCfaGfuGfUfGfcUfUfuGfcUfcUfaUfasAf | AS1360 | uUfaUfaGfaGfcAfaGfaacAfcAfcUfgUfusUfsu | 0.14 | 0.40 | 0.87 | |
| D1361 | S1361 | AfacCfaGfuGfUfUfcUfuGfcUfcuaUfasAf | AS1361 | uUfaUfaGfAfGfcaaGfaAfcAfcUfgUfusUfsu | 0.07 | 0.14 | 0.52 | |
| D1362 | S1362 | aaCfaGfuGfuuCfuGfcUfcUfaUfasAf | AS1362 | uUfaUfaGfagcAfaGfCfAfcAfcUfgUfusUfsu | 0.10 | 0.28 | 0.81 | |
| D1363 | S1363 | AfacCfaGfuuCfuGfugcUfcUfaUfasAf | AS1363 | uUfaUfaGfaGfcAfaGfCfAfcAfcUfgUfusUfsu | 0.06 | 0.16 | 0.68 | |
| D1364 | S1364 | AfacCfaGfuGfUfuGfugcUfcUfaUfRfsAf | AS1364 | uUfauaGfaGfcAfaGfCfAfaAfcAfcUfgUfusUfsu | 0.09 | 0.26 | 0.67 | |
| D1365 | S1365 | aacaguguucuugcucuauasa | AS1365 | uuaUfaGfaGfagcAfaGfaAfcAfcUfgUfusUfsu | 0.20 | 0.59 | 0.95 | |
| D1366 | S1366 | AfacCfaGfuGfUfUfcUfuGfCfUfcUfauasAf | AS1366 | uUfAfUfaGfagcAfagCfAfaAfcAfcUfgUfusUfsu | 0.06 | 0.13 | 0.53 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1367 | S1367 | AfacCfaGfuGfuUfcGfcUfcUfaUfasAf | AS1367 | uUfaUfAfGfagcAfaGfaAfcAfcUfgUfusUfsUf | 0.08 | 0.16 | 0.53 | |
| D1368 | S1368 | AfaCfaGftuguUfcGfcUfcUfaUfAfasAf | AS1368 | uUfauaGfaGfcAfaGfaAfcAfcUfgUfusUfsu | 0.07 | 0.15 | 0.54 | |
| D1369 | S1369 | AfacCfaGftuGfuUfcuuGfcUfcUfaUfAfasAf | AS1369 | uuaUfaGfaGfcAfaGfaAfcAfcUfgUfusUfsu | 0.23 | 0.56 | 0.89 | |
| D1370 | S1370 | AfacCfaGftuGfuUfcGfcUfcUfcuaUfasAf | AS1370 | uUfaUfAfGfagcaAfaGfaAfcAfcUfgUfusUfsu | 0.06 | 0.12 | 0.55 | |
| D1371 | S1371 | AfacCfaGftuGfuUfcGfcUfcUfcuaUfasAf | AS1371 | uUfaUfAfGfagcAfaGfaAfcAfcUfgUfusUfsu | 0.07 | 0.18 | 0.58 | |
| D1372 | S1372 | AfaCfagGfuUfcUfuGfcUfcUfAfUfasAf | AS1372 | uUfauaGfaGfcAfaGfaAfcAfcUfgUfusUfsu | 0.06 | 0.15 | 0.56 | |
| D1373 | S1373 | AfacCfaGftuucGfuuGfcUfcUfaUfasAf | AS1373 | uuaUfaGfaGfcAfaGfaAfcAfcUfgUfusUfsu | 0.21 | 0.51 | 0.89 | |
| D1374 | S1374 | AfacCfaGftuguUfcGfcUfcUfaUfasAf | AS1374 | uUfaUfaGfaGfcAfaGfcAfaGfaAfcAfcUfgUfusUfsu | 0.08 | 0.21 | 0.64 | |
| D1375 | S1375 | AfacCfaGftuguUfcGfcUfcUfaUfaUfasAf | AS1375 | uUfaUfaGfagcAfaGfaAfcAfcUfgUfusUfsu | 0.15 | 0.40 | 0.94 | |
| D1376 | S1376 | AfacCfaGftuGfuUfcuuGfcUfaUfasAf | AS1376 | uUfaUfaGfagcAfaGfaAfcAfcUfgUfusUfsu | 0.13 | 0.40 | 0.96 | |
| D1377 | S1377 | AfacCfaGftuGfuUfcGfcUfcUfauasAf | AS1377 | uUfAUfagaGfcAfaGfaAfcAfcUfgUfusUfsu | 0.08 | 0.17 | 0.64 | |
| D1378 | S1378 | AfacCfaGfuguUfcGfcUfcUfaUfaUfasAf | AS1378 | uuaUfaGfaGfcAfaGfaAfcAfcUfgUfusUfsu | 0.18 | 0.50 | 0.97 | |
| D1379 | S1379 | AfacCfaGftuucGfcUfcUfaUfAfasAf | AS1379 | uUfaUfaGfagcAfaGfaAfcAfcUfgUfusUfsu | 0.08 | 0.24 | 0.79 | |
| D1380 | S1380 | aaCfaGftuGfuUfcGfcUfcUfaUfAfasAf | AS1380 | uUfauaGfaGfcAfaGfaAfcAfcUfgUfusUfsu | 0.07 | 0.14 | 0.58 | |
| D1381 | S1381 | AfacCfaGfuGfuUfcGfcUfcUfaUfAfasAf | AS1381 | uuaUfaGfaGfcAfaGfaAfcAfcUfgUfUfusUfsu | 0.11 | 0.34 | 0.96 | |
| D1382 | S1382 | AfacCfaGfuguUfcfcuuGfcUfaUfasAf | AS1382 | uUfaUfaGfagcAfaGfaAfcAfcUfgUfusUfsu | 0.08 | 0.18 | 0.69 | |
| D1383 | S1383 | AfacCfaGftuGfuUfcuuGfcUfaUfasAf | AS1383 | uUfaUfagaGfcAfaGfaAfcAfcUfgUfusUfsu | 0.14 | 0.38 | 0.85 | |
| D1384 | S1384 | AfacCfaGftuGfuUfcGfcUfcUfaUfaUfasAf | AS1384 | uUfauaGfaGfcAfaGfaAfcAfcUfgUfusUfsUf | 0.07 | 0.16 | 0.54 | |
| D1385 | S1385 | AfacCfaGftuGfuUfcGfcUfcUfaUfAfasAf | AS1385 | uuaUfaGfaGfcAfaGfaAfcAfcUfgUfusUfsu | 0.25 | 0.56 | 0.90 | |
| D1386 | S1386 | aacaguguucUfaGfcUfcUaudAsa | AS1386 | uUfdAUdAGfaGfcAfaGfaadCadCudGdTsusu | 0.08 | 0.19 | 0.70 | |
| D1387 | S1387 | AfacCfaGfuguUfcfcfcfaUfasAf | AS1387 | uUfaUfaGfagcAfaGfaAfcAfcUfgUfusUfsu | 0.08 | 0.14 | 0.60 | |
| D1388 | S1388 | AfacCfaGftuucGfuGfcUfcUfaUfasAf | AS1388 | uUfagaGfcAfaGfaAfcAfcUfgUfusUfsu | 0.08 | 0.14 | 0.60 | |
| D1389 | S1389 | AfacCfaGftuGfuUfcGfcUfcUfcuaUfasAf | AS1389 | uuaUfaGfcAfaGfaAfcAfcUfgUfusUfsu | 0.08 | 0.19 | 0.62 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1390 | S1390 | aaCfaGfuGfuUfcUfuGfcUfcUfaUfAfsAf | AS1390 | uuaUfaGfaGfcAfaGfaAfcAfcUfgUfUfsUfsu | 0.08 | 0.27 | 0.76 | |
| D1391 | S1391 | aacaguucdTudGcdTcdTadTasa | AS1391 | uUfdAUdAGfaGfAfaGfaAfaadCadCudGudTsusu | 0.18 | 0.36 | 0.81 | |
| D1392 | S1392 | AfacaGfuGfuUfcUfuGfcUfcUfaUfasAf | AS1392 | uUfaUfaGfagcAfaGfaAfcAfcUfgUfusUfsu | 0.07 | 0.17 | 0.55 | |
| D1393 | S1393 | AfacCfaGfuguUfcUfuGfcUfcUfaUfasAf | AS1393 | uUfaUfagaGfcAfaAfcAfcUfgUfusUfsu | 0.07 | 0.15 | 0.57 | |
| D1394 | S1394 | AfacCfaGfuGfuUfcuuGfcUfcUfaUfasAf | AS1394 | uUfauaGfaGfcAfAfGfaAfcAfcUfgUfusUfsu | 0.26 | 0.68 | 1.06 | |
| D1395 | S1395 | AfacCfaGfuGfuUfcUfuGfcucUfaUfAfsAf | AS1395 | uuaUfaGfAfgfcAfaGfaAfcAfcUfgUfusUfsu | 0.06 | 0.18 | 0.58 | |
| D1396 | S1396 | AfacCfaGfuGfuUfcUfuGfcUfcUfaUfAfsAf | AS1396 | uuaUfaGfaGfcAfaGfaAfcAfcUfgUfusUfsUf | 0.09 | 0.27 | 0.73 | |
| D1397 | S1397 | AfacCfaAfuGfuUfcUfuGfcdAdCdTdAUfasAf | AS1397 | uUfadTdAdGdGAGfcAfAfGfcAfAfGfcAfcAfgUfusUfsu | 0.20 | 0.51 | 0.73 | |
| D1398 | S1398 | AfacaGfuguUfcuuGfcucUfauasAf | AS1398 | uUfAfUfaGfAfGfcAfAfGfcAfAfcUfGfUfusUfsu | 0.13 | 0.34 | 0.86 | |
| D1399 | S1399 | dAacadGuguduTcuudGcucdTauasdA | AS1399 | udTdAdTadGdAdGdAdGcdAdAdGadAdCdAcdTdGdTusdTsu | 0.24 | 0.42 | 0.82 | |
| D1400 | S1400 | AfacCfaAfuGfuUfcUfuGfdCdAdCdTaUfasAf | AS1400 | uUfaUfadGdAdGdAdGcAfaGfcAfcAfgUfUfsUfsu | 0.49 | 0.85 | 0.78 | |
| D1401 | S1401 | AfacCfaAfuUfcUfuGfdCdAdCdTaUfasAf | AS1401 | uUfaUfadGdAdGdGcdCAdCdAdCUfaUfasUfsu | 0.67 | 0.83 | 0.85 | |
| D1402 | S1402 | aaCfAfguUfucUfUfgCfUfCfuaUfAfsa | AS1402 | uUfaUfafgaGfCfaaGfAfacAfCfugUfususu | 0.18 | 0.47 | 0.80 | |
| D1403 | S1403 | AfacCfaAfuGfuUfcUfuGfcdAdCdTadTdAsAf | AS1403 | udTdAUfadGdAGfcAfaGfaGfcAfcAfgUfusUfsu | 0.73 | 0.89 | 0.77 | |

TABLE 2-continued

ANGPTL3 modified duplex

| Duplex ID | S ID | Sense strand (S) (SEQ ID NOS 5-424, respectively, in order of appearance) | AS ID | Antisense strand (AS) (SEQ ID NOS 425-844, respectively, in order of appearance) | % of mRNA remained conc. of siRNA | | | IC50 (nM) |
|---|---|---|---|---|---|---|---|---|
| | | | | | 1 nM | 0.1 nM | 0.01 nM | |
| D1404 | S1404 | aacAgugUucuUgcuCuauAsa | AS1404 | uUaUAgAGcAgAGaCACuGUUsusu | 0.12 | 0.39 | 0.79 | |
| D1405 | S1405 | AacaGuguUcuuGcucUauasA | AS1405 | uUAUaGAGcAAGaACAcUGUusUsu | 0.12 | 0.37 | 0.77 | |
| D1406 | S1406 | AfaCfaAfuGfuUfcUfudGdCAfcUfadTdAsAf | AS1406 | udTdAUfaGfadGdCAfaGfcAfcAfgUfusUfsu | 0.59 | 0.93 | 0.89 | |
| D1407 | S1407 | aACagUGuuCUugCUcuAUasa | AS1407 | UUauAgagCAagCAacaCUguUsUsu | 0.09 | 0.16 | 0.55 | |
| D1408 | S1408 | AfaCfaAfuGfuUfcUfuGfcAfcdTdAdTdAsAf | AS1408 | udTdAdTdAgFaGfcAfaGfaAfcAfcAfgUfusUfsu | 0.22 | 0.64 | 0.86 | |
| D1409 | S1409 | aaCagUucUGugcUCuaUAsa | AS1409 | uUaUAgaGCaaGaAcaCUgUUsusu | 0.13 | 0.31 | 0.76 | |
| D1410 | S1410 | AfaCfaAfuGfuUfcUfuGfcAfdCdTdAdTdAsAf | AS1410 | udTdAdTdAdGaGfcAfaGfaGfcAfcAfgUfusUfsu | 0.77 | 0.94 | 0.93 | |
| D1411 | S1411 | aacAfgUfucuUfgcuCfuauAfsa | AS1411 | uUfaUfAfgAfgCfcfaAfGfcfaAfcAfcfuGfUfUfsusu | 0.23 | 0.53 | 1.04 | |
| D1412 | S1412 | aacdAgugdTucudTgcudCuaudAsa | AS1412 | udTadTdAgdAdgdAdGdCadAdGdAadCdAdCudGdTdTsusu | 0.30 | 0.64 | 0.90 | |
| D1413 | S1413 | AfaCfaGfuGfuUfcUfuGfcUfuGfcUfaUfasa | AS1413 | UfUfaUfaGfaGfaGfcAfaGfaaCafcUfgUfusUfsu | 0.09 | 0.19 | 0.63 | |
| D1414 | S1414 | AfaCfaGfuGfuUfcUfuGfcUfuGfcUfaUfasa | AS1414 | UfUfaUfaGfaGfcAfaGfaacAfcUfgUfusUfsu | 0.11 | 0.28 | 0.66 | |
| D1415 | S1415 | AfaCfaGfuGfuUfcUfuGfcUfuGfcUfaUfasa | AS1415 | UfUfaUfagcAfaGfaAfaGfcAfcAfcUfgUfusUfsu | 0.06 | 0.13 | 0.53 | |
| D1416 | S1416 | aacaguguucuugcucuauasa | AS1416 | UfUfaAfUfaGfCfaAfaGfcAfaGfaAfcAfcUfgUfCfUfgUfUfUfsusu | 0.20 | 0.53 | 0.99 | |
| D1417 | S1417 | AfaCfaGfuGfuUfcUfuGfcUfcUfcUfaUfasa | AS1417 | UfUfauaGfaGfcAfaGfaAfcAfcUfgUfusUfsu | 0.07 | 0.17 | 0.53 | |
| D1418 | S1418 | aAfCfagUfGfuuCfUfugcUfuUfcuAfUfasa | AS1418 | UfUfauAfgAfgCfAfagaAfacCfUfguUfsUsu | 0.08 | 0.20 | 0.70 | |
| D1419 | S1419 | AfaCfaAfgGfuFfcUfuGfcUfcUfaUfasAf | AS1419 | uUfaUfaGfaGfcAfaGfaAfcAfcugUfusUfsUf | 0.08 | 0.20 | 0.70 | |

Example 3: In Vitro Silencing Activity with Various Chemical Modifications on TTR siRNA The IC$_{50}$ for each modified siRNA is determined in Hep3B cells by standard reverse transfection using Lipofectamine RNAiMAX. In brief, reverse transfection is carried out by adding 5 μL of Opti-MEM to 5 μL of siRNA duplex per well into a 96-well plate along with 10 μL of Opti-MEM plus 0.5 μL of Lipofectamine RNAiMax per well (Invitrogen, Carlsbad CA. cat #13778-150) and incubating at room temperature for 15-20 minutes. Following incubation, 100 μL of complete growth media without antibiotic containing 12,000-15,000 Hep3B cells is then added to each well. Cells are incubated for 24 hours at 37° C. in an atmosphere of 5% CO2 prior to lysis and analysis of ApoB and GAPDH mRNA by bDNA (Quantigene). Seven different siRNA concentrations ranging from 10 nM to 0.6 pM are assessed for IC$_{50}$ determination and ApoB/GAPDH for ApoB transfected cells is normalized to cells transfected with 10 nM Luc siRNA.

| Abbreviation | Nucleotide(s) |
|---|---|
| Af | 2'-F-adenosine |
| Cf | 2'-F-cytidine |
| Gf | 2'-F-guanosine |
| Uf | 2'-F-uridine |
| A | adenosine |
| C | cytidine |
| G | guanosine |
| U | uridine |
| a | 2'-O-methyladenosine |
| c | 2'-O-methylcytidine |
| g | 2'-O-methylguanosine |
| u | 2'-O-methyluridine |
| dT | 2'-deoxythymidine |
| s | phosphorothioate linkage |

TABLE 3

ANGPTL3 modified duplex

| Duplex ID | Sense ID | SS seq (SEQ ID NOS 845-1025, respectively, in order of appearance) | AS ID | AS seq (SEQ ID NOS 1026-1206, respectively, in order of appearance) | RNAimax, Hep3b 10 nM | 0.1 nM | 0.025 nM |
|---|---|---|---|---|---|---|---|
| D2000 | S2000 | UfcAfcAfaUfuAfAfGfcUfcCfuUfcUfuUf | A2000 | aAfaGfaAfgGfaGfcuuAfaUfuGfuGfasAfsc | 0.036 | 0.274 | 0.233 |
| D2001 | S2001 | UfuAfuUfgUfuCfCfUfcUfaGfuUfaUfuUf | A2001 | aAfaUfaAfcUfaGfaggAfaCfaAfuAfasAfsa | 0.044 | 0.278 | 0.247 |
| D2002 | S2002 | GfcUfaUfgUfuAfGfAfcGfaUfgUfaAfaAf | A2002 | uUfuUfaCfaUfcGfucuAfaCfaUfaGfcsAfsa | 0.062 | 0.474 | 0.449 |
| D2003 | S2003 | GfgAfcAfuGfgUfCfUfuAfaAfgAfcUfCfsa | A2003 | aAfaGfuCfuUfuAfagaCfcAfuGfuCfcsCfsa | 0.303 | 1.042 | 0.912 |
| D2004 | S2004 | CfaAfaAfaCfuCfAfAfcAfuAfuUfuGfaUf | A2004 | aUfcAfaAfuAfuGfuugAfgUfuUfuUfgsAfsa | 0.102 | 0.623 | 0.499 |
| D2005 | S2005 | AfcCfaGfuGfaAfAfUfcAfaAfgAfaGfaAf | A2005 | uUfcUfuCfuUfuGfauuUfcAfcUfgGfusUfsu | 0.124 | 0.901 | 0.756 |
| D2006 | S2006 | CfaCfaAfuUfaAfGfCfuCfcUfuCfuUfuUf | A2006 | aAfaAfgAfaGfgAfgcuUfaAfuUfgUfgsAfsa | 0.069 | 0.269 | 0.244 |
| D2007 | S2007 | CfuAfuGfuUfaGfAfCfgAfuGfuAfaAfaAf | A2007 | uUfuUfuAfcAfuCfgucUfaAfcAfuAfgsCfsa | 0.052 | 0.622 | 0.589 |
| D2008 | S2008 | UfcAfaCfaUfaUfUfUfgAfuCfaGfuCfuUf | A2008 | aAfgAfcUfgAfuCfaaaUfaUfgUfuGfasGfsu | 0.133 | 0.798 | 0.785 |
| D2009 | S2009 | AfaCfuGfaGfaAfGfAfaCfuAfcAfuAfuAf | A2009 | uAfuAfuGfuAfgUfucuUfcUfcAfgUfusCfsc | 0.097 | 0.671 | 0.528 |
| D2010 | S2010 | AfcAfaUfaAfaGfCfUfcCfuUfcUfuUfuUf | A2010 | aAfaAfaGfaAfgAfgcUfuAfaUfuGfusGfsa | 0.145 | 0.308 | 0.293 |
| D2011 | S2011 | CfuCfcAfgAfgCfCfAfaAfaUfcAfaGfaUf | A2011 | aUfcUfuGfaUfuUfuggCfuCfuGfgAfgsAfsu | 0.122 | 0.882 | 0.938 |
| D2012 | S2012 | CfgAfuGfuAfaAfAfAfuUfuUfaGfcCfaAf | A2012 | uUfgGfcUfaAfaAfuuuUfuAfcAfuCfgsUfsc | 0.102 | 0.843 | 0.733 |
| D2013 | S2013 | GfuCfuUfaAfaGfAfCfuUfuGfuCfcAfuAf | A2013 | uAfuGfaAfcAfaAfgucUfuUfaAfgAfcsCfsa | 1.133 | 1.105 | 1.022 |
| D2014 | S2014 | CfaAfcAfuAfuUfUfgAfuCfaGfuCfuUf | A2014 | aAfaGfaCfuGfaUfcaaAfuAfuGfuUfgsAfsg | 0.077 | 0.413 | 0.450 |
| D2015 | S2015 | AfcUfgAfgAfaGfAfAfcUfaCfaUfaUfuUf | A2015 | uUfaUfaUfgUfaGfuucUfuCfuCfaGfusUfsc | 0.055 | 0.293 | 0.364 |
| D2016 | S2016 | CfcAfgAfgCfcAfAfAfaUfcAfaGfaUfuUf | A2016 | aAfaUfcUfuGfaUfuuuGfgCfuCfuGfgsAfsg | 0.080 | 0.650 | 0.499 |
| D2017 | S2017 | GfaUfgUfaAfaAfAfuUfuUfaAfgCfcAfaUf | A2017 | aUfuGfgCfuAfaAfauuUfuUfaCfaUfcsGfsu | 0.076 | 0.605 | 0.579 |
| D2018 | S2018 | UfcUfuAfaAfgAfCfUfuUfgUfcCfaUfaAf | A2018 | uUfaUfgGfaCfaAfaguCfuUfuAfaGfasCfsc | 1.326 | 1.098 | 0.927 |
| D2019 | S2019 | AfaCfaUfaUfuUfGfAfuCfaGfuCfuUfuUf | A2019 | aAfaAfgAfcUfgAfucaAfaUfaUfgUfusGfsa | 0.047 | 0.560 | 0.477 |
| D2020 | S2020 | CfuGfaGfaAfgAfAfCfuAfcAfuAfuAfaAf | A2020 | uUfuAfuAfuGfuAfguuCfuUfcUfcAfgsUfsu | 0.066 | 0.690 | 0.681 |
| D2021 | S2021 | AfaUfuAfaGfcUfcCfuUfcUfuUfuUfaUf | A2021 | aUfaAfaAfaGfaAfggaGfcUfuAfaUfusGfsu | 0.041 | 0.611 | 0.251 |
| D2022 | S2022 | AfaAfuCfaAfgAfUfUfuGfcUfaUfgUfuAf | A2022 | uAfaCfaUfaGfcAfaauCfuUfgAfuUfusUfsg | 0.053 | 0.555 | 0.516 |
| D2023 | S2023 | UfuCfaGfuUfgGfGfAfcAfuGfuGfcUfuAf | A2023 | uAfaGfaCfcAfuGfuccCfaAfcUfgAfasGfsg | 0.779 | 1.045 | 0.963 |
| D2024 | S2024 | GfgGfcCfaAfaUfUfAfaUfgAfcAfuAfaAf | A2024 | aAfuAfuGfuCfaUfuaaUffuUfgGfcCfcsUfsu | 1.487 | 0.949 | 0.883 |
| D2025 | S2025 | AfcAfuAfuUfuGfAfUfcAfgUfcUfuUfuUf | A2025 | aAfaAfgAfcUfgAfucaAfaUfaUfgUfusGfsg | 0.043 | 0.432 | 0.477 |
| D2026 | S2026 | AfgAfaCfuAfcAfUfAfuAfaAfcUfaCfaAf | A2026 | uUfgUfaGfuUfuAfuauGfuAfgUfuCfusUfsc | 0.324 | 1.042 | 0.905 |
| D2027 | S2027 | AfuUfaAfgCfuCfCfUfuCfuUfuUfuAfuUf | A2027 | aAfuAfaAfaAfgAfaggAfgCfuUfaAfusUfsg | 0.042 | 0.283 | 0.224 |
| D2028 | S2028 | AfgAfuUfuGfcUfAfUfgUfuAfgAfcGfaUf | A2028 | aUfcGfuCfuAfaCfauaGfcAfaAfuCfusGfsg | 0.349 | 0.936 | 0.896 |
| D2029 | S2029 | UfcAfgUfuGfgGfAfCfaUfgGfuCfuAfaAf | A2029 | uUfaAfgAfcCfaUfgucCfcAfaCfuGfasAfsg | 0.914 | 0.907 | 0.944 |
| D2030 | S2030 | GfgCfcAfaAfuUfAfAfuGfaCfaUfaUfuUf | A2030 | aAfaUfaUfgUfcAfuuaAfuUfuGfgCfcsCfsa | 0.047 | 0.353 | 0.326 |
| D2031 | S2031 | CfaUfaUfuUfgAfUfCfaGfuCfuUfuUfaAf | A2031 | uAfaAfaAfgAfcUfgauCfaAfaUfaUfgsUfsu | 0.110 | 0.867 | 0.842 |
| D2032 | S2032 | UfaCfaUfaUfaAfAfCffuAfcAfaUfaGfsu | A2032 | uUfgAfuUfgGfuAfguuUfaUfaUfgUfasGfsu | 0.200 | 0.699 | 0.656 |
| D2033 | S2033 | UfuUfuAfaUfgUfUfCfcUfcUfaGfuUfaUf | A2033 | aUfaAfcUfaGfaGfgaaCfaAfuAfaAfasAfsg | 0.050 | 0.218 | 0.192 |
| D2034 | S2034 | UfuGfcUfaUfgUfUfAfgAfcGfaUfgUfaAf | A2034 | uUfaCfaUfcGfuCfuaaCfaUfaGfcAfasUfsu | 0.096 | 0.792 | 0.640 |
| D2035 | S2035 | CfaGfuUfgGfgAfCfAfuGfuGfcUfuAfaAf | A2035 | uUfuAfaGfaCfcAfuguCfcCfaAfcUfgsAfsa | 0.127 | 0.936 | 0.890 |
| D2036 | S2036 | AfaAfuUfaAfuGfAfCfaUfaUfuUfuAfaAf | A2036 | uUfuAfaAfaUfaUfgucAfuUfaAfuUfusGfsg | 0.061 | 0.683 | 0.668 |
| D2037 | S2037 | GfaUfcAfgUfcUfUfuUfaUfgAfuCfuAf | A2037 | uAfgAfuCfaUfaAfaaaGfaCfuGfaUfcsAfsa | 0.157 | 1.010 | 0.723 |
| D2038 | S2038 | AfcAfuAfuAfaAfCfUfaCfaAfgUfcAfaAf | A2038 | uUfuGfaCfuUfgUfaguUfuAfuAfuGfusAfsg | 0.047 | 0.532 | 0.525 |
| D2039 | S2039 | UfuUfaUfuGfuUfCfCfuCfuAfgUfuAfuUf | A2039 | aAfuAfaCfuAfgAfggaAfcAfaUfaAfasAfsa | 0.031 | 0.505 | 0.238 |
| D2040 | S2040 | UfgCfuAfuGfuUfAfGfaCfgAfuGfuAfaAf | A2040 | uUfuAfcAfuCfgUfcuaAfcAfuAfgCfasAfsa | 0.056 | 0.484 | 0.408 |
| D2041 | S2041 | GfgGfaCfaUfgGfUfCfuUfaAfaGfaCfuUf | A2041 | aAfgUfcUfuUfaAfgacCfaUfgUfcCfcsAfsa | 0.570 | 0.999 | 0.994 |
| D2042 | S2042 | UfgAfcAfuAfuUfUfCfaAfaAfcAfcUfaAf | A2042 | uUfgAfgUfuUfuUfgaaAfuAfuGfuCfasUfsu | 0.065 | 0.870 | 0.728 |
| D2043 | S2043 | AfuCfaGfuCfuUfUfUfuAfuAfgAfcUfaUf | A2043 | aUfaGfaUfcAfuAfaaaAfgAfcUfgAfusCfsa | 0.048 | 0.362 | 0.282 |
| D2044 | S2044 | CfaUfaUfaAfaCfUfAfcAfaGfuCfaAfaAf | A2044 | uUfuUfgAfcUfuGfuagUfuUfaUfaUfgsUfsa | 0.314 | 0.904 | 0.937 |
| D2045 | S2045 | CfuUfgAfaCfuCfAfAfcUfcAfaAfaCfuUf | A2045 | aAfgUfuUfuGfaGfuugAfgUfuCfaAfgsUfsg | 0.060 | 0.295 | 0.251 |
| D2046 | S2046 | CfuAfcUfuCfaAfCfAfaAfgUfgAfaAf | A2046 | uUfuCfaCfuUfuUfuguUfgAfaGfuAfgsAfsa | 0.052 | 0.570 | 0.599 |
| D2047 | S2047 | AfaGfaGfcAfaCfUfAfaCfuAfaCfuUfaAf | A2047 | uUfaAfgUfuAfgUfuagUfuGfcUfcUfusCfsu | 0.028 | 0.369 | 0.381 |

TABLE 3-continued

ANGPTL3 modified duplex

| Duplex ID | Sense ID | SS seq (SEQ ID NOS 845-1025, respectively, in order of appearance) | AS ID | AS seq (SEQ ID NOS 1026-1206, respectively, in order of appearance) | 10 nM | RNAimax, Hep3b 0.1 nM | 0.025 nM |
|---|---|---|---|---|---|---|---|
| D2048 | S2048 | AfaAfcAfaGfaUfAfAfuAfgCfaUfcAfaAf | A2048 | uUfuGfaUfgCfuAfuuaUfcUfuGfuUfusUfsu | 0.039 | 0.227 | 0.204 |
| D2049 | S2049 | GfcAfuAfgUfcAfAfuAfaAfaGfaAfaUf | A2049 | aUfuUfcUfuUfuAfuuuGfaCfuAfuGfcsUfsg | 0.032 | 0.437 | 0.422 |
| D2050 | S2050 | AfuAfuAfaAfcUfAfCfaAfgUfcAfaAfaAf | A2050 | uUfuUfuGfaCfuUfguaGfuUfuAfuAfusGfsu | 0.297 | 0.946 | 0.850 |
| D2051 | S2051 | GfaAfcUfcAfaCfUfCfaaAfaAfcUfuGfaAf | A2051 | uUfcAfaGfuUfuUfgagUfuGfaGfuUfcsAfsa | 0.179 | 0.929 | 0.884 |
| D2052 | S2052 | UfaCfuUfcAfaCfAfAfaAfaGfuGfaAfaUf | A2052 | aUfuUfcAfcUfuUfuugUfuGfaAfgUfasGfsa | 0.091 | 0.536 | 0.524 |
| D2053 | S2053 | AfgAfgCfaAfcUfAfAfcUfaAfcUfuAfaUf | A2053 | aUfuAfaGfuUfaGfuuaGfuUfgCfuCfusUfsc | 0.086 | 0.611 | 0.621 |
| D2054 | S2054 | GfaUfaAfuAfgCfAfUfcAfaAfgAfcCfuUf | A2054 | aAfgGfuCfuUfuGfaugCfuAfuUfaUfcsUfsu | 0.058 | 0.676 | 0.591 |
| D2055 | S2055 | CfaUfaGfuCfaAfAfUfaAfaAfgAfaAfuAf | A2055 | uAfuUfuCfuUfuUfauuUfgAfcUfaUfgsCfsu | 0.048 | 0.630 | 0.674 |
| D2056 | S2056 | UfaUfaAfaCfuAfCfAfaGfuCfaAfaAfaUf | A2056 | aUfuUfuUfgAfcUfuguAfgUfuUfaUfasUfsg | 0.072 | 0.534 | 0.459 |
| D2057 | S2057 | AfaCfuCfaAfcUfCfAfaAfaCfuUfgAfaAf | A2057 | uUfuCfaAfgUfuUfugaGfuUfgAfgUfusCfsa | 0.161 | 0.864 | 0.775 |
| D2058 | S2058 | AfcUfuCfaAfcAfAfAfaGfuGfaAfaAfuAf | A2058 | uAfuUfuCfaCfuUfuuuGfuUfgAfaGfusAfsg | 0.198 | 0.969 | 0.865 |
| D2059 | S2059 | GfaGfcAfaCfuAfCfAfcUfuAfcUfuAfaUf | A2059 | aAfuUfaAfgUfuAfguuAfgUfuGfcUfcsUfsu | 0.031 | 0.253 | 0.210 |
| D2060 | S2060 | AfaCfcAfaCfaGfcAfCfAfuAfgUfcAfaAf | A2060 | uAfuUfuGfaCfuAfugcUfgUfuGfuGfusUfsa | 0.035 | 0.561 | 0.569 |
| D2061 | S2061 | AfgUfcAfaAfuAfAfAfaGfaAfaGfaAfaAf | A2061 | uUfcUfaUfuUfcUfuuuAfuUfuGfaCfusAfsa | 0.057 | 0.668 | 0.386 |
| D2062 | S2062 | AfgUfcAfaAfaAfUfGfaAfgAfgGfuAfaAf | A2062 | uUfuAfcCfuCfuUfcauUfuUfuGfaCfusUfsg | 0.720 | 1.017 | 0.924 |
| D2063 | S2063 | CfuUfgAfaAfgCfCfUfcCfuAfgAfaGfaAf | A2063 | uUfcUfuCfuAfgGfaggCfuUfuCfaAfgsUfsu | 0.324 | 1.020 | 0.963 |
| D2064 | S2064 | CfuUfcAfaCfaAfAfAfaGfuGfaAfaUfaUf | A2064 | aUfaUfuUfcAfcUfuuuUfgUfuGfaAfgsUfsa | 0.048 | 0.549 | 0.531 |
| D2065 | S2065 | CfaAfcUfaAfcUfAfAfcUfuAfaUfaUfaAf | A2065 | uUfgAfuAfuUfaAfguuaGfuUfaGfuUfgsUfsu | 0.046 | 0.739 | 0.649 |
| D2066 | S2066 | AfcCfaAfcAfgCfAfUfaGfuCfaAfaUfaAf | A2066 | uUfaUfuUfgAfcUfaugCfuGfuUfgGfusUfsu | 0.076 | 0.840 | 0.777 |
| D2067 | S2067 | GfaAfcCfcAfcAfgCfAfaAfaUfuCfuCfuAf | A2067 | uAfgAfgAfaUfuUfucuGfuGfgGfuUfcsUfsu | 0.103 | 0.916 | 0.808 |
| D2068 | S2068 | GfaAfuAfuGfuCfAfCfuUfgAfaCfuCfaAf | A2068 | uUfgAfgUfuCfaAfgugAfcAfuAfuUfcsUfsu | 0.046 | 0.532 | 0.520 |
| D2069 | S2069 | UfgAfaAfgCfcUfCffUfaGfaAfgAfaAf | A2069 | uUfuUfcUfuCfuAfggaGffCfuUfuCfasAfsg | 0.067 | 0.894 | 0.822 |
| D2070 | S2070 | UfuCfaAfcAfaAfAfAfgUfgAfaAfuAfuUf | A2070 | aAfuAfuUfuCfaCfuuuUfuGfuUfgAfasGfsu | 0.052 | 0.557 | 0.395 |
| D2071 | S2071 | AfaCfuAfaCfuAfAfCfuUfaAfuAfuCfaAf | A2071 | uUfuGfaAfuUfaAfguuAfgUfuAfgUfusGfsc | 0.025 | 0.220 | 0.232 |
| D2072 | S2072 | CfcAfaCfaCfaGfcAfUfAfgUfcAfaAfaAf | A2072 | uUfuAfuUfuGfaCfuauGfcUfgUfuGfgsUfsu | 0.293 | 0.923 | 0.899 |
| D2073 | S2073 | AfaCfcCfaCfaGfcAfAfaAfuUfcUfcAfaAf | A2073 | aUfaGfaGfaAfuUfuucUfgUfgGfgUfusUfsu | 0.021 | 0.375 | 0.356 |
| D2074 | S2074 | UfgUfcAfcUfuGfAfAfcUfcAfaCfuCfaAf | A2074 | uUfgAfgUfuGfaGfuucAfaGfuGfaCfasUfsa | 0.052 | 0.402 | 0.513 |
| D2075 | S2075 | GfaAfaGfcCfuCfCfUfaGfaAfgAfaAfaAf | A2075 | uUfuUfuCfuUfcUfaggAfgGfcUfuUfcsAfsa | 0.171 | 0.904 | 0.893 |
| D2076 | S2076 | AfaUfuUfaGfaAfAfgAfgCfaAfcUfaAf | A2076 | uUfaGfuUfgCfuCfuucUfaAfaUfaUfusUfsc | 0.142 | 0.614 | 0.688 |
| D2077 | S2077 | AfcUfaAfcUfaAfcUfUfaAfuAfuCfaAfaAf | A2077 | uUfuUfgAfuAfuUfaguUfaGfuUfaGfusUfsg | 0.020 | 0.312 | 0.316 |
| D2078 | S2078 | CfaAfcAfgCfaUfAfgUfcAfaAfuAfaAf | A2078 | uUfuAfuUfuGfacuAfUfgCfuGfuUfgsGfsu | 0.026 | 0.313 | 0.393 |
| D2079 | S2079 | CfcAfcAfgCfaAfaAfUfUfcUfcUfaUfcUfuUf | A2079 | aAfgAfuAfgAfgAfaauUfcUfgUfgGfgsUfsu | 0.012 | 0.596 | 0.345 |
| D2080 | S2080 | GfuCfaCfuUfgAfAfCfuCfaAfcUfcAfaAf | A2080 | uUfuGfaGfuUfgAfguuCfaAfgUfgAfcsAfsu | 0.054 | 0.503 | 0.456 |
| D2081 | S2081 | CfuUfcUfaGfaAfGfAfaAfaAfaAfuCfuAf | A2081 | uAfgAfuUfuUfuUfucuUfcUfaGfaAfgsGfsc | 0.050 | 0.596 | 0.531 |
| D2082 | S2082 | AfuUfuAfgAfaAfGfAfGfcAfcAfaCfuAfaAf | A2082 | uUfaGfuUfgCfuCfuucGfcUfuUfcUfaAfasAfsa | 0.064 | 0.806 | 0.928 |
| D2083 | S2083 | CfuAfaCfuAfaCfUfUfaAfuAfuCfaAfaUf | A2083 | aUfuUfgAfuAfuUfaagUfuAfgUfuAfgsUfsu | 0.056 | 0.844 | 0.761 |
| D2084 | S2084 | CfaGfcAfuAfgUfCfAfaAfuAfaAfaGfaAf | A2084 | uUfcUfuUfuAfuUfugaCfuAfuGfcUfgsUfsu | 0.046 | 0.859 | 0.756 |
| D2085 | S2085 | GfaAfaUfaAfgAfAfAfAfuGfuAfaAfaCfaUf | A2085 | aUfgUfuUfuAfcAfuuuCfuUfaUfuUfcsAfsa | 0.039 | 0.615 | 0.612 |
| D2086 | S2086 | UfcAfcUfuGfaAfCfUfcAfaCfuCfaAfaAf | A2086 | uUfuUfgAfgUfuGfaguUfcAfaGfuGfasCfsa | 0.057 | 0.724 | 0.663 |
| D2087 | S2087 | UfcUfaCfuUfcAfAfCfaAfaAfaGfuGfaAf | A2087 | uUfcAfcUfuUfuUfguuGfaAfgUfaGfasAfsu | 0.732 | 1.028 | 0.915 |
| D2088 | S2088 | UfuUfaGfaAfgAfGfCfaAfcUfaAfcUfaAf | A2088 | uUfaGfuUfaGfuUfgcuCfuUfcUfaAfasUfsa | 0.061 | 0.795 | 0.785 |
| D2089 | S2089 | AfaAfaCfaAfgAfUfAffaUfaGfcAfuUfaAf | A2089 | uUfgAfuGfcUfaUfuauCfuUfgUfuUfusUfsc | 0.330 | 1.017 | 0.865 |
| D2090 | S2090 | AfgCfaUfaGfuCfAfAfaUfaAfaAfgAfaAf | A2090 | uUfuCfuUfuUfaUfuugAfcUfaUfgCfusGfsu | 0.038 | 0.606 | 0.589 |
| D2091 | S2091 | AfgAfcCfcAfgCfAfAfcUfcUfcAfaAfGfuUf | A2091 | aAfcUfuGfaGfaGfuugCfuGfgGfuCfusGfsa | 0.301 | 0.850 | 0.753 |
| D2092 | S2092 | AfgUfcCfaUfgGfAfCfaUfuAfaUfuCfaAf | A2092 | uUfgAfaUfuAfaUfgucCfaUfgGfaCfusAfsc | 0.407 | 0.791 | 0.726 |
| D2093 | S2093 | GfaUfgGfaUfcAfCffAfaCfuUfcAfaAf | A2093 | aUfuGfaAfgUfuUfuguGfaUfcCfaUfcsUfsa | 0.120 | 0.658 | 0.654 |
| D2094 | S2094 | CfuUfgAfgGfaUfAfUfuAfcUfcAfuCfaAf | A2094 | uUfgAfuGfaGfuaauCfuCfcUfcAfagsCfsu | 0.071 | 0.610 | 0.645 |
| D2095 | S2095 | AfaAfgAfcAfaCfAfAfaAfcAfuUfaAfuUf | A2095 | aAfuUfaAfuGfuUfuugUfgUfcUfuUfusCfsc | 0.029 | 0.306 | 0.461 |
| D2096 | S2096 | CfaUfuAfuAfuAfUfGfAfaUfaUfuCfuUfuUf | A2096 | aAfaAfgAfaUfaUfucaAfuAfuAfaUfgsUfsu | 0.031 | 0.510 | 0.595 |
| D2097 | S2097 | GfaCfcAfaGfcAfAfcfuCfaAfgAfuUfuUf | A2097 | aAfaCfuUfgAfgAfguuGfcUfgGfuCfsUfsg | 0.075 | 0.697 | 0.845 |
| D2098 | S2098 | GfgAfcUfcAfcAfAfcUfcAfuCfuAfaAfsUf | A2098 | uUfuUfaGfaUfgAfuuuUfgUfgAfuCfcsAfsu | 0.130 | 0.831 | 0.951 |
| D2099 | S2099 | GfaAfgAfuAfuAfcfUfcCfaUfaGfuAfaAf | A2099 | uUfcUfaCfuAfuGfgaguAfuAfuCfuUfcsUfsc | 0.058 | 0.828 | 0.938 |
| D2100 | S2100 | GfaCfaAfcAfaAfcfAfuUfaUfaUfuUfaAf | A2100 | uUfcAfaUfaUfaAfuguUfuGfuUfgUfcsUfsu | 0.026 | 0.564 | 0.856 |
| D2101 | S2101 | GfgGfaAfaUfcAfCfGfaAfaCfcAfaCfuAf | A2101 | uAfgUfuGfgUfUfcguGfaUfuUfcCfcsAfsa | 0.314 | 0.948 | 1.033 |
| D2102 | S2102 | AfcCfcAfgGfCfAfaCfUfcUfcAfaGfaUfuUf | A2102 | aAfaUfcUfuGfaGfagUfgCfuGfgGfusCfsu | 0.033 | 0.448 | 0.675 |
| D2103 | S2103 | GfgAfcGfaAfaUfAfUfcAfcCfaUfcCfsAf | A2103 | uUfcGfaUfgGfuUfgaauUfaAfuGfuCfcsAfsu | 0.156 | 0.897 | 0.912 |
| D2104 | S2104 | GfaUfcAfcAfaAfCfuUfcUfaAfgAfaAf | A2104 | uUfuCfaUfuAfaGfuuuUfgGfuAfuCfcsCfsa | 0.056 | 0.619 | 0.769 |
| D2105 | S2105 | AfcUfcCfaUfaGfUfGfaAfgCfaAfuCfuAf | A2105 | uAfgAfuUfgCfuUfcacUfaUfgGfaGfusAfsu | 0.100 | 0.823 | 0.925 |
| D2106 | S2106 | AfcAfaCfaAfaCfAfUfuAfaUfuAfgAfaUf | A2106 | aUfuCfaAfuUfaAfugUfuGfuUfgsCfsu | 0.035 | 0.565 | 0.843 |
| D2107 | S2107 | GfgAfaAfuCfaCfgAfaAfcCfaAfCfuAfaUf | A2107 | aUfaGfuUfgGfuUfucgUfgAfuUfuCfcsCfsu | 0.076 | 0.701 | 0.890 |
| D2108 | S2108 | CfcCfaGfcAfaCfUfCffcAfaGfaUfuUfuUf | A2108 | aAfaAfuCfuUfgAfgagUfuGfcUfgGfgsUfsc | 0.057 | 0.626 | 0.884 |
| D2109 | S2109 | GfaCfaUfuAfaUffUfCfaAfcAfuCfgAfaUf | A2109 | aUfuCfgAfuGfuUfgaaUfuAfaUfgUfcsCfsa | 0.160 | 0.873 | 1.012 |
| D2110 | S2110 | AfaCfgUfgGfgAfGfaAfcfuAfcAfaAfuAf | A2110 | uUfuUfgUfaGfuUfucuCffCfaCfgUfusUfsc | 0.101 | 0.881 | 0.981 |
| D2111 | S2111 | CfuCfcAfuAfgUfgAfAfgCfaAfucCfaAf | A2111 | uUfaGfaUfuGfcUfucaCfuAfuGfgAfgsUfsa | 0.026 | 0.435 | 0.691 |
| D2112 | S2112 | CfaAfcAfaAfcAfUfUfaAfuUfaGfaAfuAf | A2112 | uAfuUfcUfaAfuUfaauGfuUfuGfuUfgsUfsc | 0.154 | 0.882 | 1.091 |
| D2113 | S2113 | GfaAfaUfcAfcGfAfaAfcfaCfaAfcUfaAf | A2113 | uUfaGfuUfgGfuUfucuGfuGfaUfuUfcsCfsc | 0.045 | 0.764 | 1.004 |
| D2114 | S2114 | CfuUfcUfaAfgUfUfUfuUfuGfuGfaAf | A2114 | uAfgAfcAfuUfgAfaAfaaCfuUfgAfgAfgsUfsu | 0.105 | 0.925 | 0.988 |
| D2115 | S2115 | AfcAfuUfaAfuUfCfCfaCfaUfcGfaAfuUf | A2115 | aUfuCfgAfuGfuUfgaAfuUfaAfuUfcsCfsa | 0.114 | 0.919 | 0.905 |
| D2116 | S2116 | GfgGfaGfaAfcUfAfCffaAfaUfaUfgGfuUf | A2116 | aAfcCfaUfaUfuUfguaGfuUfcUfcCfcsAfsc | 0.234 | 1.023 | 0.951 |
| D2117 | S2117 | UfcCfaUfaGfuGfAfAfgCfaAfuCfuAfaUf | A2117 | aUfuAfgAfuUfgCfuucAfcUfaUfgGfasGfsu | 0.033 | 0.566 | 0.778 |
| D2118 | S2118 | AfaCfaAfaCfaUfUfAfuAfaUfuAfgAfuAfuUf | A2118 | aUfaUfuCfaAfuUfuaAfuGfuUfuGfusGfsu | 0.031 | 0.535 | 0.785 |
| D2119 | S2119 | UfgGfcAfaUfgUfCffCfcAfaUfgCfaAf | A2119 | aUfuGfcAfuUfgGfggaCfaUfuGfcCfasGfsu | 0.065 | 0.815 | 0.967 |
| D2120 | S2120 | UfcAfgGfuAfgUfCfCfaUfgGfaCfaUfuAf | A2120 | uAfaUfgUfcCfaUfggaCfuAfcCfuGfasUfsa | 0.223 | 0.825 | 0.924 |

TABLE 3-continued

ANGPTL3 modified duplex

| Duplex ID | Sense ID | SS seq (SEQ ID NOS 845-1025, respectively, in order of appearance) | AS ID | AS seq (SEQ ID NOS 1026-1206, respectively, in order of appearance) | RNAimax, Hep3b 10 nM | 0.1 nM | 0.025 nM |
|---|---|---|---|---|---|---|---|
| D2121 | S2121 | UfuAfaUfuCfaAfCfAfuCfgAfaUfaGfaUf | A2121 | aUfcUfaUfuCfgAfuguUfgAfaUfuAfasUfsg | 0.083 | 0.781 | 0.915 |
| D2122 | S2122 | GfgAfgAfaCfuAfCfAfaAfuAfuGfgUfuUf | A2122 | aAfaCfcAfuAfuUfuguAfgUfuCfuCfcsCfsa | 0.079 | 0.680 | 0.767 |
| D2123 | S2123 | CfcAfuAfgUfgAfAfGfcAfaUfcUfaAfuUf | A2123 | aAfuUfaGfaUfuGfcuuCfaCfuAfuGfgsAfsg | 0.026 | 0.537 | 0.793 |
| D2124 | S2124 | AfcAfaAfcAfuUfAfUfaUfuGfaAfuAfuUf | A2124 | aAfuAfuUfcAfaUfauaAfuGfuUfuGfusUfsg | 0.044 | 0.680 | 0.828 |
| D2125 | S2125 | AfaUfgCfaAfuCfCfCfgGfaAfaAfcAfaAf | A2125 | uUfuGfuUfuUfcCfgggAfuUfgCfaUfusUfsg | 0.349 | 0.971 | 1.005 |
| D2126 | S2126 | CfaGfgUfaGfuCfCfAfuGfgAfcAfuUfaAf | A2126 | uUfaAfuGfuCfcAfuggAfcUfaCfcUfgsAfsu | 0.070 | 0.548 | 0.546 |
| D2127 | S2127 | UfuCfaAfcAfuCfGfAfaUfaGfaUfgGfaUf | A2127 | aUfcCfaUfcUfaUfucgAfuGfuUfgAfasUfsu | 0.225 | 0.958 | 0.967 |
| D2128 | S2128 | GfuUfgGfgCfcUfAfGfaGfaAfgAfuAfuAf | A2128 | uAfuAfuCfuUfcUfcuaGfgCfcCfaAfcsCfsa | 0.765 | 0.969 | 0.922 |
| D2129 | S2129 | CfaUfaGfuGfaAfGfCfaAfuCfuAfaUfuAf | A2129 | uAfaUfuAfgAfuUfgcuUfcAfcUfaUfgsGfsa | 0.028 | 0.583 | 0.777 |
| D2130 | S2130 | AfaCfaUfuAfuAfUfUfgAfaUfaUfuCfuUf | A2130 | aAfgAfaUfaUfuCfaauAfuAfaUfgUfusUfsg | 0.249 | 0.916 | 0.981 |
| D2131 | S2131 | GfcAfaUfcCfcGfGfAfaAfaCfaAfaGfaUf | A2131 | aUfcUfuUfgUfuUfuccGfgGfaUfuGfcsAfsu | 0.435 | 1.002 | 1.019 |
| D2132 | S2132 | GfgUfaGfuCfcAfUfGfgAfcAfuUfaAfuUf | A2132 | aAfuUfaAfuGfuCfcauGfgAfcUfaCfcsUfsg | 0.427 | 0.988 | 0.918 |
| D2133 | S2133 | AfuCfgAfaUfaGfAfUfgGfaUfcAfcAfaAf | A2133 | uUfuGfuGfaUfcCfaucUfaUfuCfgAfusGfsu | 0.170 | 0.706 | 0.890 |
| D2134 | S2134 | CfcUfaGfaGfaAfGfAfuAfuUfcUfcUfaGf | A2134 | aUfgGfaGfuAfuAfucuUfcUfcUfaGfgsCfsc | 0.033 | 0.543 | 0.733 |
| D2135 | S2135 | GfuUfgGfaAfgAfCfUfgGfaAfaGfaCfaAf | A2135 | uUfgUfcUfuUfcCfaguCfuUfcCfaAfcsUfsc | 0.137 | 0.975 | 0.944 |
| D2136 | S2136 | AfcAfuUfaUfaUfUfGfaAfuAfuUfcUfuUf | A2136 | aAfaGfaAfuAfuUfcaaUfaUfaAfuGfusUfsu | 0.114 | 0.882 | 0.940 |
| D2137 | S2137 | CfaAfuCfcCfgGfAfAfaAfcAfaAfgAfuUf | A2137 | aAfuCfuUfuGfuUfuucCfgGfgAfuUfgsCfsa | 0.155 | 0.755 | 0.686 |
| D2138 | S2138 | CfuAfcUfuGfgGfaUfcAfcAfaAfgGfaAf | A2138 | uUfgCfuUfuGfuGfaucCfcAfaGfuAfgsAfsa | 0.196 | 0.825 | 0.658 |
| D2139 | S2139 | AfcAfaAfcCfuUfaAfAfUfgGfuAfaAfuAfaAf | A2139 | uAfuAfuUfuAfcCfauuUfaGfgUfuGfusUfsu | 0.133 | 0.704 | 0.671 |
| D2140 | S2140 | AfuCfcAfuCfcAfAfCfaGfaUfuCfaGfaAf | A2140 | uUfcUfgAfaUfcUfguuGfgAfuGfgAfusCfsa | 0.184 | 0.775 | 0.658 |
| D2141 | S2141 | AfaCfuGfaGfgCfaUfAfaUfuAfaAfaAfgAf | A2141 | uCfuUfuUfaAfaUfuugCfcUfcAfgUfusCfsa | 0.076 | 0.682 | 0.777 |
| D2142 | S2142 | AfgAfgUfaUfgUfGfGfUfaAaAfaCfaUfaUfcUfgUf | A2142 | aCfaGfaUfuUfuUfacaCfaUfaCfuCfusGfsu | 0.448 | 0.659 | 0.761 |
| D2143 | S2143 | AfaUfcCfcGfgAfAfaAfcAfaAfaGfaUfuUf | A2143 | aAfaUfcUfuUfgUfuuuCfcGfgGfaUfusGfsc | 0.097 | 0.844 | 0.924 |
| D2144 | S2144 | UfaCfuUfgGfgAfUfCfaCfaAfaGfcAfaAf | A2144 | uUfuGfcUfuUfgUfgauCfcCfaAfgUfasGfsa | 0.084 | 0.875 | 0.947 |
| D2145 | S2145 | CfaAfcCfuAfaAfUfgGfgUfaAfaUfaUfaAf | A2145 | uUfaUfaUfuUfaCfcauUfuAfgGfuUfgsUfsu | 0.104 | 0.811 | 0.814 |
| D2146 | S2146 | UfuGfaAfuGfaAfCfUfgAfgGfcAfuAfaUf | A2146 | aAfuUfaUfgCfcUfcaguUfcAfuUfcAfasAfsg | 0.046 | 0.549 | 0.680 |
| D2147 | S2147 | AfcUfgAfgGfcAfAfAfuUfuAfaAfaGfgAf | A2147 | uCfcUfuUfuAfaAfuuuGfcCfuCfaGfusUfsc | 0.079 | 0.890 | 1.005 |
| D2148 | S2148 | GfaGfuAfuGfuGfUfAfaAfaAfuCfuGfuAf | A2148 | uAfcAfgAfuUfuUfuacAfcAfuAfcUfcsUfsg | 0.497 | 0.676 | 0.783 |
| D2149 | S2149 | AfcUfuGfgGfaUfCfAfcAfaAfgCfaAfaAf | A2149 | uUfuUfgCfuUfuGfugaUfcCfcAfaGfusAfsg | 0.049 | 0.699 | 0.907 |
| D2150 | S2150 | AfuGfgUfaAfaUfAfUfaAfcAfcAfcUfuUf | A2150 | uUfgGfuUfuGfuUfauaUfuUfaCfcAfusUfsu | 0.093 | 0.928 | 0.941 |
| D2151 | S2151 | UfgGfaUfgAfaCfUfGfaGfgCfaAfaUfuUf | A2151 | aAfaUfuUfgCfcUfcagUfuCfaUfcCfasAfsa | 0.201 | 0.736 | 0.885 |
| D2152 | S2152 | CfuGfaGfgCfaAfAfUfuAfaAfaAfgGfcAf | A2152 | uGfcCfuUfuUfaAfauuUfgCfcUfcAfgsUfsu | 0.071 | 0.938 | 0.872 |
| D2153 | S2153 | AfgUfaUfgUfgUfAfAfaAfaUfcUfgUfaAf | A2153 | uUfaCfaGfaUfuUfuuaCfaCfaUfaCfusCfsu | 0.504 | 0.816 | 0.689 |
| D2154 | S2154 | GfaAfaAfcAfaAfGfAfuUfuGfuGfuUfuUf | A2154 | aAfaCfaCfcAfaAfucuUffcGfuUfuUfcsCfsg | 0.061 | 0.723 | 0.922 |
| D2155 | S2155 | AfgUfgUfgGfaGfaAfaAfcAfCfuGfaAf | A2155 | uGfaGfgUfuGfuUfuucUfcCfaCfaCfusCfsa | 0.071 | 0.689 | 0.869 |
| D2156 | S2156 | GfuCfuCfaAfaAfUfgGfgAfaGfgUfuAfuAf | A2156 | uAfuAfaCfcUfuCfcauUfuUfgAfgAfcsUfsu | 0.133 | 0.643 | 0.974 |
| D2157 | S2157 | GfaAfuGfaAfcUfGfAfgGfcAfaAfuUfuAf | A2157 | uAfaAfuUfuGfcCfucaGfuUfcAfuUfcsAfsa | 0.204 | 0.751 | 1.008 |
| D2158 | S2158 | UfgAfgGfcAfaAfUfUfuAfaAfaGfgCfaAf | A2158 | uUfgCfcUfuUfuAfaaUfuGfcCfuCfasGfsu | 0.089 | 0.820 | 0.937 |
| D2159 | S2159 | GfuAfGfuGfuAfAfAfaAfuCfuGfuAfaUf | A2159 | aUfuAfcAfgAfuUfuuuAfcAfcAfuAfcsUfsc | 0.535 | 0.697 | 0.788 |
| D2160 | S2160 | AfaAfaCfaAfaGfAfuUfuGfuGfuUfuUf | A2160 | aAfaAfcAfcAfaAfaucUfuUfgUfuUfusCfsc | 0.297 | 0.954 | 1.004 |
| D2161 | S2161 | GfuGfuGfgAfgAfAfaAfcAfcCfuAfaAf | A2161 | uUfuAfgGfuUfgUfuuuCfuCfcAfcAfcsUfsc | 0.178 | 0.872 | 0.918 |
| D2162 | S2162 | AfuGfgAfaGfgGfuUfAfuAfcUfcUfaUfaAf | A2162 | uUfaUfaGfaGfuAfuaaCfcUfuCfcAfusUfsu | 0.026 | 0.489 | 0.890 |
| D2163 | S2163 | AfaUfgAfaCfuGfAfGfgCfaAfaUfuUfaAf | A2163 | uUfaAfaUfuUfgCfcucAfgUfuCfaUfusCfsa | 0.111 | 0.789 | 0.859 |
| D2164 | S2164 | GfaGfgCfaAfaUfUfUfaAfaAfgGfcAfaUf | A2164 | aUfuGfcCfuUfuUfaaaUfuUfgCfcUfcsAfsg | 0.241 | 0.956 | 0.869 |
| D2165 | S2165 | UfaUfgUfgUfaAfAfAfaUfcUfgUfaAfuAf | A2165 | uAfuUfaCfaGfaUfuuuUfaCfaCfaUfasCfsu | 0.571 | 0.762 | 0.931 |
| D2166 | S2166 | AfcAfaAfgAfuUfUfgGfgUfgUfuUfuCfuAf | A2166 | uAfgAfaAfaCfaCfcaaAfuCfuUfuGfusUfsg | 0.106 | 0.981 | 0.924 |
| D2167 | S2167 | UfgUfgGfaGfaAfAfcAfcCfuUfcUfuAfcAf | A2167 | uUfaUfaGfgUfuUfuuuUfcUfcCfaCfasCfsu | 0.064 | 0.765 | 0.902 |
| D2168 | S2168 | UfgGfaAfgGfuUfAfUfaCfuCfuAfuAfaAf | A2168 | uUfuAfuAfgAfgUfauaAfcCfuUfcCfasUfsu | 0.029 | 0.675 | 0.859 |
| D2169 | S2169 | AfuGfaAfcUfgAfGfGfcAfaAfuUfuAfaAf | A2169 | uUfuAfaAfuUfuGfccuCfaGfuUfcAfusUfsc | 0.054 | 0.733 | 0.843 |
| D2170 | S2170 | AfgGfcAfaAfuUfUfAfaAfaGfgCfaAfuAf | A2170 | uAfuUfgCfcUfuUfuaaAfuUfuGfcCfusCfsa | 0.075 | 0.754 | 0.881 |
| D2171 | S2171 | AfaGfaUfuUfgGfgUfGfuUfuUfcUfaCfuUf | A2171 | aAfgUfaGfaAfaAfcacCfaAfaUfcUfusUfsg | 0.303 | 1.065 | 0.977 |
| D2172 | S2172 | AfaAfcAfaAfcCfUfAfAfaUfgGfuAfaAfuAf | A2172 | uAfuUfuAfcCfaUfuuaGfgUfuUfgUfusUfsc | 0.101 | 0.855 | 0.880 |
| D2173 | S2173 | AfuAfcUfcUfaUfaUfAfAfaAfuCfaAfcCfaAf | A2173 | uUfgGfuUfgAfuUfuuaUfaGfaGfuAfusAfsa | 0.107 | 0.961 | 0.960 |
| D2174 | S2174 | UfgAfaCfuGfaGfGfCfaAfaUfuUfaAfaAf | A2174 | uUfuUfaAfaUfuUfgccUfcAfgUfuCfasUfsu | 0.078 | 0.714 | 0.878 |
| D2175 | S2175 | GfgCfaAfaUfuUfAfaAfaGfGfcAfaUfaAf | A2175 | uUfaUfuGfcCfuUfuuaAfaUfuUfgCfcsUfsc | 0.054 | 0.767 | 0.918 |
| D2176 | S2176 | UfuUffuUfcAfcUfUfGfgGfaUfcAfcAfaAf | A2176 | uUfuGfuGfaUfcCfcaaGfuAfgAfaAfasCfsa | 0.915 | 1.030 | 0.916 |
| D2177 | S2177 | AfaCfaAfcCfuAfAfuGfgUfaAfaUfaUf | A2177 | aUfaUfuUfaCfcAfuuuAfgGfuUfgUfusUfsu | 0.042 | 0.260 | 0.448 |
| D2178 | S2178 | UfaCfuCfuAfuAfAfaAfUfcAfaCfcAfaAf | A2178 | uUfuGfgUfuGfaUfuuuAfuAfgAfgUfasUfsa | 0.063 | 0.897 | 0.869 |
| D2179 | S2179 | GfaAfcUfgAfgGfCfAfaAfuUfuAfaAfaAf | A2179 | uUfuUfuAfaAfuUfugcCfuCfaGfuUfcsAfsu | 0.178 | 0.858 | 0.869 |
| D2180 | S2180 | CfaGfaGfuAfuGfUfGfuAfaAfaAfuCfuUf | A2180 | aAfgAfuUfuUfuAfcacAfuAfcUfcUfgsUfsg | 0.436 | 0.677 | 0.813 |

Example 4: In Vitro Silencing Activity with Various Chemical Modifications on ANGPTL3 siRNA Cell Culture and Transfections Hep3B cells (ATCC, Manassas, VA) were grown to near confluence at 37° C. in an atmosphere of 5% CO₂ in RPMI (ATCC) supplemented with 10% FBS, streptomycin, and glutamine (ATCC) before being released from the plate by trypsinization. Transfection was carried out by adding 14.8 µl of Opti-MEM plus 0.2 µl of Lipofectamine RNAiMax per well (Invitrogen, Carlsbad CA. cat #13778-150) to 5 µl of siRNA duplexes per well into a 96-well plate and incubated at room temperature for 15 minutes. 80 µl of complete growth media without antibiotic containing ~2×10⁴ Hep3B cells were then added to the siRNA mixture. Cells were incubated for either 24 or 120 hours prior to RNA purification. Single dose experiments were performed at 10 nM and 0.1 nM final duplex concentration and dose response experiments were done at 10, 1, 0.5, 0.1, 0.05, 0.01, 0.005, 0.001, 0.0005, 0.0001, 0.00005 and 0.00001 nM final duplex concentration unless otherwise stated.

cDNA Synthesis Using ABI High Capacity cDNA Reverse Transcription Kit (Applied Biosystems, Foster City, CA, Cat #4368813)

A master mix of 2 µl 10λ Buffer, 0.8 µl 25× dNTPs, 2 µl Random primers, 1 µl Reverse Transcriptase, 1 µl RNase inhibitor and 3.2 µl of H$_2$O per reaction were added into 10p total RNA. cDNA was generated using a Bio-Rad C-1000 or 5-1000 thermal cycler (Hercules, CA) through the following steps: 25° C. 10 min, 37° C. 120 min, 85° C. 5 sec, 4° C. hold.

Real Time PCR

2 µl of cDNA was added to a master mix containing 0.5 µl GAPDH TaqMan Probe (Applied Biosystems Cat #4326317E), 0.5 µl ANGPTL TaqMan probe (Applied Biosystems cat #Hs00205581_m1) and 5 µl Lightcycler 480 probe master mix (Roche Cat #04887301001) per well in a 384 well 50 plates (Roche cat #04887301001). Real time PCR was done in an ABI 7900HT Real Time PCR system (Applied Biosystems) using the ΔΔCt(RQ) assay. Each duplex was tested in two independent transfections, and each transfection was assayed in duplicate, unless otherwise noted in the summary tables.

To calculate relative fold change, real time data was analyzed using the ΔΔCt method and normalized to assays performed with cells transfected with 10 nM AD-1955, or mock transfected cells. IC$_{50}$s were calculated using a 4 parameter fit model using XLFit and normalized to cells transfected with AD-1955 or naïve cells over the same dose range, or to its own lowest dose. AD-1955 sequence, used as a negative control, targets luciferase and has the following sequence:

sense: cuuAcGcuGAGuAcuucGAdTsdT (SEQ ID NO: 1207);
antisense: UCGAAGuACUcAGCGuAAGdTsdT (SEQ ID NO: 1208).

The various embodiments described above can be combined to provide further embodiments. All of the U.S. patents, U.S. patent application publications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

We claim:

1. A double-stranded RNAi agent capable of inhibiting the expression of a target gene, comprising a sense strand and an antisense strand, each strand having 14 to 30 nucleotides, wherein the sense strand sequence is represented by formula (I):

$$5'n_p\text{-}N_a\text{-}(XXX)_i\text{-}N_b\text{-}YYY\text{-}N_b\text{-}(ZZZ)_j\text{-}N_a\text{-}n_q3' \qquad (I)$$

wherein:
i is 1 and j is 0; or i is 0 and j is 1; or both i and j are 1;
p and q are each independently 0-6;
each $N_a$ independently represents an oligonucleotide sequence comprising 2-25 modified nucleotides, each sequence comprising at least two differently modified nucleotides;
each $N_b$ independently represents an oligonucleotide sequence comprising 1, 2, 3, 4, 5, or 6 modified nucleotides;
each $n_p$ and $n_q$ independently represent an overhang nucleotide;
XXX, YYY and ZZZ each independently represent one motif of three identical modifications on three consecutive nucleotides; and
YYY represents three 2'-F modified nucleotides, and the YYY motif occurs at the 9, 10 and 11 positions of the sense strand from the 5'-end;
the modification of each nucleotide next to a XXX, YYY or ZZZ motif is a different modification than the modification of the motif that the nucleotide is next to; and
at least one of the sense strand and antisense strand contains at least one phosphorothioate internucleotide modification within the first 5 nucleotides, counting from the 5'-end of the strand.

2. The double-stranded RNAi agent of claim 1, wherein the antisense strand comprises two blocks of two phosphorothioate or methylphosphonate internucleotide linkages separated by 1, 2, 3, 4, 5, 6, 7, 8, 9, 10, 11, 12, 13, 14, 15, 16, 17, or 18 phosphate internucleotide linkages.

3. The double-stranded RNAi agent of claim 2, wherein the antisense strand comprises two blocks of two phosphorothioate internucleotide linkages separated by 17 phosphate internucleotide linkages.

4. The double-stranded RNAi agent of claim 1, wherein double-stranded RNAi agent comprises two phosphorothioate internucleotide linkage modifications within position 1-5 (counting from the 5'-end) of the sense strand, and one phosphorothioate internucleotide linkage modification at positions 1 and 2 and two phosphorothioate internucleotide linkage modifications within positions 18-23 of the antisense strand (counting from the 5'-end).

5. The double-stranded RNAi agent of claim 1, wherein double-stranded RNAi agent comprises one phosphorothioate internucleotide linkage modification within position 1-5 of the sense strand (counting from the 5'-end), and two phosphorothioate internucleotide linkage modifications at positions 1 and 2 and one phosphorothioate internucleotide linkage modification within positions 18-23 of the antisense strand (counting from the 5'-end).

6. The double-stranded RNAi agent of claim 1, wherein the duplex region is 17-30 nucleotide pairs in length.

7. The double-stranded RNAi agent of claim 6, wherein the duplex region is 27-30 nucleotide pairs in length.

8. The double-stranded RNAi agent of claim 1, wherein each strand has 17-30 nucleotides.

9. The double-stranded RNAi agent of claim 8, wherein the nucleotides are modified with either 2'-$OCH_3$ or 2'-F.

10. The double-stranded RNAi agent of claim 1, wherein the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, and combinations thereof.

11. The double-stranded RNAi agent of claim 1, wherein the modifications on the nucleotides are selected from the group consisting of 2'-O-methyl nucleotide, 2'-deoxyfluoro nucleotide, 2'-O-N-methylacetamido (2'-O-NMA) nucleotide, a 2'-O-dimethylaminoethoxyethyl (2'-O-DMAEOE) nucleotide, 2'-O-aminopropyl (2'-O-AP) nucleotide, 2'-ara-F, and combinations thereof.

12. The double-stranded RNAi agent of claim 1, further comprising at least one ligand.

13. The double-stranded RNAi agent of claim 12, wherein the ligand is one or more GalNAc derivatives attached through a bivalent or trivalent branched linker.

14. The double-stranded RNAi agent of claim 12, wherein the ligand is attached to the 3' end of the sense strand.

15. The double-stranded RNAi agent of claim 1, wherein the base pair at the 1 position of the 5'-end of the duplex is an AU base pair.

16. A pharmaceutical composition comprising the double-stranded RNAi agent according to claim 1 in combination with a pharmaceutically acceptable carrier or excipient.

17. The pharmaceutical composition of claim 16, wherein the double-stranded RNAi agent is administered through subcutaneous or intravenous administration.

18. A method for inhibiting the expression of a target gene in a subject comprising the step of administering the double-stranded RNAi agent according to claim 1 to the subject, in an amount sufficient to inhibit expression of the target gene.

19. The method of claim 18, wherein the double-stranded RNAi agent is administered through subcutaneous or intravenous administration.

20. A method for delivering a polynucleotide to a specific target of a subject, the method comprising: delivering the double-stranded RNAi agent according to claim 1 by subcutaneous administration into the subject.

* * * * *